(12) United States Patent
Moore

(10) Patent No.: US 8,927,505 B2
(45) Date of Patent: *Jan. 6, 2015

(54) NUTRITIVE COMPOSITIONS AND METHODS OF USING SAME

(75) Inventor: Eileen Moore, Parma, OH (US)

(73) Assignee: Pentec Health, Inc., Boothwyn, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/847,513

(22) Filed: Jul. 30, 2010

(65) Prior Publication Data

US 2010/0317602 A1 Dec. 16, 2010

Related U.S. Application Data

(63) Continuation-in-part of application No. 12/498,773, filed on Jul. 7, 2009.

(60) Provisional application No. 61/078,636, filed on Jul. 7, 2008, provisional application No. 61/080,567, filed on Jul. 14, 2008, provisional application No. 61/292,139, filed on Jan. 4, 2010, provisional application No. 61/292,806, filed on Jan. 6, 2010.

(51) Int. Cl.
| | | |
|---|---|---|
| *A01N 43/04* | (2006.01) | |
| *A61K 31/70* | (2006.01) | |
| *A61K 45/06* | (2006.01) | |
| *A61K 31/198* | (2006.01) | |
| *A61K 31/20* | (2006.01) | |
| *A61K 31/7004* | (2006.01) | |

(52) U.S. Cl.
CPC .............. *A61K 45/06* (2013.01); *A61K 31/198* (2013.01); *A61K 31/20* (2013.01); *A61K 31/7004* (2013.01)
USPC ........................................................ 514/23

(58) Field of Classification Search
USPC ........................................................ 514/23
See application file for complete search history.

(56) References Cited

U.S. PATENT DOCUMENTS

| | | | |
|---|---|---|---|
| 4,489,097 A | 12/1984 | Stone | |
| 4,491,589 A | 1/1985 | Dell et al. | |
| 4,604,286 A * | 8/1986 | Kawajiri ..................... | 424/601 |
| 4,670,261 A | 6/1987 | Samejima et al. | |
| 5,122,515 A | 6/1992 | Smith et al. | |
| 5,278,149 A | 1/1994 | Provost et al. | |
| 5,571,783 A | 11/1996 | Montagne et al. | |
| 5,767,123 A | 6/1998 | Yoshida et al. | |
| 6,610,206 B1 | 8/2003 | Callan et al. | |
| 6,916,424 B2 | 7/2005 | Collins et al. | |
| 7,323,206 B1 | 1/2008 | Driscoll et al. | |
| 7,445,801 B2 | 11/2008 | Faict et al. | |
| 7,670,491 B2 | 3/2010 | Callan et al. | |
| 2004/0209814 A1 | 10/2004 | Nauck et al. | |
| 2005/0148647 A1 | 7/2005 | Landry et al. | |
| 2006/0211631 A1 | 9/2006 | Mitsumoto et al. | |
| 2007/0092579 A1 | 4/2007 | Trouilly et al. | |
| 2007/0196445 A1 | 8/2007 | Abbruzzese et al. | |
| 2009/0203626 A1 | 8/2009 | Brand et al. | |
| 2010/0136133 A1 | 6/2010 | Moore et al. | |
| 2010/0170849 A1 | 7/2010 | Callan et al. | |
| 2010/0176340 A1 | 7/2010 | Callan et al. | |
| 2012/0006748 A1 | 1/2012 | Callan et al. | |

FOREIGN PATENT DOCUMENTS

| | | |
|---|---|---|
| CA | 2129991 A1 | 7/1994 |
| CN | 85107296 A | 4/1987 |
| EP | 1849466 | 1/2012 |
| JP | 2002-045420 A | 2/2002 |
| JP | 2007056013 A | 3/2007 |
| JP | 2007-137836 A | 6/2007 |
| WO | WO 82/03773 A1 | 11/1982 |
| WO | WO 99/20249 A1 | 4/1999 |
| WO | WO 2003/009828 A1 | 2/2003 |
| WO | 2007/016615 | 2/2007 |
| WO | WO 2007/121807 A1 | 11/2007 |
| WO | WO 2010/055963 A1 | 5/2010 |

OTHER PUBLICATIONS

Vassalotti, J.A. "Nutritional Strategies for the Patient with Diabetic Nephropathy" Chapter 10 of Nutritional Strategies for the Diabetic/Prediabetic Patient, Editor: Mechanick, J.I., 2006, pp. 149-169.*
Gura, K.M. et al. Nutrition in Clinical Practice 2009, 24, 6, 709-717.*
Klein, C.J. et al. J. Am. Dietetic. Assoc. 1998, 98, 7, 795-806.*
McCann, L. et al. Am. J. Kid. Dis. 1999, 33, 6, 1131-1135.*
Abbas, et al. Biochemical nutritional parameters and their impact on hemodialysis efficiency. Saudi J Kidney Dis Transpl. 2009; 20(6):1105-1109.
International search report and written opinion dated Feb. 28, 2011 for PCT Application No. US10/03192.

(Continued)

*Primary Examiner* — Sean Basquill
*Assistant Examiner* — Andrew S Rosenthal
(74) *Attorney, Agent, or Firm* — Stradley Ronon Stevens & Young, LLP

(57) ABSTRACT

The invention provides intradialytic parenteral nutrition (IDPN) compositions with low carbohydrate for the treatment of malnutrition in dialysis subjects. In some embodiments, the IDPN compositions are advantageous for the treatment of malnutrition in subjects who are diabetic or suffer from other glucose management related pathologies or subjects who benefit from strict fluid management.

51 Claims, 44 Drawing Sheets

(56) References Cited

OTHER PUBLICATIONS

Kalantar-Zadeh, et al. A Malnutrition-Inflammation Score is Correlated With Morbidity and Mortality in Maintenance Hemodialysis Patients. American Journal of Kidney Diseases. 2001; 38(6):1251-1263.
Baxter Healthcare. Nutrineal Product Label Information. Aug. 5, 2005.
Charra, et al. Volume control, blood pressure and cardiovascular function. Lesson from hemodialysis treatment. Nephron Physiol. 2003;93(4):p. 94-101.
Dezfuli, et al. Severity of hypoalbuminemia predicts response to intradialytic parenteral nutrition in hemodialysis patients. J Ren Nutr. Jul. 2009;19(4):291-7.
Dukkipati, et al. Is there a role for intradialytic parenteral nutrition? A review of the evidence. Am J Kidney Dis. Feb. 2010;55(2):352-64. Epub Oct. 25, 2009.
Fliser, et al. Insulin resistance and renal disease. Contrib Neprhol 2006; 151:203-11.
Goldstein, et al. Intradialytic Paretneral Nutrition "Evolution and Current Concepts. Journal of Rena Nutrition,"; voll (1) Jan. 1991: pp. 9-22.
Guarnieri, et al. Insulin resistance in chronic uremia J Ren Nutr. Jan. 2009;19(1):20-4.
Guarnieri, et al. Mechanisms of malnutrition in uremia. Kidney Int Suppl. Nov. 1997; 62: S41-44.
International search report and written opinion dated Mar. 9, 2010 for PCT Application No. US2009/049800.
International search report and written opinion dated Sep. 27, 2010 for PCT Application No. US10/43944.
Miller. Commercial premixed parenteral nutrition: Is it right for your institution? Nutr Clin Pract. Aug.-Sep. 2009;24(4):459-69.
Moore, et al. Intradialytic Parenteral Nutrition: A Nutrition Support Intervention for High-risk Malnutrition in Chronic Kidney Disease. Support Line. 2007; 29(5): 6-16.
Moore. Challenges of nutrition intervention for malnourished dialysis patients. J Infus Nurs. Nov.-Dec. 2008;31(6):361-6.
Nesrallah, et al. Can extracelluar fluid volume expansion in hemodialysis patients be safely reduced using the hemocontrol biofeedback algorithm? A randomizxed TrialASAIO J. May-Jun. 2008;54(3):270-4.
Nesrallah, et al. Volume control and blood pressure management in patients undergoing quotidian hemodialysis Am J Kidney Dis. Jul. 2003;42(1 Suppl):13-7.
Raimann, et al. Consequnces of overhydration and the need for dry weight assessment. Contrib Nephrol. 2008;161:99-107.
Shinohara, et al. Insulin resistance as an independent predictor of cardiovascular mortality in patients with end-stage renal disease. J Am Soc Nephrol. Jul. 2002; 13 (7):1894-900.
Smolle, et al. Intradialytic parenteral nutrition in malnourished patients on chronic haemodialysis therapy. Nephrol Dial Transplant. 1995;10(8):1411-6.
Svensson, et al. Insulin resistance in diabetic nephropathy—cause or consequence? Diabetes Metab Res Rev Sep.-Oct. 2006; 22(5): 401-410.
Warady, et al. KDOQI clinical practice guideline for nutrition in children with CKD: 2008 update. Supplemental to AJKD. Mar. 2008; 53(3), suppl 2.
Wolfsheimer. Problems in diabetes mellitus management. Insulin resistance. Probl Vet Med. Dec. 2, 1990 (4): 591-601.
Wystrychowski, et al. Dry Weight' sine qua non of adequate dialysis. Adv Chronic Kidney Dis. Jul. 2007;14(3):e10-6.
Yokoyama, et al. Dialysis staff encouragement and fluid control adherence inpatients on hemodialysis. Nephrol Nurs J. May-Jun. 2009;36(3):289-97.
Zhang, et al. Kidney Disease and the metabolic syndrome. Am J Med Sci Dec. 2005; 330 (6):319-25.
Canepa, et al. Acute effects of simultaneous intraperitoneal infusion of glucose and amino acids. Kidney Int. May 2001;59(5):1967-73.
Christianson, et al. Determinants of insulin availability in parenteral nutrition solutions. JPEN J Parenter Enteral Nutr. Jan.-Feb. 2006;30(1):6-9.
Garibotto, et al. Acute effects of peritoneal dialysis with dialysates containing dextrose or dextrose and amino acids on muscle protein turnover in patients with chronic renal failure. J Am Soc Nephrol. Mar. 2001;12(3):557-67.
Marshall, et al. Glycemic control in diabetic CAPD patients assessed by continuous glucose monitoring system (CGMS). Kidney Int. Oct. 2003;64(4):1480-6.
Moore, et al. Challenges of providing nutrition support in the outpatient dialysis setting. Nutr Clin Pract. Apr. 2005;20(2):202-12.
Tjiong, et al. Dialysate as food: combined amino acid and glucose dialysate improves protein anabolism in renal failure patients on automated peritoneal dialysis. J Am Soc Nephrol. May 2005;16(5):1486-93. Epub Mar. 30, 2005.
Office action dated Nov. 9, 2011 for U.S. Appl. No. 12/498,773.
U.S. Appl. No. 13/541,604, filed Jul. 3, 2012, Moore.
Brem, et al. Use of amino acid peritoneal dialysate for one year in a child on CCPD. Perit Dial Int. Nov.-Dec. 1996;16(6):634-6.
Chertow, et al. Laboratory Surrogates of Nutritional Status After Administration of Intraperitoneal Amino Acid-Based Solutions in Ambulatory Peritoneal Dialysis Patients. Journal of Renal Nutrition. 1995; 5(3) 116-123.
Delarue, et al. Effects of an amino acid dialysate on leucine metabolism in continuous ambulatory peritoneal dialysis patients. Kidney Int. Nov. 1999;56(5):1934-43.
Dibble, et al. Amino-acid-based continuous ambulatory peritoneal dialysis (CAPD) fluid over twelve weeks: effects on carbohydrate and lipid metabolism. Perit Dial Int. 1990;10(1):71-7.
Dombros, et al. Six month overnight intraperitoneal amino-acid infusion in continuous ambulatory peritoneal dialysis (CAPD) patients—no effect on nutritional status. Perit Dial Int. 1990;10(1):79-84.
Faller, et al. Clinical evaluation of an optimized 1.1% amino-acid solution for peritoneal dialysis. Nephrol Dial Transplant. 1995;10(8):1432-7.
Jones, et al. Treatments of malnutrition with 1.1% amino acid peritoneal dialysis solution: results of a multicenter outpatient study. Am J Kidney Dis. Nov. 1998;32(5):761-9.
Kopple, et al. Treatment of malnourished CAPD patients with an amino acid based dialysate. Kidney Int. Apr. 1995;47(4):1148-57.
Li, et al. A 3-year, prospective, randomized, controlled study on amino acid dialysate in patients on CAPD. American Journal of Kidney Diseases. 2003; 42(1):173-183.
Olszowska, et al. Peritoneal transport in peritoneal dialysis patients using glucose-based and amino acid-based solutions. Perit Dial Int. Sep.-Oct. 2007;27(5):544-53.
Park, et al. Peritoneal transport during dialysis with amino acid-based solutions. Perit Dial Int. 1993;13(4):280-8.
Taylor, et al. Long-term use of 1.1% amino acid dialysis solution in hypoalbuminemic continuous ambulatory peritoneal dialysis patients. Clin Nephrol. Dec. 2002;58(6):445-50.
William, et al. Amino Acid Absorption Following Intraperitoneal Administration in CAPD Patients. Perit Dial Int. Jul./Sep. 1982;2(3):124-130.
Cherry, et al. Efficacy of intradialytic parenteral nutrition in malnourished hemodialysis patients. Am J Health Syst Pharm. Sep. 15, 2002;59(18):1736-41.
Krause, et al. Intradialytic parenteral nutrition in malnourished children treated with hemodialysis. J Ren Nutr. Jan. 2002;12(1):55-9.
McCann, et al. Effect of intradialytic parenteral nutrition on delivered Kt/V. Am J Kidney Dis. Jun. 1999;33(6):1131-5.
Baxter Healthcare Corporation, 20% ProSol—sulfite-free (Amino Acid) Injection, Pharmacy Bulk Package Not for Direct Infusion in Viaflex Plastic Container, Product Information, 1997, 10 pgs.
BC Provincial Guidelines Intradialytic Parenteral Nutrition (IDPN) Mar. 2008, p. 1-21.
Culebras, Jesus M., et al., "Practical aspects of peripheral parenteral nutrition", Curr. Opin. Clin. Nutr. Metab. Care, vol. 7, 2004, pp. 303-307.
Feinfeld, Donald A., et al., "Massive and disproportionate evaluation of blood urea nitrogen in acute azotemia", International Urology and Nephrology, vol. 34 (2002), pp. 143-145.

(56) References Cited

OTHER PUBLICATIONS

Gazitua, Ricardo, et al., "Factors Determining Peripheral Vein Tolerance to Amino Acid Infusions", Arch. Surg., vol. 114 Aug. 1979, pp. 897-900.
Gura, Kathleen M., "Is There Still a Role for Peripheral Parenteral Nutrition", Nutrition in Clinical Practice, vol. 24, No. 6 Dec./Jan. 2009, pp. 709-717.
Klein, Catherine J., et al., "Overfeeding macronutrients to critically ill adults: Metabolic complications", J. Am. Dietetic Assoc., vol. 98, No. 7 Jul. 1998, pp. 795-806.
Lacson, Eduardo, Jr., "Potential Impact of Nutritional Intervention on End-Stae Renal Disease Hospitalization, Death, and Treatment Costs", J. Renal Nutrition, vol. 17, No. 6 Nov. 2007, pp. 363-371.
Lowrie, Edmund G., et al., "Death Risk in Hemodialysis Patients: The Predictive Value of Commonly Measured Variables and an Evaluation of Death Rate Differences Between Facilities", Am. J. Kidney Disease, vol. XV, No. 5 May 1990, pp. 458-482.
Moore, Eileen, et al., "A Superior Proprietary IDPN Formulation for Malnourished Patients with Diabetes", J. Renal Nutrition, vol. 21, Issue 2 Mar. 2011, pp. 205-210.
Mortelmans, Anna Katharina, et al., "Intradialytic Parenteral Nutrition in Malnourished Hemodialysis Patients: A Prospective Long-Term Study", J. Parenteral and Enteral Nutrition, vol. 23, No. 2 (1999), pp. 90-95.
Rollins, Carol J., "Peripheral Parenteral Nutrition", MVI Newslines, 1998, pp: 1-6.
Yarandi, et al., "Amino acid composition in parenteral nutrition: what is the evidence?", Curr. Opin. Clin. Nutr., Metab. Care, Jan. 2001, 14(1):75-82.
Ikizler, T., "The Use and Misuse of Serum Albumin as a Nutritional Market in Kidney Disease", Clin. J. Am. Soc. Nephrol. 7, 2012, pp. 1375-1377.
Nicholson, et al., The role of albumin in critical illness, Br. J. Anaesth, 85(4):599-610 (2000).
Qureshi, et al., "Factors predicting malnutrition in hemodialysis patients: A cross-sectional study", Kidney International, vol. 53 (1998), pp. 773-782.
Ikizler, et al., "Amino acid and albumin losses during hemodialysis", Kidney International, vol. 46 (1994), pp. 830-837.
Fuhrman, et al., "Hepatic Proteins in Nutrition Assessment", J. Am. Diet. Assoc., 2004, vol. 104, pp. 1258-1264.
Kaysen, et al., "Inflammation and distary protein intake exert competing effects on serum albumin and creatinine in hemodialysis patients", Kidney International, vol. 60, 2001, pp. 333-340.
Kim, et al., "Relative contributions of imflammation and inadequate protein intake to hypoalbuminemia in patients on maintenance hemodialysis", Int. Urol. Nephrol., 2012, 45, pp. 215-227.
Bossola, et al., "Variables associated with reduced dietary intake in hemodialysis patients", J. Ren. Nutr., vol. 15, Issue 2, Apr. 2005, pp. 244-252.
Reply to Jul. 25, 2014, Non-Final Office Action in U.S. Appl. No. 12/498,773, filed Aug. 27, 2014.
Tjiong, et al. Peritoneal dialysis with solutions containing amino acids plus glucose promotes protein synthesis during oral feeding. Clin J Am Soc Nephrol. Jan. 2007;2(1):74-80. Epub Nov. 8, 2006.
Beddhu, et al. Inflammation and inverse associations of body mass index and serum creatinine with mortality in hemodialysis patients. J Ren Nutr. Nov. 2007;17(6):372-80.
Gilbertson, et al. Projecting the number of patients with end-stage renal disease in the United States to the year 2015. J Am Soc Nephrol. Dec. 2005;16(12):3736-41. Epub Nov. 2, 2005.
Ikizler. Nutrition support for the chronically wasted or acutely catabolic chronic kidney disease patient. Semin Nephrol. Jan. 2009;29(1):75-84. doi: 10.1016/j.semnephrol.2008.10.011.
Kalantar-Zadeh, et al. Revisiting mortality predictability of serum albumin in the dialysis population: time dependency, longitudinal changes and population-attributable fraction. Nephrol Dial Transplant. 2005; 20:1880-1888.
Kaysen, et al. Trends and outcomes associated with serum albumin concentration among incident dialysis patients in the United States. J Ren Nutr. Jul. 2008;18(4):323-31. doi: 10.1053/j.jrn.2008.04.002.
McCowen, et al. Hyperglycemia and nutrition support: theory and practice. Nutr Clin Pract. Jun. 2004;19(3):235-44.
National Kidney Foundation. K/DOQI Clinical Practice Guidelines for Nutrition in Chronic Renal Failure. Am J Kidney Dis. Jun. 2000;35(6 Suppl 2):S1-140.
Office action dated Aug. 16, 2012 for U.S. Appl. No. 12/498,773.
Powers. Considerations in the use of 3:1 intradialytic parenteral nutrition solutions containing long-chain triglyceride. Contemporary Dialysis and Nephrology. Feb. 1990; 11(2):29-37.
Pupim, et al. Intradialytic parenteral nutrition improves protein and energy homeostasis in chronic hemodialysis patients. J Clin Invest. Aug. 2002;110(4):483-92.
Pupim, et al. Nutritional supplementation acutely increases albumin fractional synthetic rate in chronic hemodialysis patients. J Am Soc Nephrol. Jul. 2004;15(7):1920-6.
Takano. Fluid therapy in diabetic patients. 1994; 168(5):443-447. (in Japanese with machine English translation).
United States Renal Data System. (2007). Incidence and Prevalence. Retrieved Aug. 14, 2008 from www.usrds.org/2007/pdf/02_incid_prev_07.pdf.
United States Renal Data System. (2007). Patient Characteristics. Retrieved Aug. 14, 2008 from www.usrds.org/2007/pdf/03_pt_char_07.pdf.
Waxman, et al. Safety and efficacy of glycerol and amino acids in combination with lipid emulsion for peripheral parenteral nutrition support. JPEN J Parenter Enteral Nutr. Jul.-Aug. 1992;16(4):374-8.

* cited by examiner

| Subject Body Mass | Volume of Dextrose stock solution (70% mass/volume) | Mass Dextrose | Volume of Amino Acid stock solution (20% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 34 - 39 kg | 29 mL | 20 g | 255 mL | 51 g | 334 mL | 272 kcal | D 5.9% AA 15.3% |
| 40 - 44 kg | 33 mL | 23 g | 300 mL | 60 g | 383 mL | 318 kcal | D 6.0% AA 15.7% |
| 45 - 51 kg | 37 mL | 26 g | 340 mL | 68 g | 427 mL | 360 kcal | D 6.1% AA 15.9% |
| 52 - 59 kg | 43 mL | 30 g | 390 mL | 78 g | 483 mL | 414 kcal | D 6.2% AA 16.1% |
| 60 - 69 kg | 50 mL | 35 g | 450 mL | 90 g | 550 mL | 479 kcal | D 6.4% AA 16.4% |
| 70 + kg | 59 mL | 41 g | 525 mL | 105 g | 635 mL | 560 kcal | D 6.5% AA 16.6% |

FIGURE 1

| Subject Body Mass | Week 1 Infusion Rate | Week 2 Infusion Rate |
|---|---|---|
| 34 - 39 kg | 50 mL/hour | 105 mL/hour |
| 40 - 44 kg | 60 mL/hour | 120 mL/hour |
| 45 - 51 kg | 65 mL/hour | 135 mL/hour |
| 52 - 59 kg | 75 mL/hour | 150 mL/hour |
| 60 - 69 kg | 85 mL/hour | 170 mL/hour |
| 70 + kg | 100 mL/hour | 195 mL/hour |

FIGURE 2

| Subject Body Mass | Volume of Dextrose stock solution (70% mass/volume) | Mass Dextrose | Volume of Amino Acid stock solution (15% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 34 - 39 kg | 29 mL | 20 g | 340 mL | 51 g | 419 mL | 272 kcal | D 4.8% AA 12.2% |
| 40 - 44 kg | 33 mL | 23 g | 400 mL | 60 g | 483 mL | 318 kcal | D 4.8% AA 12.4% |
| 45 - 51 kg | 37 mL | 26 g | 453 mL | 68 g | 540 mL | 360 kcal | D 4.8% AA 12.6% |
| 52 - 59 kg | 43 mL | 30 g | 520 mL | 78 g | 613 mL | 414 kcal | D 4.9% AA 12.7% |
| 60 - 69 kg | 50 mL | 35 g | 600 mL | 90 g | 700 mL | 479 kcal | D 5.0% AA 12.9% |
| 70 + kg | 59 mL | 41 g | 700 mL | 105 g | 809 mL | 560 kcal | D 5.1% AA 13.0% |

FIGURE 3

| Subject Body Mass | Week 1 Infusion Rate | Week 2 Infusion Rate |
|---|---|---|
| 34 - 39 kg | 65 mL/hour | 130 mL/hour |
| 40 - 44 kg | 75 mL/hour | 150 mL/hour |
| 45 - 51 kg | 85 mL/hour | 170 mL/hour |
| 52 - 59 kg | 95 mL/hour | 190 mL/hour |
| 60 - 69 kg | 110 mL/hour | 215 mL/hour |
| 70 + kg | 125 mL/hour | 250 mL/hour |

FIGURE 4

| Subject Body Mass | Volume of Dextrose stock solution (70% mass/volume) | Mass Dextrose | Volume of Amino Acid stock solution (20% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 9 - 12 kg | 6 mL | 4 g | 68 mL | 13.5 g | 124 mL | 68 kcal | D 3.2% AA 10.9% |
| 13 - 17 kg | 9 mL | 6 g | 97 mL | 19.5 g | 156 mL | 98 kcal | D 3.8% AA 12.5% |
| 18 - 22 kg | 13 mL | 9 g | 135 mL | 27 g | 198 mL | 139 kcal | D 4.5% AA 13.6% |
| 23 - 27 kg | 16 mL | 11 g | 173 mL | 34.5 g | 239 mL | 175 kcal | D 4.6% AA 14.4% |
| 28 - 33 kg | 20 mL | 14 g | 210 mL | 42 g | 280 mL | 216 kcal | D 5.0% AA 15% |
| 34 - 39 kg | 24 mL | 17 g | 255 mL | 51 g | 329 mL | 262 kcal | D 5.2% AA 15.5% |

FIGURE 5

| Subject Body Mass | Week 1 Infusion Rate | Week 2 Infusion Rate |
|---|---|---|
| 9 - 12 kg | 23 mL/hour | 45 mL/hour |
| 13 - 17 kg | 28 mL/hour | 57 mL/hour |
| 18 - 22 kg | 36 mL/hour | 72 mL/hour |
| 23 - 27 kg | 43 mL/hour | 87 mL/hour |
| 28 - 33 kg | 51 mL/hour | 102 mL/hour |
| 34 - 39 kg | 60 mL/hour | 120 mL/hour |

FIGURE 6

| Subject Body Mass | Volume of Dextrose stock solution (70% mass/volume) | Mass Dextrose | Volume of Amino Acid stock solution (20% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 9 - 12 kg | 7 mL | 5 g | 68 mL | 13.5 g | 125 mL | 71 kcal | D 4.0% AA 10.1% |
| 13 - 17 kg | 11 mL | 8 g | 97 mL | 19.5 g | 158 mL | 105 kcal | D 5.1% AA 12.3% |
| 18 - 22 kg | 15 mL | 10.5 g | 135 mL | 27 g | 200 mL | 144 kcal | D 5.3% AA 13.5% |
| 23 - 27 kg | 19 mL | 13 g | 173 mL | 34.5 g | 242 mL | 182 kcal | D 5.4% AA 14.3% |
| 28 - 33 kg | 23 mL | 16 g | 210 mL | 42 g | 283 mL | 222 kcal | D 5.7% AA 14.8% |
| 34 - 39 kg | 29 mL | 20 g | 255 mL | 51 g | 334 mL | 272 kcal | D 5.9% AA 15.3% |

FIGURE 7

| Subject Body Mass | Week 1 Infusion Rate | Week 2 Infusion Rate |
|---|---|---|
| 9 - 12 kg | 19 mL/hour | 39 mL/hour |
| 13 - 17 kg | 24 mL/hour | 49 mL/hour |
| 18 - 22 kg | 31 mL/hour | 62 mL/hour |
| 23 - 27 kg | 37 mL/hour | 74 mL/hour |
| 28 - 33 kg | 44 mL/hour | 87 mL/hour |
| 34 - 39 kg | 50 mL/hour | 105 mL/hour |

FIGURE 8

| Subject Body Mass | Volume of Dextrose stock solution (70% mass/volume) | Mass Dextrose | Volume of Amino Acid stock solution (20% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 9 - 12 kg | 9 mL | 6 g | 68 mL | 13.5 g | 127 mL | 74 kcal | D 4.7% AA 10.6% |
| 13 - 17 kg | 13 mL | 9 g | 97 mL | 19.5 g | 160 mL | 109 kcal | D 5.6% AA 12.2% |
| 18 - 22 kg | 17 mL | 12 g | 135 mL | 27 g | 202 mL | 149 kcal | D 5.9% AA 13.4% |
| 23 - 27 kg | 22 mL | 15.5 g | 173 mL | 34.5 g | 245 mL | 191 kcal | D 6.3% AA 14.1% |
| 28 - 33 kg | 27 mL | 19 g | 210 mL | 42 g | 287 mL | 233 kcal | D 6.6% AA 14.6% |
| 34 - 39 kg | 33 mL | 23 g | 255 mL | 51gm | 338 mL | 282 kcal | D 6.8% AA 15.1% |

FIGURE 9

| Subject Body Mass | Week 1 Infusion Rate | Week 2 Infusion Rate |
|---|---|---|
| 9 - 12 kg | 17 mL/hour | 34 mL/hour |
| 13 - 17 kg | 21 mL/hour | 43 mL/hour |
| 18 - 22 kg | 27 mL/hour | 54 mL/hour |
| 23 - 27 kg | 33 mL/hour | 65 mL/hour |
| 28 - 33 kg | 38 mL/hour | 77 mL/hour |
| 34 - 39 kg | 45 mL/hour | 90 mL/hour |

FIGURE 10

| Subject Body Mass | Volume of Dextrose stock solution (70% mass/volume) | Mass Dextrose | Volume of Amino Acid stock solution (15% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 9 - 12 kg | 6 mL | 4 g | 90 mL | 13.5 g | 146 mL | 68 kcal | D 2.7% AA 9.2% |
| 13 - 17 kg | 9 mL | 6 g | 130 mL | 19.5 g | 189 mL | 98 kcal | D 3.2% AA 10.3% |
| 18 - 22 kg | 13 mL | 9 g | 180 mL | 27 g | 243 mL | 139 kcal | D 3.7% AA 11.1% |
| 23 - 27 kg | 16 mL | 11 g | 230 mL | 34.5 g | 296 mL | 175 kcal | D 3.7% AA 11.7% |
| 28 - 33 kg | 20 ml | 14 g | 280 mL | 42 g | 350 mL | 216 kcal | D 4.0% AA 12.0% |
| 34 - 39 kg | 24 mL | 17 g | 340 mL | 51 g | 414 mL | 262 kcal | D 4.1% AA 12.4% |

FIGURE 11

| Subject Body Mass | Week 1 Infusion Rate | Week 2 Infusion Rate |
|---|---|---|
| 9 - 12 kg | 27 mL/hour | 53 mL/hour |
| 13 - 17 kg | 34 mL/hour | 69 mL/hour |
| 18 - 22 kg | 44 mL/hour | 88 mL/hour |
| 23 - 27 kg | 54 mL/hour | 108 mL/hour |
| 28 - 33 kg | 64 mL/hour | 127 mL/hour |
| 34 - 39 kg | 75 mL/hour | 151 mL/hour |

FIGURE 12

| Subject Body Mass | Volume of Dextrose stock solution (70% mass/volume) | Mass Dextrose | Volume of Amino Acid stock solution (15% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 9 - 12 kg | 7 mL | 5 g | 90 mL | 13.5 g | 147 mL | 71 kcal | D 3.4% AA 9.2% |
| 13 - 17 kg | 11 mL | 8 g | 130 mL | 19.5 g | 191 mL | 105 kcal | D 4.2% AA 10.2% |
| 18 - 22 kg | 15 mL | 10.5 g | 180 mL | 27 g | 245 mL | 144 kcal | D 4.3% AA 11.0% |
| 23 - 27 kg | 19 mL | 13 g | 230 mL | 34.5 g | 299 mL | 182 kcal | D 4.3% AA 11.5% |
| 28 - 33 kg | 23 mL | 16 g | 280 mL | 42 g | 353 mL | 222 kcal | D 4.5% AA 11.9% |
| 34 - 39 kg | 29 mL | 20 g | 340 mL | 51 g | 419 mL | 272 kcal | D 4.8% AA 12.2% |

FIGURE 13

| Subject Body Mass | Week 1 Infusion Rate | Week 2 Infusion Rate |
|---|---|---|
| 9 - 12 kg | 23 mL/hour | 45 mL/hour |
| 13 - 17 kg | 29 mL/hour | 59 mL/hour |
| 18 - 22 kg | 38 mL/hour | 75 mL/hour |
| 23 - 27 kg | 46 mL/hour | 92 mL/hour |
| 28 - 33 kg | 54 mL/hour | 109 mL/hour |
| 34 - 39 kg | 64 mL/hour | 129 mL/hour |

FIGURE 14

| Subject Body Mass | Volume of Dextrose stock solution (70% mass/volume) | Mass Dextrose | Volume of Amino Acid stock solution (15% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 9 - 12 kg | 9 mL | 6 g | 90 mL | 13.5 g | 149 mL | 74 kcal | D 4.0% AA 9.1% |
| 13 - 17 kg | 13 mL | 9 g | 130 mL | 19.5 g | 193 mL | 109 kcal | D 4.7% AA 10.1% |
| 18 - 22 kg | 17 mL | 12 g | 180 mL | 27 g | 247 mL | 149 kcal | D 4.9% AA 10.9% |
| 23 - 27 kg | 22 mL | 15.5 g | 230 mL | 34.5 g | 302 mL | 191 kcal | D 5.1% AA 11.4% |
| 28 - 33 kg | 27 mL | 19 g | 280 mL | 42 g | 357 mL | 233 kcal | D 5.3% AA 11.8% |
| 34 - 39 kg | 33 mL | 23 g | 340 mL | 51 g | 423 mL | 282 kcal | D 5.4% AA 12.1% |

FIGURE 15

| Subject Body Mass | Week 1 Infusion Rate | Week 2 Infusion Rate |
|---|---|---|
| 9 - 12 kg | 20 mL/hour | 40 mL/hour |
| 13 - 17 kg | 26 mL/hour | 51 mL/hour |
| 18 - 22 kg | 33 mL/hour | 66 mL/hour |
| 23 - 27 kg | 40 mL /hour | 81 mL/hour |
| 28 - 33 kg | 48 mL/hour | 95 mL/hour |
| 34 - 39 kg | 56 mL/hour | 113 mL/hour |

FIGURE 16

| Subject Body Mass | Volume of Dextrose stock solution (70% mass/volume) | Mass Dextrose | Volume of Amino Acid stock solution (20% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 34 - 39 kg | 24 mL | 17 g | 255 mL | 51 g | 329 mL | 262 kcal | D 5.2% AA 15.5% |
| 40 - 44 kg | 29 mL | 20 g | 300 mL | 60 g | 379 mL | 308 kcal | D 5.3% AA 15.8% |
| 45 - 51 kg | 31 mL | 22 g | 340 mL | 68 g | 421 mL | 347 kcal | D 5.2% AA 16.1% |
| 52 - 59 kg | 37 mL | 26 g | 390 mL | 78 g | 477 mL | 400 kcal | D 5.5% AA 16.3% |
| 60 - 69 kg | 43 mL | 30 g | 450 mL | 90 g | 543 mL | 462 kcal | D 5.5% AA 16.6% |
| 70 + kg | 50 mL | 35 g | 525 mL | 105 g | 625 mL | 539 kcal | D 5.6% AA 16.8% |

FIGURE 17

| Subject Body Mass | Week 1 Infusion Rate | Week 2 Infusion Rate |
|---|---|---|
| 34 - 39 kg | 60 mL/hour | 120 mL/hour |
| 40 - 44 kg | 70 mL/hour | 140 mL/hour |
| 45 - 51 kg | 80 mL/hour | 155 mL/hour |
| 52 - 59 kg | 90 mL/hour | 175 mL/hour |
| 60 - 69 kg | 100 mL/hour | 200 mL/hour |
| 70 + kg | 115 mL/hour | 230 mL/hour |

FIGURE 18

| Subject Body Mass | Volume of Dextrose stock solution (70% mass/volume) | Mass Dextrose | Volume of Amino Acid stock solution (20% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 34 - 39 kg | 33 mL | 23 g | 255 mL | 51 g | 338 mL | 282 kcal | D 5.9% AA 15.3% |
| 40 - 44 kg | 39 mL | 27 g | 300 mL | 60 g | 389 mL | 332 kcal | D 6.0% AA 15.7% |
| 45 - 51 kg | 43 mL | 30 g | 340 mL | 68 g | 433 mL | 374 kcal | D 6.1% AA 15.9% |
| 52 - 59 kg | 50 mL | 35 g | 390 mL | 78 g | 490 mL | 431 kcal | D 6.2% AA 16.1% |
| 60 - 69 kg | 59 mL | 41 g | 450 mL | 90 g | 559 mL | 499 kcal | D 6.4% AA 16.4% |
| 70 + kg | 67 mL | 47 g | 525 mL | 105 g | 642 mL | 580 kcal | D 6.5% AA 16.6% |

FIGURE 19

| Subject Body Mass | Week 1 Infusion Rate | Week 2 Infusion Rate |
|---|---|---|
| 34 - 39 kg | 45 mL/hour | 90 mL/hour |
| 40 - 44 kg | 55 mL/hour | 105 mL/hour |
| 45 - 51 kg | 60 mL/hour | 115 mL/hour |
| 52 - 59 kg | 65 mL/hour | 130 mL/hour |
| 60 - 69 kg | 75 mL/hour | 150 mL/hour |
| 70 + kg | 85 mL/hour | 175 mL/hour |

FIGURE 20

| Subject Body Mass | Volume of Dextrose stock solution (70% mass/volume) | Mass Dextrose | Volume of Amino Acid stock solution (15% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 34 - 39 kg | 24 mL | 17 g | 340 mL | 51 g | 414 mL | 262 kcal | D 4.1% AA 12.3% |
| 40 - 44 kg | 29 mL | 20 g | 400 mL | 60 g | 479 mL | 308 kcal | D 4.2% AA 12.5% |
| 45 - 51 kg | 31 mL | 22 g | 455 mL | 68 g | 536 mL | 347 kcal | D 4.1% AA 12.7% |
| 52 - 59 kg | 37 mL | 26 g | 520 mL | 78 g | 607 mL | 400 kcal | D 4.3% AA 12.9% |
| 60 - 69 kg | 43 mL | 30 g | 600 mL | 90 g | 693 mL | 462 kcal | D 4.3% AA 13.0% |
| 70 + kg | 50 mL | 35 g | 700 mL | 105 g | 800 mL | 539 kcal | D 4.4% AA 13.1% |

FIGURE 21

| Subject Body Mass | Week 1 Infusion Rate | Week 2 Infusion Rate |
|---|---|---|
| 34 - 39 kg | 75 mL/hour | 150 mL/hour |
| 40 - 44 kg | 90 mL/hour | 175 mL/hour |
| 45 - 51 kg | 100 mL/hour | 195 mL/hour |
| 52 - 59 kg | 110 mL/hour | 220 mL/hour |
| 60 - 69 kg | 130 mL/hour | 255 mL/hour |
| 70 + kg | 145 mL/hour | 290 mL/hour |

FIGURE 22

| Subject Body Mass | Volume of Dextrose stock solution (70% mass/volume) | Mass Dextrose | Volume of Amino Acid stock solution (15% mass/volume) | Mass Amino Acids | Total Volume (Including 50 mL fill) | Total Energy | Final mass/volume concentration of dextrose (D) and amino acids (AA) |
|---|---|---|---|---|---|---|---|
| 34 - 39 kg | 33 mL | 23 g | 340 mL | 51 g | 423 mL | 282 kcal | D 5.4% AA 12.1% |
| 40 - 44 kg | 39 mL | 27 g | 400 mL | 60 g | 489 mL | 332 kcal | D 5.5% AA 12.3% |
| 45 - 51 kg | 43 mL | 30 g | 455 mL | 68 g | 548 mL | 374 kcal | D 5.5% AA 12.4% |
| 52 - 59 kg | 50 mL | 35 g | 520 mL | 78 g | 620 mL | 431 kcal | D 5.6% AA 12.6% |
| 60 - 69 kg | 59 mL | 41 g | 600 mL | 90 g | 709 mL | 499 kcal | D 5.8% AA 12.7% |
| 70 + kg | 67 mL | 47 g | 700 mL | 105 g | 817 mL | 580 kcal | D 5.8% AA 12.9% |

FIGURE 23

| Subject Body Mass | Week 1 Infusion Rate | Week 2 Infusion Rate |
|---|---|---|
| 34 - 39 kg | 60 mL/hour | 115 mL/hour |
| 40 - 44 kg | 65 mL/hour | 130 mL/hour |
| 45 - 51 kg | 75 mL/hour | 145 mL/hour |
| 52 - 59 kg | 85 mL/hour | 165 mL/hour |
| 60 - 69 kg | 95 mL/hour | 190 mL/hour |
| 70 + kg | 110 mL/hour | 220 mL/hour |

FIGURE 24

| Subject Body Mass | Volume of Dextrose stock solution (70% mass/volume) | Mass Dextrose | Volume of Amino Acid stock solution (20% mass/volume) | Mass Amino Acids | Volume of Lipid stock mixture (20% mass/volume) | Mass Lipids | Total Volume (Including 50 mL fill) | Total Energy | Final mass/volume conc.of dextrose (D), amino acids (AA), and Lipids |
|---|---|---|---|---|---|---|---|---|---|
| 34 - 39 kg | 24 mL | 17 g | 255 mL | 51 g | 43 mL | 8.6 g | 372 mL | 348 kcal | D 4.6% AA 13.7% Lipid 2.3% |
| 40 - 44 kg | 29 mL | 20 g | 300 mL | 60 g | 51 mL | 10.2 g | 430 mL | 410 kcal | D 4.7% AA 14.0% Lipid 2.4% |
| 45 - 51 kg | 31 mL | 22 g | 340 mL | 68 g | 56 mL | 11.2 g | 477 mL | 459 kcal | D 4.6% AA 14.2% Lipid 2.3% |
| 52 - 59 kg | 37 mL | 26 g | 390 mL | 78 g | 66 mL | 13.2 g | 543 mL | 532 kcal | D 4.8% AA 14.4% Lipid 2.4% |
| 60 - 69 kg | 43 mL | 30 g | 450 mL | 90 g | 76 mL | 15.2 g | 619 mL | 614 kcal | D 4.8% AA 14.5% Lipid 2.5% |
| 70 + kg | 50 mL | 35 g | 525 mL | 105 g | 89 mL | 17.8 g | 715 mL | 717 kcal | D 4.9% AA 14.7% Lipid 2.5% |

FIGURE 25

| Subject Body Mass | Week 1 Infusion Rate | Week 2 Infusion Rate | Week 3 Infusion Rate |
|---|---|---|---|
| 34 - 39 kg | 60 mL/hour | 120 mL/hour | 135 mL/hour |
| 40 - 44 kg | 70 mL/hour | 140 mL/hour | 160 mL/hour |
| 45 - 51 kg | 80 mL/hour | 155 mL/hour | 175 mL/hour |
| 52 - 59 kg | 90 mL/hour | 175 mL/hour | 200 mL/hour |
| 60 - 69 kg | 100 mL/hour | 200 mL/hour | 225 mL/hour |
| 70 + kg | 115 mL/hour | 230 mL/hour | 260 mL/hour |

FIGURE 26

| Subject Body Mass | Volume of Dextrose stock solution (70% mass/volume) | Mass Dextrose | Volume of Amino Acid stock solution (20% mass/volume) | Mass Amino Acids | Volume of Lipid stock mixture (20% mass/volume) | Mass Lipids | Total Volume (Including 50 mL fill) | Total Energy | Final mass/volume conc. of dextrose (D), amino acids (AA), and Lipids |
|---|---|---|---|---|---|---|---|---|---|
| 34 - 39 kg | 33 mL | 23 g | 255 mL | 51 g | 59 mL | 11.8 g | 397 mL | 400 kcal | D 5.8% AA 12.8% Lipid 3.0% |
| 40 - 44 kg | 39 mL | 27 g | 300 mL | 60 g | 69 mL | 13.8 g | 458 mL | 470 kcal | D 5.9% AA 13.1% Lipid 3.0% |
| 45 - 51 kg | 43 mL | 30 g | 340 mL | 68 g | 76 mL | 15.2 g | 509 mL | 526 kcal | D 5.9% AA 13.4% Lipid 3.0% |
| 52 - 59 kg | 50 mL | 35 g | 390 mL | 78 g | 89 mL | 17.8 g | 579 mL | 609 kcal | D 6.0% AA 13.5% Lipid 3.1% |
| 60 - 69 kg | 59 mL | 41 g | 450 mL | 90 g | 105 mL | 21 g | 664 mL | 709 kcal | D 6.2% AA 13.6% Lipid 3.2% |
| 70 + kg | 67 mL | 47 g | 525 mL | 105 g | 120 mL | 24 g | 762 mL | 820 kcal | D 6.2% AA 13.8% Lipid 3.1% |

FIGURE 27

| Subject Body Mass | Week 1 Infusion Rate | Week 2 Infusion Rate | Week 3 Infusion Rate |
|---|---|---|---|
| 34 - 39 kg | 45 mL/hour | 90 mL/hour | 110 mL/hour |
| 40 - 44 kg | 55 mL/hour | 105 mL/hour | 125 mL/hour |
| 45 - 51 kg | 60 mL/hour | 115 mL/hour | 135 mL/hour |
| 52 - 59 kg | 65 mL/hour | 130 mL/hour | 155 mL/hour |
| 60 - 69 kg | 75 mL/hour | 150 mL/hour | 180 mL/hour |
| 70 + kg | 85 mL/hour | 175 mL/hour | 205 mL/hour |

FIGURE 28

| Subject Body Mass | Volume of Dextrose stock solution (70% mass/volume) | Mass Dextrose | Volume of Amino Acid stock solution (20% mass/volume) | Mass Amino Acids | Volume of Lipid stock mixture (20% mass/volume) | Mass Lipids | Total Volume (Including 50 mL fill) | Total Energy | Final mass/volume conc.of dextrose (D), amino acids (AA), and Lipids |
|---|---|---|---|---|---|---|---|---|---|
| 34 - 39 kg | 29 mL | 20 g | 255 mL | 51 g | 51 mL | 10.2 g | 385 mL | 374 kcal | D 5.2% AA 13.2% Lipid 2.6% |
| 40 - 44 kg | 33 mL | 23 g | 300 mL | 60 g | 59 mL | 11.8 g | 442 mL | 436 kcal | D 5.2% AA 13.6% Lipid 2.7% |
| 45 - 51 kg | 37 mL | 26 g | 340 mL | 68 g | 66 mL | 13.3 g | 493 mL | 492 kcal | D 5.3% AA 13.8% Lipid 2.7% |
| 52 - 59 kg | 43 mL | 30 g | 390 mL | 78 g | 76 mL | 15.2 g | 559 mL | 566 kcal | D 5.4% AA 14.0% Lipid 2.7% |
| 60 - 69 kg | 50 mL | 35 g | 450 mL | 90 g | 89 mL | 17.8 g | 639 mL | 657 kcal | D 5.5% AA 14.1% Lipid 2.8% |
| 70 + kg | 59 mL | 41 g | 525 mL | 105 g | 105 mL | 21 g | 739 mL | 770 kcal | D 5.5% AA 14.2% Lipid 2.8% |

FIGURE 29

| Subject Body Mass | Week 1 Infusion Rate | Week 2 Infusion Rate | Week 3 Infusion Rate |
|---|---|---|---|
| 34 - 39 kg | 55 mL/hour | 105 mL/hour | 120 mL/hour |
| 40 - 44 kg | 60 mL/hour | 120 mL/hour | 140 mL/hour |
| 45 - 51 kg | 65 mL/hour | 135 mL/hour | 155 mL/hour |
| 52 - 59 kg | 75 mL/hour | 150 mL/hour | 175 mL/hour |
| 60 - 69 kg | 85 mL/hour | 170 mL/hour | 200 mL/hour |
| 70 + kg | 100 mL/hour | 195 mL/hour | 230 mL/hour |

FIGURE 30

| Subject Body Mass | Volume of Dextrose stock solution (70% mass/ volume) | Mass Dextrose | Volume of Amino Acid stock solution (15% mass/ volume) | Mass Amino Acids | Volume of Lipid stock mixture (20% mass/ volume) | Mass Lipids | Total Volume (Including 50 mL fill) | Total Energy | Final mass/ volume conc.of dextrose (D), amino acids (AA), and Lipids |
| --- | --- | --- | --- | --- | --- | --- | --- | --- | --- |
| 34 - 39 kg | 24 mL | 17 g | 340 mL | 51 g | 43 mL | 8.6 g | 457 mL | 348 kcal | D 3.7% AA 11.2% Lipid 1.9% |
| 40 - 44 kg | 29 mL | 20 g | 400 mL | 60 g | 51 mL | 10.2 g | 530 mL | 410 kcal | D 3.8% AA 11.3% Lipid 1.9% |
| 45 - 51 kg | 31 mL | 22 g | 453 mL | 68 g | 56 mL | 11.2 g | 590 mL | 459 kcal | D 3.7% AA 11.5% Lipid 1.9% |
| 52 - 59 kg | 37 mL | 26 g | 520 mL | 78 g | 66 mL | 13.2 g | 673 mL | 532 kcal | D 3.9% AA 11.6% Lipid 2.0% |
| 60 - 69 kg | 43 mL | 30 g | 600 mL | 90 g | 76 mL | 15.2 g | 769 mL | 614 kcal | D 3.9% AA 11.7% Lipid 2.0% |
| 70 + kg | 50 mL | 35 g | 700 mL | 105 g | 89 mL | 17.8 g | 889 mL | 717 kcal | D 3.9% AA 11.8% Lipid 2.0% |

FIGURE 31

| Subject Body Mass | Week 1 Infusion Rate | Week 2 Infusion Rate | Week 3 Infusion Rate |
|---|---|---|---|
| 34 - 39 kg | 75 mL/hour | 150 mL/hour | 170 mL/hour |
| 40 - 44 kg | 90 mL/hour | 175 mL/hour | 195 mL/hour |
| 45 - 51 kg | 100 mL/hour | 195 mL/hour | 215 mL/hour |
| 52 - 59 kg | 110 mL/hour | 220 mL/hour | 245 mL/hour |
| 60 - 69 kg | 130 mL/hour | 255 mL/hour | 280 mL/hour |
| 70 + kg | 145 mL/hour | 290 mL/hour | 325 mL/hour |

FIGURE 32

| Subject Body Mass | Volume of Dextrose stock solution (70% mass/volume) | Mass Dextrose | Volume of Amino Acid stock solution (15% mass/volume) | Mass Amino Acids | Volume of Lipid stock mixture (20% mass/volume) | Mass Lipids | Total Volume (Including 50 mL fill) | Total Energy | Final mass/volume conc. of dextrose (D), amino acids (AA), and Lipids |
|---|---|---|---|---|---|---|---|---|---|
| 34 - 39 kg | 33 mL | 23 g | 340 mL | 51 g | 59 mL | 11.8 g | 482 mL | 400 kcal | D 4.8% AA 10.6% Lipid 2.4% |
| 40 - 44 kg | 39 mL | 27 g | 400 mL | 60 g | 69 mL | 13.8 g | 558 mL | 470 kcal | D 4.8% AA 10.8% Lipid 2.5% |
| 45 - 51 kg | 43 mL | 30 g | 453 mL | 68 g | 76 mL | 15.2 g | 622 mL | 526 kcal | D 4.8% AA 10.9% Lipid 2.4% |
| 52 - 59 kg | 50 mL | 35 g | 520 mL | 78 g | 89 mL | 17.8 g | 709 mL | 609 kcal | D 4.9% AA 11.0% Lipid 2.6% |
| 60 - 69 kg | 59 mL | 41 g | 600 mL | 90 g | 105 mL | 21 g | 814 mL | 709 kcal | D 5.0% AA 11.1% Lipid 2.6% |
| 70 + kg | 67 mL | 47 g | 700 mL | 105 g | 120 mL | 24 g | 937 mL | 820 kcal | D 5.0% AA 11.2% Lipid 2.6% |

FIGURE 33

| Subject Body Mass | Week 1 Infusion Rate | Week 2 Infusion Rate | Week 3 Infusion Rate |
|---|---|---|---|
| 34 - 39 kg | 60 mL/hour | 115 mL/hour | 130 mL/hour |
| 40 - 44 kg | 65 mL/hour | 130 mL/hour | 150 mL/hour |
| 45 - 51 kg | 75 mL/hour | 145 mL/hour | 165 mL/hour |
| 52 - 59 kg | 85 mL/hour | 165 mL/hour | 190 mL/hour |
| 60 - 69 kg | 95 mL/hour | 190 mL/hour | 220 mL/hour |
| 70 + kg | 110 mL/hour | 220 mL/hour | 250 mL/hour |

FIGURE 34

| Subject Body Mass | Volume of Dextrose stock solution (70% mass/volume) | Mass Dextrose | Volume of Amino Acid stock solution (15% mass/volume) | Mass Amino Acids | Volume of Lipid stock mixture (20% mass/volume) | Mass Lipids | Total Volume (Including 50 mL fill) | Total Energy | Final mass/volume conc. of dextrose (D), amino acids (AA), and Lipids |
|---|---|---|---|---|---|---|---|---|---|
| 34 - 39 kg | 29 mL | 20 g | 340 mL | 51 g | 51 mL | 10.2 g | 470 mL | 374 kcal | D 4.3% AA 10.9% Lipid 2.2% |
| 40 - 44 kg | 33 mL | 23 g | 400 mL | 60 g | 59 mL | 11.8 g | 542 mL | 436 kcal | D 4.2% AA 11.1% Lipid 2.2% |
| 45 - 51 kg | 37 mL | 26 g | 453 mL | 68 g | 66 mL | 13.2 g | 606 mL | 492 kcal | D 4.3% AA 11.2% Lipid 2.2% |
| 52 - 59 kg | 43 mL | 30 g | 520 mL | 78 g | 76 mL | 15.2 g | 689 mL | 566 kcal | D 4.4% AA 11.3% Lipid 2.2% |
| 60 - 69 kg | 50 mL | 35 g | 600 mL | 90 g | 89 mL | 17.8 g | 789 mL | 657 kcal | D 4.4% AA 11.4% Lipid 2.3% |
| 70 + kg | 59 mL | 41 g | 700 mL | 105 g | 105 mL | 21 g | 914 mL | 770 kcal | D 4.5% AA 11.5% Lipid 2.3% |

FIGURE 35

| Subject Body Mass | Week 1 Infusion Rate | Week 2 Infusion Rate | Week 3 Infusion Rate |
|---|---|---|---|
| 34 - 39 kg | 65 mL/hour | 130 mL/hour | 145 mL/hour |
| 40 - 44 kg | 75 mL/hour | 150 mL/hour | 170 mL/hour |
| 45 - 51 kg | 85 mL/hour | 170 mL/hour | 190 mL/hour |
| 52 - 59 kg | 95 mL/hour | 190 mL/hour | 215 mL/hour |
| 60 - 69 kg | 110 mL/hour | 215 mL/hour | 245 mL/hour |
| 70 + kg | 125 mL/hour | 250 mL/hour | 285 mL/hour |

FIGURE 36

NUTRITIVE COMPOSITIONS AND METHODS OF USING SAME

This application is a continuation-in-part of U.S. application Ser. No. 12/498,773, filed on Jul. 7, 2009, which claims priority to U.S. Provisional App. No. 61/078,636, filed on Jul. 7, 2008, and U.S. Provisional App. No. 61/080,567, filed on Jul. 14, 2008, and claims priority under 35 U.S.C. §120. This application also claims priority to U.S. Provisional App. No. 61/292,139, filed on Jan. 4, 2010, and U.S. Provisional App. No. 61/292,806, filed on Jan. 6, 2010. This application is related to International Patent App. No. PCT/US09/49800, filed on Jul. 7, 2009, which claims priority to U.S. Provisional App. No. 61/078,636, filed on Jul. 7, 2008, and U.S. Provisional App. No. 61/080,567, filed on Jul. 14, 2008. Each of the above applications is incorporated by reference herein in its entirety.

FIELD OF THE INVENTION

The invention provides nutrition supplement compositions for subjects receiving dialysis treatment and methods of using the nutrition supplement compositions. In some embodiments the nutrition supplement compositions comprise reduced levels of carbohydrates and lower volume to reduce complications in subjects. In some cases, the subjects are diabetic or suffer from other glucose management related pathologies, or subjects benefit from strict fluid management.

BACKGROUND OF THE INVENTION

Severe malnutrition remains a problem for subjects receiving maintenance hemodialysis (MHD). Dialysis subjects often have poor appetites and low energy. This malnutrition is reflected in low serum albumin concentrations, a strong predictor of increased morbidity and mortality. (Moore and Lindenfield, *Support Line* 29(5):7-16 (October 2007)). Subjects are often treated using diet liberalization, oral supplements and enteral feeding. When these methods are not effective intradialytic parenteral nutrition (IDPN) can be utilized for more aggressive nutrition repletion efforts.

IDPN is infused during the hemodialysis procedure. IDPN has been used for decades and has resulted in weight gain and improved protein levels in subjects. (U.S. Publication No. 2005/0148647). During IDPN infusion into a subject, the subject's blood glucose must be monitored to avoid problems, such as hyperglycemia and hypoglycemia. Serum bicarbonate and carbon dioxide levels must also be monitored to check for acidosis caused by administration of amino acids.

IDPN is usually administered in one liter of solution, and occasionally micronutrients, like vitamins and minerals are co-administered in or with IDPN. Literature suggests that IDPN is effective in decreasing morbidity and mortality in hemodialysis (MHD) subjects, leads to increased levels of serum albumin and creatinine levels, and increased body weight. (Moore and Celano, *Nutrition in Clinical Practice*, 20(2):202-212 (2005)). Hypoglycemia is another potential dangerous result of the administration of insulin during IDPN with symptoms of nervousness, sweating, intense hunger, trembling, weakness, palpitations, and trouble speaking.

Problems associated with IDPN include hyperglycemia, complications in subjects with insulin resistance or other problems associated with glucose management, as well as complications in subjects who require strict fluid management. The glucose concentrations administered with IDPN can cause hyperglycemia and hypoglycemia in some subjects. The administration of insulin can sometimes successfully treat this hyperglycemia, but some subjects demonstrate insulin resistance, and might not respond to insulin treatment. (Goldstein and Strom, *Journal of Renal Nutrition* 1(1):9-22 (January 1991)). Hyperglycemia is a major barrier to effective nutrition support even outside the context of hemodialysis. Many studies report associations between hyperglycemia and increased morbidity and mortality. (McCowen and Bistrian, *Nutrition in Clinical Practice*, 19(3):235-244 (June 2004)). Moreover, the amount of fluid in typical IDPN treatment is a barrier to use in subjects with strict fluid management.

SUMMARY OF THE INVENTION

In one aspect the invention provides a sterile aqueous composition for parenteral administration comprising between 2 and 26 g of dextrose; and between 12 and 45 g of amino acids; wherein the dosage form is an aqueous composition has a volume less than 450 mL.

In another aspect the invention provides a sterile aqueous composition for parenteral administration comprising between 2 and 26 g of dextrose; between 12 and 45 g of amino acids; and between 8 and 25 g of lipids. In one embodiment the amino acids comprise seventeen amino acids. In another embodiment the seventeen amino acids are lysine, leucine, phenylalanine, valine, histidine, isoleucine, methionine, threonine, tryptophan, tlanine, arginine, glycine, proline, glutamic acid, serine, aspartic acid, and tyrosine. In another embodiment an aqueous composition further comprises lipids. In another embodiment the lipids are present in the aqueous composition in an amount between 5 to 30% mass/volume. In another embodiment the lipids are present in the aqueous composition in an amount less than 5% mass/volume. In another embodiment the lipids are present in the aqueous composition in an amount between 5 to 30% mass/volume. In another embodiment the lipids are present in the aqueous composition in an amount less than 5% mass/volume. In another embodiment an aqueous composition further comprises micronutrients. In another embodiment the composition is contained within a sterile container suitable for parenteral administration of the aqueous composition.

In another aspect the invention provides a method for treating malnutrition in a hemodialysis subject in need thereof comprising formulating an aqueous composition comprising between 1 and 10% mass/volume of dextrose and 7 to 20% mass/volume of amino acids based on a body mass measurement of the subject and the intended duration of the hemodialysis and parenterally administering said aqueous composition in conjunction with the hemodialysis. In one embodiment treating the malnutrition comprises raising said subject's albumin levels by 0.2-0.4 g/dL in 1 to 3 months. In another embodiment treating the malnutrition comprises raising said subject's albumin levels by 0.2-0.4 g/dL in 1 to 6 months. In another embodiment treating the malnutrition comprises raising said subject's albumin levels by 0.2-0.4 g/dL in 1 to 12 months. In another embodiment treating the malnutrition comprises raising said subject's albumin levels by 0.2-0.4 g/dL in 1 to 3 years. In another embodiment treating the malnutrition comprises raising said subject's albumin levels by 0.2-0.4 g/dL in 1 to 5 years. In another embodiment treating the malnutrition comprises raising said subject's albumin levels by 0.2-0.4 g/dL in 1 to 10 years. In another embodiment treating the malnutrition comprises raising said subject's albumin levels to 3.8 g/dL. In another embodiment the aqueous composition comprises between 2 and 7% dextrose and between 9 and 16% amino acids. In another embodiment the aqueous composition lacks lipids. In another embodiment the aqueous composition comprises lipids. In another embodiment hemodialysis is performed with a Fresenius 2008 series, a B.Braun Dialog+, a Gambro Phoenix System, a Redy 2000, a Baxter SPS550/1550, an Althin 1000, an Althin Altratouch 1000, an Althin Tina, a Meridian, an Aurora system 1000, a NxStage System, or a Fresinius 2008K dialysis machine. In another embodiment the aqueous composition is introduced into a hemodialysis machine by a venous drip chamber. In another embodiment the subject is administered said aqueous composition 1-5 times per week. In another embodiment the subject is administered said aqueous composition each time said subject undergoes dialysis for 1-3 months. In another embodiment the subject is administered said aqueous composition each time said subject undergoes dialysis for 1-6 months. In another embodiment the subject is administered said aqueous composition each time said subject undergoes dialysis for 1-12 months. In another embodiment the subject is administered said aqueous composition each time said subject undergoes dialysis for 1-3 years. In another embodiment the subject is administered said aqueous composition each time said subject undergoes dialysis for 1-5 years. In another embodiment the subject is administered said aqueous composition each time said subject undergoes dialysis for 1-10 years. In another embodiment the subject's albumin levels increase by 0.2 g/deciliter within three months after the first administration of said composition. In another embodiment the subject's albumin levels increase by 0.4 g/deciliter within three months after the first administration of said composition. In another embodiment the subject is a child. In another embodiment the subject is under about 8 years old. In another embodiment the subject is under about 12 years old. In another embodiment the subject is from about 1 to about 18 years old. In another embodiment the subject is from about 5 to about 12 years old. In another embodiment the composition comprises less than 430 mls in volume. In another embodiment the subject is older than 18 years old. In another embodiment the subject has reduced side effects associated with infusion of an aqueous composition during dialysis. In another embodiment the side effects are dyspnea, increased respiratory rate, rhonchi, edema, hypertension, hernia, or anxiety. In another embodiment the subject has reduced occurrence of hyperglycemia during dialysis. In another embodiment the subject has reduced fluid accumulation during dialysis. In another embodiment the subject has diabetes.

In another aspect, the invention provides a method for treating malnutrition in a hemodialysis subject in need thereof comprising formulating an aqueous composition comprising between 1 and 10% mass/volume of dextrose, 7 to 20% mass/volume of amino acids and less than 5% mass/volume of lipids based on a body mass measurement of the subject and parenterally administering said aqueous composition in conjunction with the hemodialysis.

In another aspect, the invention provides a method for treating malnutrition in a hemodialysis pediatric subject in need thereof comprising formulating an aqueous composition comprising between 1 and 10% mass/volume of dextrose and 7 to 20% mass/volume of amino acids based on a body mass measurement of the subject and parenterally administering said aqueous composition in conjunction with the hemodialysis. In another embodiment the subject has a body mass less than 34 kg.

In another aspect, the invention provides a method of treating malnutrition in a pediatric hemodialysis subject, the method comprising parenterally administering a sterile aqueous composition to the subject, the composition comprising: an amount of dextrose from about 4 g to about 19 g and an amount of amino acids from about 13.5 g to about 42 g in a total volume of about 124 mL to about 357 mL, wherein the subject has a body mass of from 9 kg to 33 kg, wherein the administering is done at an infusion rate of from 17 mL/hour to 127 mL/hour.

In one embodiment, the invention provides a method of treating malnutrition in a subject, the method comprising parenterally administering a sterile aqueous composition to the subject, the composition comprising: an amount of dextrose from about 17 g to about 47 g and an amount of amino acids from about 51 g to about 105 g in a total volume of about 329 mL to about 817 mL, wherein the subject has a body mass of from 34 kg to at least 70 kg, wherein the administering is done at an infusion rate of from 45 mL/hour to 290 mL/hour.

In another aspect, the invention provides a method of treating malnutrition in a hemodialysis subject, the method comprising parenterally administering a sterile aqueous composition to the subject, the composition comprising: an amount of dextrose from about 17 g to about 47 g, an amount of amino acids from about 51 g to about 105 g, and an amount of lipids from 8.6 g about to about 24 in a total volume of about 372 mL to about 937 mL, wherein the subject has a body mass of at least 34 kg, wherein the administering is done at an infusion rate of from 45 mL/hour to 325 mL/hour.

BRIEF DESCRIPTION OF THE FIGURES

FIG. 1 describes IDPN compositions administrable over an infusion time of 3.25-3.5 hours. The formulation of the IDPN compositions vary by the body mass of the subject to which the IDPN composition is administered.

FIG. 2 describes the rates at which an IDPN composition of FIG. 1 is administered during the first and second weeks of therapy.

FIG. 3 describes IDPN compositions administrable over an infusion time of 3.25-3.5 hours. The formulation of the IDPN compositions vary by the body mass of the subject to which the IDPN composition is administered.

FIG. 4 describes the rates at which an IDPN composition of FIG. 3 is administered during the first and second weeks of therapy.

FIG. 5 describes IDPN compositions administrable over an infusion time of 2.75-3.0 hours. The formulation of the IDPN compositions vary by the body mass of the subject to which the IDPN composition is administered.

FIG. 6 describes the rates at which an IDPN composition of FIG. 5 is administered during the first and second weeks of therapy.

FIG. 7 describes IDPN compositions administrable over an infusion time of 3.25-3.5 hours. The formulation of the IDPN compositions vary by the body mass of the subject to which the IDPN composition is administered.

FIG. 8 describes the rates at which an IDPN composition of FIG. 7 is administered during the first and second weeks of therapy.

FIG. 9 describes IDPN compositions administrable over an infusion time of 3.75-4.0 hours. The formulation of the IDPN compositions vary by the body mass of the subject to which the IDPN composition is administered.

FIG. 10 describes the rates at which an IDPN composition of FIG. 9 is administered during the first and second weeks of therapy.

FIG. 11 describes IDPN compositions administrable over an infusion time of 2.75-3.0 hours. The formulation of the IDPN compositions vary by the body mass of the subject to which the IDPN composition is administered.

FIG. 12 describes the rates at which an IDPN composition of FIG. 11 is administered during the first and second weeks of therapy.

FIG. 13 describes IDPN compositions administrable over an infusion time of 3.25-3.5 hours. The formulation of the IDPN compositions vary by the body mass of the subject to which the IDPN composition is administered.

FIG. 14 describes the rates at which an IDPN composition of FIG. 13 is administered during the first and second weeks of therapy.

FIG. 15 describes IDPN compositions administrable over an infusion time of 3.75-4.0 hours. The formulation of the IDPN compositions vary by the body mass of the subject to which the IDPN composition is administered.

FIG. 16 describes the rates at which an IDPN composition of FIG. 15 is administered during the first and second weeks of therapy.

FIG. 17 describes IDPN compositions administrable over a diffusion time of 2.75-3.0 hours. The formulation of the IDPN compositions vary by the body mass of the subject to which the IDPN composition is administered.

FIG. 18 describes the rates at which an IDPN composition of FIG. 17 is administered during the first and second weeks of therapy.

FIG. 19 describes IDPN compositions administrable over a diffusion time of 3.75-4.0 hours. The formulation of the IDPN compositions vary by the body mass of the subject to which the IDPN composition is administered.

FIG. 20 describes the rates at which an IDPN composition of FIG. 19 is administered during the first and second weeks of therapy.

FIG. 21 describes IDPN compositions administrable over a diffusion time of 2.75-3.0 hours. The formulation of the IDPN compositions vary by the body mass of the subject to which the IDPN composition is administered.

FIG. 22 describes the rates at which an IDPN composition of FIG. 21 is administered during the first and second weeks of therapy.

FIG. 23 describes IDPN compositions administrable over a diffusion time of 3.75-4.0 hours. The formulation of the IDPN compositions vary by the body mass of the subject to which the IDPN composition is administered.

FIG. 24 describes the rates at which an IDPN composition of FIG. 23 is administered during the first and second weeks of therapy.

FIG. 25 describes lipid-containing IDPN compositions administrable over a diffusion time of 2.75-3.0 hours. The formulation of the IDPN compositions vary by the body mass of the subject to which the IDPN composition is administered.

FIG. 26 describes the rates at which an IDPN composition of FIG. 25 is administered during the first, second, and third weeks of therapy.

FIG. 27 describes lipid-containing IDPN compositions administrable over a diffusion time of 3.75-4.0 hours. The formulation of the IDPN compositions vary by the body mass of the subject to which the IDPN composition is administered.

FIG. 28 describes the rates at which an IDPN composition of FIG. 27 is administered during the first, second, and third weeks of therapy.

FIG. 29 describes lipid-containing IDPN compositions administrable over a diffusion time of 3.25-3.5 hours. The formulation of the IDPN compositions vary by the body mass of the subject to which the IDPN composition is administered.

FIG. 30 describes the rates at which an IDPN composition of FIG. 29 is administered during the first, second, and third weeks of therapy.

FIG. 31 describes lipid-containing IDPN compositions administrable over a diffusion time of 2.75-3.0 hours. The formulation of the IDPN compositions vary by the body mass of the subject to which the IDPN composition is administered.

FIG. 32 describes the rates at which an IDPN composition of FIG. 31 is administered during the first, second, and third weeks of therapy.

FIG. 33 describes lipid-containing IDPN compositions administrable over a diffusion time of 3.75-4.0 hours. The formulation of the IDPN compositions vary by the body mass of the subject to which the IDPN composition is administered.

FIG. 34 describes the rates at which an IDPN composition of FIG. 33 is administered during the first, second, and third weeks of therapy.

FIG. 35 describes lipid-containing IDPN compositions administrable over a diffusion time of 3.25-3.5 hours. The formulation of the IDPN compositions vary by the body mass of the subject to which the IDPN composition is administered.

FIG. 36 describes the rates at which an IDPN composition of FIG. 35 is administered during the first, second, and third weeks of therapy.

DETAILED DESCRIPTION

Figure 37:
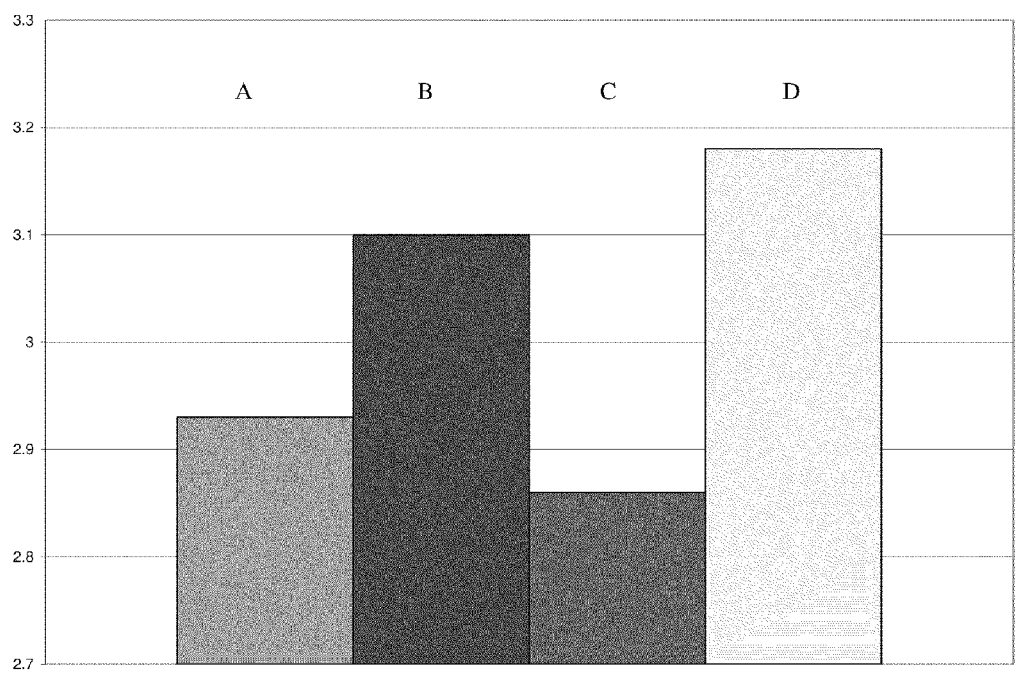
FIG. 37 illustrates the serum albumin levels in diabetic subjects of a study described in Example 22. A) describes Group I subjects' baseline mean levels. B) describes Group I subjects' 3 month mean levels. C) describes Group II subjects' baseline mean levels. D) describes Group II subjects' 3 month mean levels. The y-axis describes serum albumin levels in g/L.

As used herein, the term "amino acid" refers to any of the twenty genetically-encoded L-a-amino acids unless indicated otherwise.

As used herein, the term "infusion time" refers to the amount of time during which a composition is administered to a subject via dialysis.

As used herein, the term "about" means±10%.

A need exists for an improved IDPN composition for administration to subjects that diminishes hyperglycemia associated with IDPN administration and decreases the need for the administration of insulin with IDPN. Moreover, a need exists for a lower volume IDPN dosage form.

In one embodiment, intradialytic parenteral nutrition (IDPN) compositions with low glucose levels and low composition volume are provided. In some embodiments, the IDPN compositions allow medical personnel to engage in reduced carbohydrate management for MHD subjects when the subjects receive IDPN. In another embodiment, an IDPN composition is effective for treating malnutrition in a MHD subject with glucose management difficulties, insulin resistance, type I diabetes, type II diabetes, and/or pancreatitis. In another embodiment, administration of an IDPN composition promotes anabolism over catabolism, thereby treating malnutrition. In some embodiments, an IDPN composition has reduced volume, and in some embodiments, the reduced volume can reduce side effects associated with high infusion volumes. Non-limiting examples of the side effects associated with high infusion volumes include dyspnea, increased respiratory rate, rhonchi, edema, hypertension, hernia, and anxiety. In some embodiments, a subject receiving an IDPN composition experiences reduced symptoms of hyperglycemia.

When performing dialysis, the volume of a fluid infused into a subject can have affects on the subject. For example, different dialysis fluids, differing in volume only, can have differing affects on a subject owing to the differing volumes. Higher volumes can cause complications in subjects, such as increased fluid retention, decreased nutrient absorption, discomfort, longer or additional dialysis treatment times, and operational inconvenience. In one embodiment a subject is administered a dialysis composition with a reduced volume to provide nutrition to the subject with reduced liquid infusion. In one embodiment the subject has reduced side effects after infusion of the composition with a reduced volume. In one embodiment a subject has reduced fluid accumulation after infusion, during hemodialysis, of an IDPN composition with a reduced volume. In one embodiment the IDPN composition has a low percentage of carbohydrates. In another embodiment, the IDPN composition has a low amount of carbohydrates. In one embodiment the IDPN composition has a low percentage of an energy source that is not a carbohydrate. In another embodiment, the IDPN composition has a low amount of an energy source that is not a carbohydrate. In another embodiment the IDPN composition lacks lipids. In another embodiment the IDPN composition further comprises lipids. In one embodiment IDPN composition comprises less than 5% lipids mass/volume.

In one embodiment, IDPN compositions are provided for subjects at various stages of life. In another embodiment IDPN compositions are adapted to meet the nutritional needs of subjects across a broad range of ages. In another embodiment, a subject is an adult. In another embodiment, a subject is a young adult. In another embodiment, a subject is a juvenile. In another embodiment, a subject is an adolescent. In another embodiment, a subject is a child. In another embodiment, a subject is eligible to receive pediatric health care. In another embodiment, a subject is a pediatric subject. In another embodiment, a subject is over about 18 years old. In another embodiment, a subject is under about 18 years old. In another embodiment, a subject is under about 12 years old. In another embodiment, a subject is under about 8 years old. In another embodiment, a subject is from about 1 to about 18 years old. In another embodiment, a subject is from about 5 to about 12 years old. In another embodiment, a subject is about 1, about 2, about 3, about 4, about 5, about 6, about 7, about 8, about 9, about 10, about 11, about 12, about 13, about 14, about 15, about 16, about 17, or about 18 years old. In another embodiment, a subject is a neonatal subject. In another embodiment, a subject is less than about a year old. In another embodiment, a s subject is about 1, about 2, about 3, about 4, about 5, about 6, about 7, about 8, about 9, about 10, about 11, or about 12 months old. In another embodiment, the subject is diabetic. In another embodiment, the subject is non-diabetic. In another embodiment, the subject is either diabetic or non-diabetic. In another embodiment, the subject has high blood sugar. In another embodiment, the subject has low levels of insulin. In another embodiment, the subject has low levels of insulin because the pancreas makes too little insulin, or is insulin resistant.

In one embodiment, an IDPN composition comprises a carbohydrate and an amino acid. In one embodiment an IDPN composition consists essentially of amino acids and dextrose in an aqueous solution. In another embodiment, an IDPN composition further comprises lipids. In another embodiment, an IDPN composition comprises micronutrients, such as a vitamin, a trace element and/or a mineral. In another embodiment, an IDPN composition comprises one or more pharmaceutical agents, such as insulin. In another embodiment, one or more pharmaceutical agents are co-administered with an IDPN composition. For example, insulin can be co-administered by any ordinary method of administration, for example, subcutaneous injection. In another embodiment, an IDPN composition comprises a carbohydrate, an amino acid, and a lipid. In another embodiment, an IDPN composition comprises a carbohydrate, an amino acid, and a micronutrient, such as a vitamin, a trace element, and/or a mineral. In another embodiment, an IDPN composition comprises a carbohydrate, an amino acid, a lipid, and a micronutrient, such as a vitamin, a trace element, and/or a mineral. In another embodiment, an IDPN composition comprises a carbohydrate, an amino acid, and one or more pharmaceutical agents. In another embodiment, an IDPN composition comprises a carbohydrate, an amino acid, a lipid, and one or more pharmaceutical agents. In another embodiment, an IDPN composition comprises a carbohydrate, an amino acid, a micronutrient, and one or more pharmaceutical agents. In another embodiment, an IDPN composition comprises a carbohydrate, an amino acid, a lipid, a micronutrient, and one or more pharmaceutical agents.

In one embodiment, an IDPN composition is a solution. In another embodiment, an IDPN composition is homogeneous. In another embodiment, an IDPN composition is the product of contacting a powder with sterile water. In another embodiment, IDPN composition is the product of contacting a powder with saline. In another embodiment, an IDPN composition is a suspension.

In one embodiment, a carbohydrate comprises one or more of dextrose (D-glucose), fructose, sucrose, lactose, galactose, mannose, maltose, ribose, arabinose, sorbose, and glyceraldehyde. In another embodiment, the carbohydrate comprises dextrose. In another embodiment, the carbohydrate is dextrose. In one embodiment, the energy source that is not a carbohydrate is glycerol.

In one embodiment, an IDPN composition comprises an amino acid. In another embodiment, an IDPN composition comprises two or more amino acids. In another embodiment, an IDPN composition comprises 1, 2, 3, 4, 5, 6, 7, 8, 9, 10, 11, 12, 13, 14, 15, 16, 17, 18, 19, or 20 amino acids. In another embodiment, an IDPN composition comprises twenty amino acids. In another embodiment, an IDPN composition comprises 17 amino acids. In another embodiment, an IDPN composition comprises amino acids that consist essentially of lysine, leucine, phenylalanine, valine, histidine, isoleucine, methionine, threonine, tryptophan, alanine, arginine, glycine, proline, glutamic acid, serine, aspartic acid, and tyrosine. In another embodiment an IDPN composition comprises one or more amino acids that are not genetically-encoded. In another embodiment, an IDPN composition comprises one or more of alanine, arginine, asparagine, aspartic acid, cysteine, glutamic acid, glutamine, glycine, histidine, imidazole, isoleucine, leucine, lysine, methionine, phenylalanine, serine, threonine, tryptophan, tyrosine, or valine. In another embodiment, an IDPN composition comprises lysine, leucine, phenylalanine, valine, histidine, isoleucine, methionine, threonine, tryptophan, alanine, arginine, glycine, proline, glutamic acid, serine, aspartic acid, and tyrosine. In another embodiment, an IDPN composition comprises amino acids that consist of lysine, leucine, phenylalanine, valine, histidine, isoleucine, methionine, threonine, tryptophan, alanine, arginine, glycine, proline, glutamic acid, serine, aspartic acid, and tyrosine. In another embodiment, an IDPN composition comprises essential amino acids. In another embodiment, an IDPN composition comprises non-essential amino acids. In another embodiment, an IDPN composition comprises essential and non-essential amino acids. In another embodiment, an IDPN composition comprises amino acids that consist essentially of essential amino acids. In another embodiment, an IDPN composition comprises isoleucine, argenine, lysine, methionine, phenylalanine, threonine, tryptophan, valine, histidine, tyrosine, leucine. In another embodiment, an IDPN composition comprises amino acids that consist essentially of isoleucine, argenine, lysine, methionine, phenylalanine, threonine, tryptophan, valine, histidine, tyrosine, leucine. In another embodiment, an IDPN composition comprises leucine, isoleucine, valine, lysine, phenylalanine, histidine, threonine, methionine, tryptophan, alanine, argenine, glycine, proline, serine, and tyrosine. In another embodiment, an IDPN composition comprises amino acids that consist essentially of leucine, isoleucine, valine, lysine, phenylalanine, histidine, threonine, methionine, tryptophan, alanine, argenine, glycine, proline, serine, and tyrosine. In another embodiment, an IDPN composition comprises leucine, isoleucine, valine, lysine, phenylalanine, histidine, threonine, methionine, tryptophan, alanine, argenine, glycine, proline, serine, and cysteine. In another embodiment, an IDPN composition comprises amino acids that consist essentially of leucine, isoleucine, valine, lysine, phenylalanine, histidine, threonine, methionine, tryptophan, alanine, argenine, glycine, proline, serine, and cysteine. In another embodiment, an IDPN composition comprises branched amino acids. In another embodiment, an IDPN composition comprises amino acids that consist essentially of branched amino acids. In another embodiment, an IDPN composition comprises leucine, isoleucine, and valine. In another embodiment, an IDPN composition comprises amino acids that consist essentially of leucine, isoleucine, and valine. In another embodiment an IDPN composition comprises one or more amino acids that are not genetically-encoded. In another embodiment, an IDPN composition comprises one or more amino acids that are unnatural. In another embodiment, an IDPN composition comprises one or more amino acids that are synthetic. In another embodiment, an IDPN composition comprises one or more amino acids that are artificial. In another embodiment, an IDPN composition comprises one or more amino acids that are encoded by a nucleic acid molecule that is natural or unnatural. In another embodiment, an IDPN composition comprises one or more peptides. In another embodiment, an IDPN composition comprises amino acids and peptides. In another embodiment, an IDPN composition comprises one or more proteins. In another embodiment, an IDPN composition comprises amino acids, peptides, and proteins. In another embodiment, a peptide comprises 2, 3, 4, 5, 6, 7, 8, 9, or 10 amino acid residues. In another embodiment, a peptide comprises at least 10 amino acid residues. In another embodiment, an IDPN composition comprises 1, 2, 3, 4, 5, 6, 7, 8, 9, 10, 11, 12, 13, 14, 15, 16, 17, 18, 19, or 20 of alanine, arginine, asparagine, aspartic acid, cysteine, glutamic acid, glutamine, glycine, histidine, imidazole, isoleucine, leucine, lysine, methionine, phenylalanine, serine, threonine, tryptophan, tyrosine, and valine.

In one embodiment, the ratio of the amounts of amino acids is optimized for nutritional value. In another embodiment, the ratio of the amounts of amino acids is optimized for solubility. In another embodiment, the ratio of the amounts of amino acids is optimized for reduction of IDPN composition volume. In another embodiment, the ratio of the amounts of amino acids is optimized for administration.

In one embodiment, an IDPN composition is formulated from an amino acid stock mixture. In another embodiment, an IDPN composition comprises an amount of an amino acid stock mixture. In another embodiment, an IDPN composition comprises a volume of an amino acid stock mixture. In another embodiment, an amino acid stock mixture is an amino acid stock solution. In another embodiment, an IDPN composition comprises an amount of an amino acid stock solution. In another embodiment, an IDPN composition comprises a volume of an amino acid stock solution. In another embodiment, an amino acid stock mixture is an aqueous solution. In another embodiment, an amino acid stock mixture is a non-aqueous mixture. In another embodiment, an amino acid stock mixture is a non-aqueous solution. In another embodiment, an amino acid stock mixture is a solid mixture. In another embodiment, an amino acid stock mixture is a powder. In another embodiment, an amino acid stock mixture is a gel. In another embodiment, an amino acid stock mixture is a paste. In another embodiment, an amino acid stock mixture is a concentrate, wherein the concentrate can be diluted to a target concentration with a solvent, for example, water. In another embodiment, an amino acid stock mixture is crystalline. In another embodiment, an amino acid stock mixture is a heterogeneous mixture. In another embodiment, an amino acid stock mixture is a suspension. In another embodiment, an amino acid stock mixture comprises 20 amino acids. In another embodiment, an amino acid stock mixture comprises 17 amino acids. In another embodiment, an amino acid stock mixture is a concentrated solution. In another embodiment, an amino acid stock mixture has a reduced volume. In another embodiment, an amino acid stock mixture comprises more than about 2.5% amino acids on a mass/volume basis. In another embodiment, an amino acid stock mixture comprises more than about 2.5% amino acids on a mass/mass basis. In another embodiment, an amino acid stock mixture comprises less than about 50% amino acids on a mass/volume basis. In another embodiment, an amino acid stock mixture comprises less than about 50% amino acids on a mass/mass basis. In another embodiment, an amino acid stock mixture comprises less than about 40% amino acids on a mass/volume basis. In another embodiment, an amino acid stock mixture comprises less than about 40% amino acids on a mass/mass basis. In another embodiment, an amino acid stock mixture comprises less than about 30% amino acids on a mass/volume basis. In another embodiment, an amino acid stock mixture comprises less than about 30% amino acids on a mass/mass basis. In another embodiment, an amino acid stock mixture comprises less than about 25% amino acids on a mass/volume basis. In another embodiment, an amino acid stock mixture comprises less than about 25% amino acids on a mass/mass basis. In another embodiment, an amino acid stock mixture comprises from about 2.5% to about 50% amino acids on a mass/volume basis. In another embodiment, an amino acid stock mixture comprises from about 2.5% to about 50% amino acids on a mass/mass basis. In another embodiment, an amino acid stock mixture comprises from about 2.5% to about 40% amino acids on a mass/volume basis. In another embodiment, an amino acid stock mixture comprises from about 2.5% to about 40% amino acids on a mass/mass basis. In another embodiment, an amino acid stock mixture comprises from about 2.5% to about 30% amino acids on a mass/volume basis. In another embodiment, an amino acid stock mixture comprises from about 2.5% to about 30% amino acids on a mass/mass basis. In another embodiment, an amino acid stock mixture comprises from about 2.5% to about 25% amino acids on a mass/volume basis. In another embodiment, an amino acid stock mixture comprises from about 2.5% to about 25% amino acids on a mass/mass basis. In another embodiment, an amino acid stock mixture comprises from about 5% to about 20% amino acids on a mass/volume basis. In another embodiment, an amino acid stock mixture comprises from about 5% to about 20% amino acids on a mass/mass basis. In another embodiment, an amino acid stock mixture comprises about 5% amino acids on a mass/volume basis. In another embodiment, an amino acid stock mixture comprises about 5% amino acids on a mass/mass basis. In another embodiment, an amino acid stock solution comprises about 5% amino acids on a mass/volume basis. In another embodiment, an amino acid stock solution comprises about 5% amino acids on a mass/mass basis. In another embodiment, an amino acid stock mixture comprises about 10% amino acids on a mass/volume basis. In another embodiment, an amino acid stock mixture comprises about 10% amino acids on a mass/mass basis. In another embodiment, an amino acid stock solution comprises about 10% amino acids on a mass/volume basis. In another embodiment, an amino acid stock solution comprises about 10% amino acids on a mass/mass basis. In another embodiment, an amino acid stock mixture comprises about 15% amino acids on a mass/volume basis. In another embodiment, an amino acid stock mixture comprises about 15% amino acids on a mass/mass basis. In another embodiment, an amino acid stock solution comprises about 15% amino acids on a mass/volume basis. In another embodiment, an amino acid stock solution comprises about 15% amino acids on a mass/mass basis. In another embodiment, an amino acid stock mixture comprises about 20% amino acids on a mass/volume basis. In another embodiment, an amino acid stock mixture comprises about 20% amino acids on a mass/mass basis. In another embodiment, an amino acid stock solution comprises about 20% amino acids on a mass/volume basis. In another embodiment, an amino acid stock solution comprises about 20% amino acids on a mass/mass basis. In another embodiment, an amino acid stock mixture comprises about 25% amino acids on a mass/volume basis. In another embodiment, an amino acid stock mixture comprises about 25% amino acids on a mass/mass basis. In another embodiment, an amino acid stock solution comprises about 25% amino acids on a mass/volume basis. In another embodiment, an amino acid stock solution comprises about 25% amino acids on a mass/mass basis. In another embodiment, an amino acid stock mixture comprises about 30% amino acids on a mass/volume basis. In another embodiment, an amino acid stock mixture comprises about 30% amino acids on a mass/mass basis. In another embodiment, an amino acid stock solution comprises about 30% amino acids on a mass/volume basis. In another embodiment, an amino acid stock solution comprises about 30% amino acids on a mass/mass basis. In another embodiment, an amino acid stock mixture comprises about 35% amino acids on a mass/volume basis. In another embodiment, an amino acid stock mixture comprises about 35% amino acids on a mass/mass basis. In another embodiment, an amino acid stock solution comprises about 35% amino acids on a mass/volume basis. In another embodiment, an amino acid stock solution comprises about 35% amino acids on a mass/mass basis. In another embodiment, an amino acid stock mixture comprises about 40% amino acids on a mass/volume basis. In another embodiment, an amino acid stock mixture comprises about 40% amino acids on a mass/mass basis. In another embodiment, an amino acid stock solution comprises about 40% amino acids on a mass/volume basis. In another embodiment, an amino acid stock solution comprises about 40% amino acids on a mass/mass basis. In another embodiment, an amino acid stock mixture comprises about 45% amino acids on a mass/volume basis. In another embodiment, an amino acid stock mixture comprises about 45% amino acids on a mass/mass basis. In another embodiment, an amino acid stock solution comprises about 45% amino acids on a mass/volume basis. In another embodiment, an amino acid stock solution comprises about 45% amino acids on a mass/mass basis. In another embodiment, an amino acid stock mixture comprises about 50% amino acids on a mass/volume basis. In another embodiment, an amino acid stock mixture comprises about 50% amino acids on a mass/mass basis. In another embodiment, an amino acid stock solution comprises about 50% amino acids on a mass/volume basis. In another embodiment, an amino acid stock solution comprises about 50% amino acids on a mass/mass basis.

In one embodiment, an amino acid stock mixture comprising 15% amino acids on a mass/volume basis has the formulation described in Table I.

TABLE I

| | |
|---|---|
| Amino Acids | 15.0 g |
| Total Nitrogen | 2.37 g |
| PH, optionally adjusted with glacial acetic acid and/or sodium hydroxide | 6.0 ± 1.0 |
| Lysine (from Lysine Acetate) | 1.18 g |
| Leucine | 1.04 g |
| Phenylalanine | 1.04 g |
| Valine | 960 mg |
| Histidine | 894 mg |
| Isoleucine | 749 mg |
| Methionine | 749 mg |
| Threonine | 749 mg |
| Tryptophan | 250 mg |
| Alanine | 2.17 g |
| Arginine | 1.47 g |
| Glycine | 1.04 g |
| Proline | 894 mg |
| Glutamic Acid | 749 mg |
| Serine | 592 mg |
| Aspartic Acid | 434 mg |

TABLE I-continued

| | | |
|---|---|---|
| Tyrosine | 39 | mg |
| Acetate from Lysine Acetate and glacial acetic acid (balanced by ions from amino acids) | 127 | mEq |
| Osmolarity (Calculated) | 1357 | mOsmol/L |
| Total Volume, water being the balance of the volume | 100 | mL |

In one embodiment, an amino acid stock mixture comprising 15% amino acids on a mass/volume basis has the formulation described in Table II.

TABLE II

| | | |
|---|---|---|
| Amino Acids | 15.0 | g |
| Total Nitrogen | 2.37 | g |
| PH, optionally adjusted with glacial acetic acid and/or sodium hydroxide | 6.0 ± 0.1 | |
| Lysine (from Lysine Acetate) | 1.18 | g |
| Leucine | 1.04 | g |
| Phenylalanine | 1.04 | g |
| Valine | 960 | mg |
| Histidine | 894 | mg |
| Isoleucine | 749 | mg |
| Methionine | 749 | mg |
| Threonine | 749 | mg |
| Tryptophan | 250 | mg |
| Alanine | 2.17 | g |
| Arginine | 1.47 | g |
| Glycine | 1.04 | g |
| Proline | 894 | mg |
| Glutamic Acid | 749 | mg |
| Serine | 592 | mg |
| Aspartic Acid | 434 | mg |
| Tyrosine | 39 | mg |
| Acetate from Lysine Acetate and glacial acetic acid (balanced by ions from amino acids) | 127 | mEq |
| Osmolarity (Calculated) | 1357 | mOsmol/L |
| Total Volume, water being the balance of the volume | 100 | mL |

In one embodiment, an amino acid stock mixture comprising 20% amino acids on a mass/volume basis has the formulation described in Table II.

TABLE III

| | | |
|---|---|---|
| Amino Acids | 20.0 | g |
| Total Nitrogen | 3.21 | g |
| PH, optionally adjusted with glacial acetic acid and/or sodium hydroxide | 6.0 ± 0.5 | |
| Lysine (from Lysine Acetate) | 1.35 | g |
| Leucine | 1.08 | g |
| Phenylalanine | 1.00 | g |
| Valine | 1.44 | g |
| Histidine | 1.18 | mg |
| Isoleucine | 1.08 | mg |
| Methionine | 760 | mg |
| Threonine | 980 | mg |
| Tryptophan | 320 | mg |
| Alanine | 2.76 | g |
| Arginine | 1.96 | g |
| Glycine | 2.06 | g |
| Proline | 1.34 | g |
| Glutamic Acid | 1.02 | g |
| Serine | 1.02 | g |
| Aspartic Acid | 600 | mg |
| Tyrosine | 50 | mg |
| Acetate from Lysine Acetate and glacial acetic acid (balanced by ions from amino acids) | 140 | mEq |
| Osmolarity (Calculated) | 1835 | mOsmol/L |
| Total Volume, water being the balance of the volume | 100 | mL |

In one embodiment, an amino acid stock mixture comprising 20% amino acids on a mass/volume basis has the formulation described in Table IV.

TABLE IV

| | | |
|---|---|---|
| Amino Acids | 20.0 | g |
| Total Nitrogen | 3.21 | g |
| PH, optionally adjusted with glacial acetic acid and/or sodium hydroxide | 6.0 ± 0.1 | |
| Lysine (from Lysine Acetate) | 1.35 | g |
| Leucine | 1.08 | g |
| Phenylalanine | 1.00 | g |
| Valine | 1.44 | g |
| Histidine | 1.18 | mg |
| Isoleucine | 1.08 | mg |
| Methionine | 760 | mg |
| Threonine | 980 | mg |
| Tryptophan | 320 | mg |
| Alanine | 2.76 | g |
| Arginine | 1.96 | g |
| Glycine | 2.06 | g |
| Proline | 1.34 | g |
| Glutamic Acid | 1.02 | g |
| Serine | 1.02 | g |
| Aspartic Acid | 600 | mg |
| Tyrosine | 50 | mg |
| Acetate from Lysine Acetate and glacial acetic acid (balanced by ions from amino acids) | 140 | mEq |
| Osmolarity (Calculated) | 1835 | mOsmol/L |
| Total Volume, water being the balance of the volume | 100 | mL |

In one embodiment, an IDPN composition comprises less than about 1 g/mL of dextrose. In another embodiment, an IDPN composition comprises less than about 0.5 g/mL of dextrose. In another embodiment, an IDPN composition comprises less than about 0.25 g/mL of dextrose. In another embodiment, an IDPN composition comprises less than about 0.1 g/mL of dextrose. In another embodiment, an IDPN composition comprises more than about 0.02 g/mL of dextrose. In another embodiment, an IDPN composition comprises more than about 0.03 g/mL of dextrose. In another embodiment, an IDPN composition comprises more than about 0.04 g/mL of dextrose. In another embodiment, an IDPN composition comprises more than about 0.05 g/mL of dextrose. In another embodiment, an IDPN composition comprises more than about 0.1 g/mL of dextrose. In another embodiment, an IDPN composition comprises between about 0.02 and about 0.10 g/mL of dextrose. In another embodiment, an IDPN composition comprises between about 0.04 and about 0.08 g/mL of dextrose. In another embodiment, an IDPN composition comprises between about 0.05 and about 0.07 g/mL of dextrose. In another embodiment, an IDPN composition comprises between about 0.055 and about 0.065 g/mL of dextrose. In another embodiment, an IDPN comprises about 0.02, about 0.03, about 0.04, about 0.05, about 0.06, about 0.07, about 0.08, about 0.09 or about 0.10 g/mL of dextrose. In another embodiment, an IDPN composition comprises about 0.055, about 0.056, about 0.057, about 0.058, about 0.059, about 0.060, about 0.061, about 0.062, about 0.063, about 0.064 or about 0.065 g/mL of dextrose.

In one embodiment, a carbohydrate is introduced into an IDPN composition by adding to an IDPN composition an amount of a stock carbohydrate solution. In another embodiment, a carbohydrate is introduced into an IDPN composition by adding to an IDPN composition a volume of a stock carbohydrate solution. In another embodiment, a stock carbohydrate solution has a carbohydrate concentration of at least about 10% on a mass/volume basis. In another embodiment, a stock carbohydrate solution has a carbohydrate concentration of at least about 10% on a mass/mass basis. In another embodiment, a stock carbohydrate solution has a carbohydrate concentration of at least about 20% on a mass/volume basis. In another embodiment, a stock carbohydrate solution has a carbohydrate concentration of at least about 20% on a mass/mass basis. In another embodiment, a stock carbohydrate solution has a carbohydrate concentration of at least about 30% on a mass/volume basis. In another embodiment, a stock carbohydrate solution has a carbohydrate concentration of at least about 30% on a mass/mass basis. In another embodiment, a stock carbohydrate solution has a carbohydrate concentration of at least about 40% on a mass/volume basis. In another embodiment, a stock carbohydrate solution has a carbohydrate concentration of at least about 40% on a mass/mass basis. In another embodiment, a stock carbohydrate solution has a carbohydrate concentration of at least about 50% on a mass/volume basis. In another embodiment, a stock carbohydrate solution has a carbohydrate concentration of at least about 50% on a mass/mass basis. In another embodiment, a stock carbohydrate solution has a carbohydrate concentration of at least about 60% on a mass/volume basis. In another embodiment, a stock carbohydrate solution has a carbohydrate concentration of at least about 60% on a mass/mass basis. In another embodiment, a stock carbohydrate solution has a carbohydrate concentration of at least about 70% on a mass/volume basis. In another embodiment, a stock carbohydrate solution has a carbohydrate concentration of at least about 70% on a mass/mass basis. In another embodiment, a stock carbohydrate solution has a carbohydrate concentration of less than about 80% on a mass/volume basis. In another embodiment, a stock carbohydrate solution has a carbohydrate concentration of less than about 80% on a mass/mass basis. In another embodiment, a stock carbohydrate solution has a carbohydrate concentration of from about 10% to about 80% on a mass/volume basis. In another embodiment, a stock carbohydrate solution has a carbohydrate concentration of from about 10% to about 80% on a mass/mass basis. In another embodiment, a stock carbohydrate solution has a carbohydrate concentration of from about 20% to about 80% on a mass/volume basis. In another embodiment, a stock carbohydrate solution has a carbohydrate concentration of from about 20% to about 80% on a mass/mass basis. In another embodiment, a stock carbohydrate solution has a carbohydrate concentration of from about 40% to about 80% on a mass/volume basis. In another embodiment, a stock carbohydrate solution has a carbohydrate concentration of from about 40% to about 80% on a mass/mass basis. In another embodiment, a stock carbohydrate solution has a carbohydrate concentration of from about 60% to about 80% on a mass/volume basis. In another embodiment, a stock carbohydrate solution has a carbohydrate concentration of from about 60% to about 80% on a mass/mass basis. In another embodiment, a stock carbohydrate solution has a carbohydrate concentration of about 5%, about 10%, about 15%, about 20%, about 25%, about 30%, about 35%, about 40%, about 45%, about 50%, about 55%, about 60%, about 65%, about 70%, about 75%, or about 80% on a mass/volume basis. In another embodiment, a stock carbohydrate solution has a carbohydrate concentration of from about 60% to about 80% on a mass/mass basis. In another embodiment, a stock carbohydrate solution has a carbohydrate concentration of about 5%, about 10%, about 15%, about 20%, about 25%, about 30%, about 35%, about 40%, about 45%, about 50%, about 55%, about 60%, about 65%, about 70%, about 75%, or about 80% on a mass/mass basis. In another embodiment, a stock carbohydrate solution has a carbohydrate concentration of about 70% on a mass/volume basis. In another embodiment, a stock carbohydrate solution has a carbohydrate concentration of about 70% on a mass/mass basis. In another embodiment, the carbohydrate of the stock carbohydrate solution is dextrose. In another embodiment, a stock carbohydrate solution has a dextrose concentration of at least about 10% on a mass/volume basis. In another embodiment, a stock carbohydrate solution has a dextrose concentration of at least about 10% on a mass/mass basis. In another embodiment, a stock carbohydrate solution has a dextrose concentration of at least about 20% on a mass/volume basis. In another embodiment, a stock carbohydrate solution has a dextrose concentration of at least about 20% on a mass/mass basis. In another embodiment, a stock carbohydrate solution has a dextrose concentration of at least about 30% on a mass/volume basis. In another embodiment, a stock carbohydrate solution has a dextrose concentration of at least about 30% on a mass/mass basis. In another embodiment, a stock carbohydrate solution has a dextrose concentration of at least about 40% on a mass/volume basis. In another embodiment, a stock carbohydrate solution has a dextrose concentration of at least about 40% on a mass/mass basis. In another embodiment, a stock carbohydrate solution has a dextrose concentration of at least about 50% on a mass/volume basis. In another embodiment, a stock carbohydrate solution has a dextrose concentration of at least about 50% on a mass/mass basis. In another embodiment, a stock carbohydrate solution has a dextrose concentration of at least about 60% on a mass/volume basis. In another embodiment, a stock carbohydrate solution has a dextrose concentration of at least about 60% on a mass/mass basis. In another embodiment, a stock carbohydrate solution has a dextrose concentration of at least about 70% on a mass/volume basis. In another embodiment, a stock carbohydrate solution has a dextrose concentration of at least about 70% on a mass/mass basis. In another embodiment, a stock carbohydrate solution has a dextrose concentration of less than about 80% on a mass/volume basis. In another embodiment, a stock carbohydrate solution has a dextrose concentration of less than about 80% on a mass/mass basis. In another embodiment, a stock carbohydrate solution has a dextrose concentration of from about 10% to about 80% on a mass/volume basis. In another embodiment, a stock carbohydrate solution has a dextrose concentration of from about 10% to about 80% on a mass/mass basis. In another embodiment, a stock carbohydrate solution has a dextrose concentration of from about 20% to about 80% on a mass/volume basis. In another embodiment, a stock carbohydrate solution has a dextrose concentration of from about 20% to about 80% on a mass/mass basis. In another embodiment, a stock carbohydrate solution has a dextrose concentration of from about 40% to about 80% on a mass/volume basis. In another embodiment, a stock carbohydrate solution has a dextrose concentration of from about 40% to about 80% on a mass/mass basis. In another embodiment, a stock carbohydrate solution has a dextrose concentration of from about 60% to about 80% on a mass/volume basis. In another embodiment, a stock carbohydrate solution has a dextrose concentration of from about 60% to about 80% on a mass/mass basis. In another embodiment, a stock carbohydrate solution has a dextrose concentration of about 5%, about 10%, about 15%, about 20%, about 25%, about 30%, about 35%, about 40%, about 45%, about 50%, about 55%, about 60%, about 65%, about 70%, about 75%, or about 80% on a mass/volume basis. In another embodiment, a stock carbohydrate solution has a dextrose concentration of about 5%, about 10%, about 15%, about 20%, about 25%, about 30%, about 35%, about 40%, about 45%, about 50%, about 55%, about 60%, about 65%, about 70%, about 75%, or about 80% on a mass/mass basis. In another embodiment, a stock carbohydrate solution has a dextrose concentration of about 70% on a mass/volume basis. In another embodiment, a stock carbohydrate solution has a dextrose concentration of about 70% on a mass/mass basis.

In one embodiment, an IDPN composition comprises a lipid. In another embodiment, an IDPN composition comprises greater than about 0.001 g/mL of lipids. In another embodiment, an IDPN composition comprises greater than about 0.005 g/mL of lipids. In another embodiment, an IDPN composition comprises greater than about 0.01 g/mL of lipids. In another embodiment, an IDPN composition comprises greater than about 0.02 g/mL of lipids. In another embodiment, an IDPN composition comprises less than about 0.10 g/mL of lipids. In another embodiment, an IDPN composition comprises less than about 0.05 g/mL of lipids. In another embodiment, an IDPN composition comprises less than about 0.03 g/mL of lipids. In another embodiment, an IDPN composition comprises from about 0.001 g/mL to about 0.10 g/mL of lipids. In another embodiment, an IDPN composition comprises from about 0.01 g/mL to about 0.05 g/mL of lipids. In another embodiment, an IDPN composition comprises from about 0.015 g/mL to about 0.035 g/mL of lipids. In another embodiment, an IDPN composition comprises from about 0.02 g/mL to about 0.03 g/mL of lipids. In another embodiment, an IDPN composition comprises about 0.010 g/mL, about 0.011 g/mL, about 0.012 g/mL, about 0.013 g/mL, about 0.014 g/mL, about 0.015 g/mL, about 0.016 g/mL, about 0.017 g/mL, about 0.018 g/mL, about 0.019 g/mL, about 0.020 g/mL, about 0.021 g/mL, about 0.022 g/mL, about 0.023 g/mL, about 0.024 g/mL, about 0.025 g/mL, about 0.026 g/mL, about 0.027 g/mL, about 0.028 g/mL, about 0.029 g/mL, about 0.030 g/mL, about 0.031 g/mL, about 0.032 g/mL, about 0.033 g/mL, about 0.034 g/mL, about 0.035 g/mL, about 0.036 g/mL, about 0.037 g/mL, about 0.038 g/mL, about 0.039 g/mL, about 0.040 g/mL, about 0.041 g/mL, about 0.042 g/mL, about 0.043 g/mL, about 0.044 g/mL, about 0.045 g/mL, about 0.046 g/mL, about 0.047 g/mL, about 0.048 g/mL, about 0.049 g/mL, or about 0.050 g/mL of lipids.

In one embodiment, a lipid is introduced into an IDPN composition by adding to an IDPN composition an amount of a stock lipid mixture. In another embodiment, a lipid stock mixture is a solution. In another embodiment, a lipid stock mixture is an aqueous solution. In another embodiment, a lipid stock mixture is a non-aqueous mixture. In another embodiment, a lipid stock mixture is a non-aqueous solution. In another embodiment, a lipid stock mixture is a solid mixture. In another embodiment, a lipid stock mixture is a powder. In another embodiment, a lipid stock mixture is a gel. In another embodiment, a lipid stock mixture is a paste. In another embodiment, a lipid stock mixture is a concentrate, wherein the concentrate can be diluted to a target concentration with a solvent, for example, water. In another embodiment, a lipid stock mixture is crystalline. In another embodiment, a lipid stock mixture is a heterogeneous mixture. In another embodiment, a lipid stock mixture is a suspension. In another embodiment, a lipid stock mixture is an emulsion. In another embodiment, a lipid stock mixture comprises a fat-soluble vitamin, for example, vitamin D. In another embodiment, a lipid stock mixture comprises greater than about 2.5% lipids on a mass/volume basis. In another embodiment, a lipid stock mixture comprises greater than about 2.5% lipids on a mass/mass basis. In another embodiment, a lipid stock mixture comprises greater than about 2.5% lipids on a volume/volume basis. In another embodiment, a lipid stock solution comprises greater than about 2.5% lipids on a mass/volume basis. In another embodiment, a lipid stock solution comprises greater than about 2.5% lipids on a mass/mass basis. In another embodiment, a lipid stock solution comprises greater than about 2.5% lipids on a volume/volume basis. In another embodiment, a lipid stock mixture comprises greater than about 5% lipids on a mass/volume basis. In another embodiment, a lipid stock mixture comprises greater than about 5% lipids on a mass/mass basis. In another embodiment, a lipid stock mixture comprises greater than about 5% lipids on a volume/volume basis. In another embodiment, a lipid stock solution comprises greater than about 5% lipids on a mass/volume basis. In another embodiment, a lipid stock solution comprises greater than about 5% lipids on a mass/mass basis. In another embodiment, a lipid stock solution comprises greater than about 5% lipids on a volume/volume basis. In another embodiment, a lipid stock mixture comprises less than about 70% lipids on a mass/volume basis. In another embodiment, a lipid stock mixture comprises less than about 70% lipids on a mass/mass basis. In another embodiment, a lipid stock mixture comprises less than about 70% lipids on a volume/volume basis. In another embodiment, a lipid stock solution comprises less than about 70% lipids on a mass/volume basis. In another embodiment, a lipid stock solution comprises less than about 70% lipids on a mass/mass basis. In another embodiment, a lipid stock solution comprises less than about 70% lipids on a volume/volume basis. In another embodiment, a lipid stock mixture comprises less than about 60% lipids on a mass/volume basis. In another embodiment, a lipid stock mixture comprises less than about 60% lipids on a mass/mass basis. In another embodiment, a lipid stock mixture comprises less than about 60% lipids on a volume/volume basis. In another embodiment, a lipid stock solution comprises less than about 60% lipids on a mass/volume basis. In another embodiment, a lipid stock solution comprises less than about 60% lipids on a mass/mass basis. In another embodiment, a lipid stock solution comprises less than about 60% lipids on a volume/volume basis. In another embodiment, a lipid stock mixture comprises from about 2.5% to about 70% lipids on a mass/volume basis. In another embodiment, a lipid stock mixture comprises from about 2.5% to about 70% lipids on a mass/mass basis. In another embodiment, a lipid stock mixture comprises from about 2.5% to about 70% lipids on a volume/volume basis. In another embodiment, a lipid stock solution comprises from about 2.5% to about 70% lipids on a mass/volume basis. In another embodiment, a lipid stock solution comprises from about 2.5% to about 70% lipids on a mass/mass basis. In another embodiment, a lipid stock solution comprises from about 2.5% to about 70% lipids on a volume/volume basis. In another embodiment, a lipid stock mixture comprises from about 5% to about 50% lipids on a mass/volume basis. In another embodiment, a lipid stock mixture comprises from about 5% to about 50% lipids on a mass/mass basis. In another embodiment, a lipid stock mixture comprises from about 5% to about 50% lipids on a volume/volume basis. In another embodiment, a lipid stock solution comprises from about 5% to about 50% lipids on a mass/volume basis. In another embodiment, a lipid stock solution comprises from about 5% to about 50% lipids on a mass/mass basis. In another embodiment, a lipid stock solution comprises from about 5% to about 50% lipids on a volume/volume basis. In another embodiment, a lipid stock mixture comprises from about 10% to about 30% lipids on a mass/volume basis. In another embodiment, a lipid stock mixture comprises from about 10% to about 30% lipids on a mass/mass basis. In another embodiment, a lipid stock mixture comprises from about 10% to about 30% lipids on a volume/volume basis. In another embodiment, a lipid stock solution comprises from about 10% to about 30% lipids on a mass/volume basis. In another embodiment, a lipid stock solution comprises from about 10% to about 30% lipids on a mass/mass basis. In another embodiment, a lipid stock solution comprises 1 from about 10% to about 30% lipids on a volume/volume basis. In another embodiment, a lipid stock mixture comprises about 5% lipids on a mass/volume basis. In another embodiment, a lipid stock mixture comprises about 5% lipids on a mass/mass basis. In another embodiment, a lipid stock mixture comprises about 5% lipids on a volume/volume basis. In another embodiment, a lipid stock solution comprises about 5% lipids on a mass/volume basis. In another embodiment, a lipid stock solution comprises about 5% lipids on a mass/mass basis. In another embodiment, a lipid stock solution comprises about 5% lipids on a volume/volume basis. In another embodiment, a lipid stock mixture comprises about 10% lipids on a mass/volume basis. In another embodiment, a lipid stock mixture comprises about 10% lipids on a mass/mass basis. In another embodiment, a lipid stock mixture comprises about 10% lipids on a volume/volume basis. In another embodiment, a lipid stock solution comprises about 10% lipids on a mass/volume basis. In another embodiment, a lipid stock solution comprises about 10% lipids on a mass/mass basis. In another embodiment, a lipid stock solution comprises about 10% lipids on a volume/volume basis. In another embodiment, a lipid stock mixture comprises about 15% lipids on a mass/volume basis. In another embodiment, a lipid stock mixture comprises about 15% lipids on a mass/mass basis. In another embodiment, a lipid stock mixture comprises about 15% lipids on a volume/volume basis. In another embodiment, a lipid stock solution comprises about 15% lipids on a mass/volume basis. In another embodiment, a lipid stock solution comprises about 15% lipids on a mass/mass basis. In another embodiment, a lipid stock solution comprises about 15% lipids on a volume/volume basis. In another embodiment, a lipid stock mixture comprises about 20% lipids on a mass/volume basis. In another embodiment, a lipid stock mixture comprises about 20% lipids on a mass/mass basis. In another embodiment, a lipid stock mixture comprises about 20% lipids on a volume/volume basis. In another embodiment, a lipid stock solution comprises about 20% lipids on a mass/volume basis. In another embodiment, a lipid stock solution comprises about 20% lipids on a mass/mass basis. In another embodiment, a lipid stock solution comprises about 20% lipids on a volume/volume basis. In another embodiment, a lipid stock mixture comprises about 25% lipids on a mass/volume basis. In another embodiment, a lipid stock mixture comprises about 25% lipids on a mass/mass basis. In another embodiment, a lipid stock mixture comprises about 25% lipids on a volume/volume basis. In another embodiment, a lipid stock solution comprises about 25% lipids on a mass/volume basis. In another embodiment, a lipid stock solution comprises about 25% lipids on a mass/mass basis. In another embodiment, a lipid stock solution comprises about 25% lipids on a volume/volume basis. In another embodiment, a lipid stock mixture comprises about 30% lipids on a mass/volume basis. In another embodiment, a lipid stock mixture comprises about 30% lipids on a mass/mass basis. In another embodiment, a lipid stock mixture comprises about 30% lipids on a volume/volume basis. In another embodiment, a lipid stock solution comprises about 30% lipids on a mass/volume basis. In another embodiment, a lipid stock solution comprises about 30% lipids on a mass/mass basis. In another embodiment, a lipid stock solution comprises about 30% lipids on a volume/volume basis. In another embodiment, a lipid stock mixture comprises about 35% lipids on a mass/volume basis. In another embodiment, a lipid stock mixture comprises about 35% lipids on a mass/mass basis. In another embodiment, a lipid stock mixture comprises about 35% lipids on a volume/volume basis. In another embodiment, a lipid stock solution comprises about 35% lipids on a mass/volume basis. In another embodiment, a lipid stock solution comprises about 35% lipids on a mass/mass basis. In another embodiment, a lipid stock solution comprises about 35% lipids on a volume/volume basis. In another embodiment, a lipid stock mixture comprises about 40% lipids on a mass/volume basis. In another embodiment, a lipid stock mixture comprises about 40% lipids on a mass/mass basis. In another embodiment, a lipid stock mixture comprises about 40% lipids on a volume/volume basis. In another embodiment, a lipid stock solution comprises about 40% lipids on a mass/volume basis. In another embodiment, a lipid stock solution comprises about 40% lipids on a mass/mass basis. In another embodiment, a lipid stock solution comprises about 40% lipids on a volume/volume basis. In another embodiment, a lipid stock mixture comprises about 45% lipids on a mass/volume basis. In another embodiment, a lipid stock mixture comprises about 45% lipids on a mass/mass basis. In another embodiment, a lipid stock mixture comprises about 45% lipids on a volume/volume basis. In another embodiment, a lipid stock solution comprises about 45% lipids on a mass/volume basis. In another embodiment, a lipid stock solution comprises about 45% lipids on a mass/mass basis. In another embodiment, a lipid stock solution comprises about 45% lipids on a volume/volume basis. In another embodiment, a lipid stock mixture comprises about 50% lipids on a mass/volume basis. In another embodiment, a lipid stock mixture comprises about 50% lipids on a mass/mass basis. In another embodiment, a lipid stock mixture comprises about 50% lipids on a volume/volume basis. In another embodiment, a lipid stock solution comprises about 50% lipids on a mass/volume basis. In another embodiment, a lipid stock solution comprises about 50% lipids on a mass/mass basis. In another embodiment, a lipid stock solution comprises about 50% lipids on a volume/volume basis.

In one embodiment, an IDPN composition is packaged in a sterile container. In another embodiment, a sterile container is effective for administration to a subject. In another embodiment, a sterile container is a bag. In another embodiment, a sterile container is effective for parenteral administration of an IDPN composition to a subject. In another embodiment, a bag holds between about 100 and about 2 liters of an IDPN composition. In another embodiment, a bag holds between about 300 mL to about 1 liter of an IDPN composition. In another embodiment, a bag holds between about 419 mL and about 809 mL of an IDPN composition. In another embodiment, a bag holds between about 350 mL and about 635 mL of an IDPN composition. In another embodiment, a bag holds less than about 2 liters of an IDPN composition. In another embodiment, a bag holds less than about 1 liter of an IDPN composition. In another embodiment, a bag holds more than about 10 mL of an IDPN composition. In another embodiment, a bag holds more than about 100 mL of an IDPN composition. In another embodiment, a bag holds more than 1 liter of an IDPN composition.

In one embodiment, a sterile container holds one dose of an IDPN composition. In another embodiment, a sterile container is effective for administration of one dose to a subject.

In one embodiment, a dose has a volume between about 100 mL and about 2 liters. In another embodiment, a dose has a volume between about 350 mL and about 635 mL. In another embodiment, a dose has a volume of about 300, about 342, about 350, about 383, about 400, about 419, about 427, about 450, about 483, about 500, about 540, about 550, about 600, about 613, about 635, about 700 or about 809 mL. In another embodiment, a dose has a volume less than about 2 liters. In another embodiment, a dose has a volume less than about 1 liter. In another embodiment, a dose has a volume more than about 10 mL. In another embodiment, a dose has a volume more than about 100 mL. In another embodiment, a dose has a volume more than 1 liter.

In one embodiment, a dose comprises between about 10 and about 50 g of dextrose. In another embodiment, a dose comprises between about 20 and about 45 g of dextrose. In another embodiment, a dose comprises more than about 10 g of dextrose. In another embodiment, a dose comprises less than about 50 g of dextrose. In another embodiment, a dose comprises about 20, about 23, about 26, about 30, about 35 or about 41 g of dextrose.

In one embodiment, the amount of dextrose in a dose is dependent upon the body mass of a subject receiving the dose. In another embodiment, the amount of dextrose in a dose is dependent on the duration of hemodialysis. In another embodiment, the amount of dextrose in a dose is dependent upon the body mass of a subject receiving the dose and the duration of hemodialysis. In another embodiment, a dose comprises less than about 1 g of dextrose per kg of body mass of the subject. In another embodiment, a dose comprises a mass of dextrose from about 50% to about 60% the body mass of a subject on a (g/kg) basis. Non-limiting examples follow. In one non-limiting example, a subject with a body mass between about 34 and about 39 kg receives a dose comprising about 20 g of dextrose. In one non-limiting example, a subject with a body mass between about 40 and about 44 kg receives a dose comprising about 23 g of dextrose. In one non-limiting example, a subject with a body mass between about 45 and about 51 kg receives a dose comprising about 26 g of dextrose. In one non-limiting example, a subject with a body mass between about 52 and about 59 kg receives a dose comprising about 30 g of dextrose. In one non-limiting example, a subject with a body mass between about 60 and about 69 kg receives a dose comprising about 35 g of dextrose. In one non-limiting example, a subject with a body mass of about 70 kg, or greater, receives a dose comprising about 41 g of dextrose, or greater. In one embodiment the duration of hemodialysis is between 2-4.5 hrs. In one embodiment the duration of hemodialysis is between 2.75-4 hrs.

In one embodiment, an IDPN composition comprises between about 0.10 and about 1.0 g/mL of amino acids. In another embodiment, an IDPN composition comprises between about 0.10 and about 0.50 g/mL of amino acids. In another embodiment, an IDPN composition comprises between about 0.10 and about 0.20 g/mL of amino acids. In another embodiment, an IDPN composition comprises between about 0.12 and about 0.18 g/ml of amino acids. In another embodiment, an IDPN comprises between about 0.15 and about 0.17 g/mL of amino acids. In another embodiment, an IDPN composition comprises about 0.10, about 0.11, about 0.12, about 0.13, about 0.14, about 0.15, about 0.16, about 0.17, about 0.18, about 0.19 or about 0.20 g/mL of amino acids. In another embodiment, an IDPN composition comprises more than about 0.10 g/mL of amino acids. In another embodiment, an IDPN composition comprises less than about 1.0 g/mL. In another embodiment, an IDPN composition comprises less than about 0.50 g/mL. In another embodiment, an IDPN composition comprises less than about 0.20 g/mL. In another embodiment, an IDPN composition comprises about 0.150, about 0.151, about 0.152, about 0.153, about 0.154, about 0.155, about 0.156, about 0.157, about 0.158, about 0.159, about 0.160, about 0.161, about 0.162, about 0.163, about 0.164, about 0.165, about 0.166, about 0.167, about 0.168, about 0.169 or about 0.170 g/mL of amino acids.

In one embodiment, a dose comprises a least about 1 g of amino acids. In another embodiment, a dose comprises less than about 200 g of amino acids. In another embodiment, a dose comprises between about 10 and about 200 g of amino acids. In another embodiment, a dose comprises between about 20 and about 150 g of amino acids. In another embodiment, a dose comprises between about 30 and about 120 g of amino acids. In another embodiment, a dose comprises between about 50 and about 110 g of amino acids. In another embodiment, a dose comprises about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, about 23.5, about 24, about 24.5, about 25, about 25.5, about 26, about 26.5, about 27, about 27.5, about 28, about 28.5, about 29, about 29.5, about 30, about 30.5, about 31, about 31.5, about 32, about 32.5, about 33, about 33.5, about 34, about 34.5, about 35, about 35.5, about 36, about 36.5, about 37, about 37.5, about 38, about 38.5, about 39, about 39.5, about 40, about 40.5, about 41, about 41.5, about 42, about 42.5, about 43, about 43.5, about 44, about 44.5, about 45, about 45.5, about 46, about 46.5, about 47, about 47.5, about 48, about 48.5, about 49, about 49.5, about 50, about 50.5, about 51, about 51.5, about 52, about 52.5, about 53, about 53.5, about 54, about 54.5, about 55, about 55.5, about 56, about 56.5, about 57, about 57.5, about 58, about 58.5, about 59, about 59.5, about 60, about 60.5, about 61, about 61.5, about 62, about 62.5, about 63, about 63.5, about 64, about 64.5, about 65, about 65.5, about 66, about 66.5, about 67, about 67.5, about 68, about 68.5, about 69, about 69.5, about 70, about 70.5, about 71, about 71.5, about 72, about 72.5, about 73, about 73.5, about 74, about 74.5, about 75, about 75.5, about 76, about 76.5, about 77, about 77.5, about 78, about 78.5, about 79, about 79.5, about 80, about 80.5, about 81, about 81.5, about 82, about 82.5, about 83, about 83.5, about 84, about 84.5, about 85, about 85.5, about 86, about 86.5, about 87, about 87.5, about 88, about 88.5, about 89, about 89.5, about 90, about 90.5, about 91, about 91.5, about 92, about 92.5, about 93, about 93.5, about 94, about 94.5, about 95, about 95.5, about 96, about 96.5, about 97, about 97.5, about 98, about 98.5, about 99, about 99.5, about 100, about 100.5, about 101, about 101.5, about 102, about 102.5, about 103, about 103.5, about 104, about 104.5, about 105, about 105.5, about 106, about 106.5, about 107, about 107.5, about 108, about 108.5, about 109, about 109.5, about 110, about 110.5, about 111, about 111.5, about 112, about 112.5, about 113, about 113.5, about 114, about 114.5, about 115, about 115.5, about 116, about 116.5, about 117, about 117.5, about 118, about 118.5, about 119, about 119.5, about 120, about 120.5, about 121, about 121.5, about 122, about 122.5, about 123, about 123.5, about 124, about 124.5, about 125, about 125.5, about 126, about 126.5, about 127, about 127.5, about 128, about 128.5, about 129, about 129.5, about 130, about 130.5, about 131, about 131.5, about 132, about 132.5, about 133, about 133.5, about 134, about 134.5, about 135, about 135.5, about 136, about 136.5, about 137, about 137.5, about 138, about 138.5, about 139, about 139.5, about 140, about 140.5, about 141, about 141.5, about 142, about 142.5, about 143, about 143.5, about 144, about 144.5, about 145, about 145.5, about 146, about 146.5, about 147, about 147.5, about 148, about 148.5, about 149, about 149.5, about 150, about 150.5, about 151, about 151.5, about 152, about 152.5, about 153, about 153.5, about 154, about 154.5, about 155, about 155.5, about 156, about 156.5, about 157, about 157.5, about 158, about 158.5, about 159, about 159.5, about 160, about 160.5, about 161, about 161.5, about 162, about 162.5, about 163, about 163.5, about 164, about 164.5, about 165, about 165.5, about 166, about 166.5, about 167, about 167.5, about 168, about 168.5, about 169, about 169.5, about 170, about 170.5, about 171, about 171.5, about 172, about 172.5, about 173, about 173.5, about 174, about 174.5, about 175, about 175.5, about 176, about 176.5, about 177, about 177.5, about 178, about 178.5, about 179, about 179.5, about 180, about 180.5, about 181, about 181.5, about 182, about 182.5, about 183, about 183.5, about 184, about 184.5, about 185, about 185.5, about 186, about 186.5, about 187, about 187.5, about 188, about 188.5, about 189, about 189.5, about 190, about 190.5, about 191, about 191.5, about 192, about 192.5, about 193, about 193.5, about 194, about 194.5, about 195, about 195.5, about 196, about 196.5, about 197, about 197.5, about 198, about 198.5, about 199, about 199.5, or about 200 g of amino acids.

In one embodiment, the amount of amino acids in a dose is dependent upon the body mass of a subject receiving the dose. In another embodiment, the amount of amino acids in a dose is dependent on the duration of hemodialysis. In another embodiment, the amount of amino acids in a dose is dependent upon the body mass of a subject receiving the dose and the duration of hemodialysis. In another embodiment, a dose comprises less than about 2 g of amino acids per kg of body mass of the subject. In another embodiment, a dose comprises a mass of amino acids from about 120% to about 160% the body mass of a subject on a (g/kg) basis. Non-limiting examples follow. In one non-limiting example, a subject with a body mass between about 34 and about 39 kg receives a dose comprising about 51 g of amino acids. In one non-limiting example, a subject with a body mass between about 40 and about 44 kg receives a dose comprising about 60 g of amino acids. In one non-limiting example, a subject with a body mass between about 45 and about 51 kg receives a dose comprising about 68 g of amino acids. In one non-limiting example, a subject with a body mass between about 52 and about 59 kg receives a dose comprising about 78 g of amino acids. In one non-limiting example, a subject with a body mass between about 60 and about 69 kg receives a dose comprising about 90 g of amino acids. In one non-limiting example, a subject with a body mass of about 70 kg, or greater, receives a dose comprising about 105 g of amino acids, or greater. In one embodiment the duration of hemodialysis is between 2-4.5 hrs. In one embodiment the duration of hemodialysis is between 2.75-4 hrs.

In one embodiment, an IDPN composition comprises one or more lipids. In another embodiment, a lipid is provided in the form of an emulsion. In another embodiment, a lipid is provided in the form of an emulsion of purified vegetable oil from soybean. In another embodiment, an emulsion of purified vegetable oil from soybean is Intralipid® (Kabi Vitrum). In another embodiment, an emulsion of purified vegetable oil from soybean comprises Travamulsion® (Travenol). In another embodiment, an emulsion of purified vegetable oil from soybean comprises egg phospholipids and soybean oil. In another embodiment, an emulsion of purified vegetable oil from soybean comprises soybean oil, egg yolk phospholipids, glycerin, water, and sodium hydroxide. In another embodiment, an emulsion of purified vegetable oil from soybean comprises phytosterols. In another embodiment, a lipid is provided in the form of an emulsion of purified safflower oil. In another embodiment, an emulsion of purified safflower oil is Liposyn® (Abbott). In another embodiment, an emulsion of purified safflower oil comprises safflower oil, soybean oil, egg phosphatides, glycerin, water, and sodium hydroxide. In another embodiment, a lipid is provided in the form of an emulsion of purified fish oil. In another embodiment, an emulsion of purified fish oil is Omegaven* (Fresenius AG). In another embodiment, a lipid is provided in the form of an emulsion of purified olive oil. In another embodiment, a lipid is provided in the form of an emulsion of medium-chain triglyceride oil. In another embodiment, a lipid is provided in the form of an emulsion of two or more of soybean oil, safflower oil, fish oil, olive oil and medium-chain triglyceride oil. In another embodiment, the lipid is 50% soybean oil and 50% safflower oil. In another embodiment, the lipid is 50% soybean oil and 50% medium-chain triglyceride oil. In another embodiment, the lipid is 40% soybean oil, 50% medium-chain triglyceride oil, and 10% fish oil. In another embodiment, the lipid is 25% soybean oil and 75% medium-chain triglyceride. In another embodiment, the lipid is 20% soybean oil and 80% olive oil. In another embodiment, a lipid comprises a triglyceride comprising three fatty acid residues. In another embodiment, a lipid comprises a triglyceride comprising saturated and/or unsaturated fatty acid residues. In another embodiment, a fatty acid residue is derived from linoelic acid, oleic acid, palmitic acid, or steric acid. In another embodiment, a fatty acid residue is derived from eicosapentaenoic acid, arachidonic acid or docosahexaeneoic acid. In another embodiment, a lipid comprises a phospholipid. In another embodiment, an IDPN composition comprises about 5 to about 30% lipids by volume. In another embodiment, a composition comprises about 10 to about 20% lipids by volume. In another embodiment, an IDPN composition comprises lipids and propofol. In another embodiment, an IDPN composition comprises lipids, propofol, and a cyclodrtrin, a cyclodextrin analogue, or a pharmaceutically-acceptable salt of cyclodextrin. In another embodiment, a composition does not comprise a lipid. In another embodiment, a composition that does not comprise a lipid is administered to a subject comprising hyperlipemia, acute pancreatitis, lipid nephrosis or allergic reactions to eggs.

In one embodiment, a dose comprises between about 5 and about 50 g of lipids. In another embodiment, a dose comprises between about 5 and about 30 g of lipids. In another embodiment, a dose comprises between about 10 and about 25 g of lipids. In another embodiment, a dose comprises more than about 5 g of lipids. In another embodiment, a dose comprises less than about 50 g of lipids. In another embodiment, a dose comprises about 5 g, about 6 g, about 7 g, about 8 g, about 9 g, about 10 g, about 11 g, about 12 g, about 13 g, about 14 g, about 15 g, about 16 g, about 17 g, about 18 g, about 19 g, about 20 g, about 21 g, about 22 g, about 23 g, about 24 g, about 25 g, about 26 g, about 27 g, about 28 g, about 29 g, about 30 g, about 31 g, about 32 g, about 33 g, about 34 g, about 35 g, about 36 g, about 37 g, about 38 g, about 39 g, about 40 g, about 41 g, about 42 g, about 43 g, about 44 g, about 45 g, about 46 g, about 47 g, about 48 g, about 49 g, or about 50 g of lipids.

In one embodiment, the amount of lipids in a dose is dependent upon the body mass of a subject receiving the dose. In another embodiment, the amount of lipids in a dose is dependent on the duration of hemodialysis. In another embodiment, the amount of lipids in a dose is dependent upon the body mass of a subject receiving the dose and the duration of hemodialysis. In another embodiment, a dose comprises less than about 0.4 g of lipids per kg of body mass of the subject. In another embodiment, a dose comprises a mass of lipids from about 10% to about 40% the body mass of a subject on a (g/kg) basis. In another embodiment, a dose comprises a mass of lipids from about 20% to about 30% the body mass of a subject on a (g/kg) basis. Non-limiting examples follow. In one non-limiting example, a subject with a body mass between about 34 and about 39 kg receives a dose comprising about 8.6 g of lipids. In one non-limiting example, a subject with a body mass between about 40 and about 44 kg receives a dose comprising about 10.2 g of lipids. In one non-limiting example, a subject with a body mass between about 45 and about 51 kg receives a dose comprising about 11.2 g of lipids. In one non-limiting example, a subject with a body mass between about 52 and about 59 kg receives a dose comprising about 13.2 g of lipids. In one non-limiting example, a subject with a body mass between about 60 and about 69 kg receives a dose comprising about 15.2 g of lipids. In one non-limiting example, a subject with a body mass of about 70 kg, or greater, receives a dose comprising about 17.8 g of lipids, or greater. In one embodiment the duration of hemodialysis is between 2-4.5 hrs. In one embodiment the duration of hemodialysis is between 2.75-4 hrs.

In one embodiment, the presence of a lipid improves the ability of an IDPN composition to increase albumin levels in a subject. In another embodiment, the presence of a lipid does not improve the ability of an IDPN composition to increase albumin levels in a subject. In another embodiment, the presence of a lipid increases the nutritional value of an IDPN composition. In another embodiment, the presence of a lipid increases the caloric content of an IDPN composition. In another embodiment, an IDPN composition comprising a lipid has higher nutritional value than an IDPN composition that does not comprise a lipid. In another embodiment, an IDPN composition comprising a lipid has higher caloric content than an IDPN composition that does not comprise a lipid. In one embodiment, a subject being administered an IDPN composition with a low caloric content does not catabolize the amino acids of the IDPN composition. In one embodiment, a subject being administered an IDPN composition with a low caloric content catabolizes the amino acids of the IDPN composition. In one embodiment, a subject being administered an IDPN composition with a low caloric content catabolizes the amino acids of the IDPN composition, thereby diminishing the increase in albumin levels. In one embodiment, a subject being administered an IDPN composition that does not comprise lipids does not catabolize the amino acids of the IDPN composition. In one embodiment, a subject being administered an IDPN composition that does not comprise lipids catabolizes the amino acids of the IDPN composition. In one embodiment, a subject being administered an IDPN composition that does not comprise lipids catabolizes the amino acids of the IDPN composition, thereby diminishing the increase in albumin levels. In another embodiment, a subject being administered an IDPN composition with a high caloric content does not catabolize the amino acids of the IDPN composition. In another embodiment, a subject being administered an IDPN composition comprising a lipid does not catabolize the amino acids of the IDPN composition. In another embodiment, a subject being administered an IDPN composition with a high caloric content does not catabolize the amino acids of the IDPN composition, thereby enabling an increase in albumin levels. In another embodiment, a subject being administered an IDPN composition comprising a lipid does not catabolize the amino acids of the IDPN composition, thereby enabling an increase in albumin levels.

In one embodiment, an IDPN composition comprises one or more micronutrients. In another embodiment, an IDPN composition is co-administered with one or more micronutrients. In another embodiment, a micronutrient is a vitamin, a trace element, and/or a mineral. In another embodiment, a vitamin is a water soluble vitamin. In another embodiment, the vitamin is vitamin C, folic acid, vitamin $B_1$, or vitamin $B_6$. In another embodiment, a vitamin comprises a multivitamin lacking vitamin K. In another embodiment, a trace element comprises one or more of zinc, selenium, copper, chromium, magnesium, and manganese. In another embodiment, a mineral comprises a mineral salt. In another embodiment, a mineral salt comprises sodium phosphate, sodium chloride, sodium iodide, sodium acetate, potassium chloride, potassium iodide, potassium acetate, potassium metabisulfite, calcium acetate, magnesium acetate, or magnesium sulfate. In another embodiment, a mineral salt comprises a lithium, sodium, potassium, calcium, magnesium, aluminum, zinc, cesium, scandium, titanium, zirconium, hafnium, vanadium, chromium, molybdenum, manganese, iron, ruthenium, osmium, cobalt, rhenium, iridium, nickel, palladium, platinum, copper, silver, gold, cadmium, mercury, indium, tin, lead, bismuth, cerium, samarium, or strontium salt, or a combination of any of the forgoing. In another embodiment, a mineral salt comprises a fluoride, chloride, bromide, iodide, nitrate, nitrite, phosphate, sulfate, sulfite, bisulfite, thiosulfate, carbonate, bicarbonate, chlorate, perchlorate, chlorite, or hypochlorite salt, or a combination of any of the forgoing.

In one embodiment, an IDPN composition comprises one or more pharmaceutical agents. One non-limiting example of a pharmaceutical agent appropriate for inclusion in an IDPN composition is insulin. In another embodiment, insulin is added to an IDPN composition prior to administration to the subject. In another embodiment, the addition of insulin to an IDPN composition in a container takes place immediately prior to administration to prevent absorption of the insulin by a container material. In another embodiment, insulin is co-administered with an IDPN composition. In another embodiment, the insulin is subcutaneously injected during treatment with an IDPN composition. In another embodiment, about 5 to about 20 units of insulin is added with one dose of an IDPN composition.

In one embodiment, an IDPN composition is co-administered with one or more pharmaceutical agents. In another embodiment, co-administration of a pharmaceutical agent takes place prior to administration of an IDPN composition. In another embodiment, co-administration of a pharmaceutical agent takes place during administration of an IDPN composition. In another embodiment, co-administration of a pharmaceutical agent takes place after administration of an IDPN composition. Non-limiting examples of pharmaceutical agents that are co-administered with an IDPN composition include: an erythropoietin agent, for example, Procrit®, Epogen®, ARANESP® or epoietin alpha; and iron agent, for example, InFeD®, Ferrlecit® and Venofer®; a phosphorous binder, for example, PhosLo® (calcium acetate), Tums® (calcium carbonate), Renagel® (sevelamer), and Fosrenol® (lanthanum carbonate); an active vitamin D agent, for example, Rocaltrol® (calcitriol) and Hectorol® (doxercalciferol); Zemplar® (paricalcitol), Calcijex® (calcitrol), and Sensipar® (cinacalcet); vitamin complex agents, for example, Nephro-Vite®, Nephrocaps® and Nephroplex®; an antihistamine, for example, Benadryl® (diphenhydramine), Atarax® or Vistaril® (hydroxyzine), and Zyrtec® (loratadine); and a statin, for example, Lipitor® (Atorvastatin), Zocor® (Simvastatin), and Pravachol® (Pravastatin).

In one embodiment, an IDPN composition is administered with a fill. In another embodiment, a fill comprises water. In another embodiment, a fill comprises sterile water. In another embodiment, a fill consists of sterile water. In another embodiment, a fill comprises saline. In another embodiment, a fill consists of saline. In another embodiment, a fill comprises physiological saline. In another embodiment, a fill consists of physiological saline. In another embodiment, a fill comprises an IDPN composition. In another embodiment, a fill consists of an IDPN composition. In another embodiment, a fill comprises an IDPN composition that is administered with the fill. In another embodiment, a fill consists of an IDPN composition that is administered with the fill. In another embodiment, a fill has a volume of greater than about 1 mL. In another embodiment, a fill has a volume of greater than about 10 mL. In another embodiment, a fill has a volume of less than about 200 mL. In another embodiment, a fill has a volume of less than about 150 mL. In another embodiment, a fill has a volume of from about 1 mL to about 200 mL. In another embodiment, a fill has a volume of from about 10 mL to about 100 mL. In another embodiment, a fill has a volume of from about 25 mL to about 75 mL. In another embodiment, a fill has a volume of from about 40 mL to about 60 mL. In another embodiment, a fill has a volume greater than about 25 ml. In another embodiment, a fill has a volume less than about 75 mL. In another embodiment, a fill has a volume of about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, about 95 mL, about 100 mL, about 105 mL, about 110 mL, about 115, mL, about 120 mL, about 125 mL, about 130 mL, about 135 mL, about 140 mL, about 145 mL, or about 150 mL. In another embodiment, a fill has a volume of about 50 mL.

In one embodiment, an IDPN composition is administered simultaneously with a fill. In another embodiment, an IDPN composition is administered after a fill is administered. In another embodiment, a fill is used to prime a dialysis tubing. In another embodiment, a fill is administered to a subject. In another embodiment, a fill is not administered to a subject. In another embodiment, a fill is premixed with an IDPN composition.

In one embodiment, an IDPN composition comprises an amount of a stock carbohydrate solution and an amount of an amino acid stock mixture. In another embodiment, an IDPN composition comprises an amount of a stock carbohydrate solution and an amount of an amino acid stock solution. In another embodiment, an IDPN composition comprises a volume of a stock carbohydrate solution and a volume of an amino acid stock mixture. In another embodiment, an IDPN composition comprises a volume of a stock carbohydrate solution and a volume of an amino acid stock solution. In another embodiment, an IDPN composition further comprises a fill. In another embodiment, an IDPN composition further comprises an amount of a fill. In another embodiment, an IDPN composition further comprises a volume of a fill.

In one embodiment, an IDPN composition comprises an amount of a stock carbohydrate solution, an amount of an amino acid stock mixture, and an amount of a fill. In another embodiment, an IDPN composition comprises an amount of a stock carbohydrate solution, an amount of an amino acid stock solution, and an amount of a fill. In another embodiment, an IDPN composition comprises a volume of a stock carbohydrate solution, a volume of an amino acid stock mixture, and a volume of a fill. In another embodiment, an IDPN composition comprises a volume of a stock carbohydrate solution, a volume of an amino acid stock solution, and a volume of a fill.

IDPN Compositions Effective to Modulate Albumin Levels in a Subject

In one embodiment, an IDPN composition is effective to modulate albumin levels of a subject. In another embodiment, an IDPN composition is effective to increase albumin levels of a subject. In another embodiment, the modulation in albumin levels is relative to the amount of an IDPN composition administered to a subject. In another embodiment, a modulation in albumin levels is independent of the amount of an IDPN composition administered to a subject.

In one embodiment, a modulation in albumin levels is greater than about 0.01 g/dL. In another embodiment, a modulation in albumin levels is greater than about 0.05 g/dL. In another embodiment, a modulation in albumin levels is greater than about 0.1 g/dL. In another embodiment, a modulation in albumin levels is less than about 1.0 g/dL. In another embodiment, a modulation in albumin levels is less than about 0.8 g/dL. In another embodiment, a modulation in albumin levels is less than about 0.6 g/dL. In another embodiment, a modulation in albumin levels is from about 0.01 g/dL to about 1.0 g/dL. In another embodiment, a modulation in albumin levels is from about 0.05 g/dL to about 0.8 g/dL. In another embodiment, a modulation in albumin levels is from about 0.1 g/dL to about 0.6 g/dL. In another embodiment, a modulation in albumin levels is from about 0.2 g/dL to about 0.4 g/dL.

In one embodiment, a increase in albumin levels is greater than about 0.01 g/dL. In another embodiment, a increase in albumin levels is greater than about 0.05 g/dL. In another embodiment, a increase in albumin levels is greater than about 0.1 g/dL. In another embodiment, a increase in albumin levels is less than about 1.0 g/dL. In another embodiment, a increase in albumin levels is less than about 0.8 g/dL. In another embodiment, a increase in albumin levels is less than about 0.6 g/dL. In another embodiment, a increase in albumin levels is from about 0.01 g/dL to about 1.0 g/dL. In another embodiment, a increase in albumin levels is from about 0.05 g/dL to about 0.8 g/dL. In another embodiment, a increase in albumin levels is from about 0.1 g/dL to about 0.6 g/dL. In another embodiment, a increase in albumin levels is from about 0.2 g/dL to about 0.4 g/dL.

In one embodiment, a modulation in albumin levels is greater than about 1%. In another embodiment, a modulation in albumin levels is greater than about 5%. In another embodiment, a modulation in albumin levels is greater than about 10%. In another embodiment, a modulation in albumin levels is greater than about 25%. In another embodiment, a modulation in albumin levels is greater than about 50%. In another embodiment, a modulation in albumin levels is greater than about 100%. In another embodiment, a modulation in albumin levels is less than about 100%. In another embodiment, a modulation in albumin levels is less than about 50%. In another embodiment, a modulation in albumin levels is less than about 25%. In another embodiment, a modulation in albumin levels is less than about 10%. In another embodiment, a modulation in albumin levels is less than about 5%. In another embodiment, a modulation in albumin levels is less than about 1%. In another embodiment, a modulation in albumin levels is from about 1% to about 100%. In another embodiment, a modulation in albumin levels is from about 5% to about 50%. In another embodiment, a modulation in albumin levels is from about 10% to about 50%. In another embodiment, a modulation in albumin levels is from about 25% to about 50%. In another embodiment, a modulation in albumin levels is about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In one embodiment, an increase in albumin levels is greater than about 1%. In another embodiment, an increase in albumin levels is greater than about 5%. In another embodiment, an increase in albumin levels is greater than about 10%. In another embodiment, an increase in albumin levels is greater than about 25%. In another embodiment, an increase in albumin levels is greater than about 50%. In another embodiment, an increase in albumin levels is greater than about 100%. In another embodiment, an increase in albumin levels is less than about 100%. In another embodiment, an increase in albumin levels is less than about 50%. In s one embodiment, an increase in albumin levels is less than about 25%. In another embodiment, an increase in albumin levels is less than about 10%. In another embodiment, an increase in albumin levels is less than about 5%. In another embodiment, an increase in albumin levels is less than about 1%. In another embodiment, an increase in albumin levels is from about 1% to about 100%. In another embodiment, an increase in albumin levels is from about 5% to about 50%. In another embodiment, an increase in albumin levels is from about 10% to about 50%. In another embodiment, an increase in albumin levels is from about 25% to about 50%. In another embodiment, an increase in albumin levels is about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In one embodiment, a modulation in albumin levels is observable within about an hour, within about 4 hours, within about 8 hours, within about 12 hours, within about 24 hours, within about 2 days, within about 3 days, within about 4 days, within about 5 days, within about 6 days, or within about 7 days. In another embodiment, a modulation in albumin levels is observable within about a month, within about 2 months, within about 3 months, within about 4 months, within about 5 months, within about 6 months, within about 7 months, within about 8 months, within about 9 months, within about 10 months, within about 11 months, or within about 12 months. In another embodiment, a modulation in albumin levels is observable within about 6 months. In another embodiment, a modulation in albumin levels is observable within about a year.

In one embodiment, an increase in albumin levels is observable within about an hour, within about 4 hours, within about 8 hours, within about 12 hours, within about 24 hours, within about 2 days, within about 3 days, within about 4 days, within about 5 days, within about 6 days, or within about 7 days. In another embodiment, an increase in albumin levels is observable within about a month, within about 2 months, within about 3 months, within about 4 months, within about 5 months, within about 6 months, within about 7 months, within about 8 months, within about 9 months, within about 10 months, within about 11 months, or within about 12 months. In another embodiment, an increase in albumin levels is observable within about 6 months. In another embodiment, an increase in albumin levels is observable within about a year.

In one embodiment, therapy continues until a desired increase in albumin levels is observed in a subject. In another embodiment, a desired increase in albumin levels is greater than about 0.05 g/dL. In another embodiment, a desired increase in albumin levels is greater than about 0.1 g/dL. In another embodiment, a desired increase in albumin levels is less than about 1.0 g/dL. In another embodiment, a desired increase in albumin levels is less than about 0.6 g/dL. In another embodiment, a desired increase in albumin levels is from about 0.05 to about 1.0 g/dL. In another embodiment, a desired increase in albumin levels is from about 0.1 to about 0.6 g/dL. In another embodiment, a desired increase in albumin levels is from about 0.2 to about 0.4 g/dL. In another embodiment, a desired increase in albumin levels is about 0.05, about 0.10, about 0.15, about 0.20, about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, or about 1.00 g/dL.

In one embodiment, therapy continues until a desired albumen level in a subject is reached. In another embodiment, a desired albumin level is greater than about 3.5 g/dL. In another embodiment, a desired albumin level is less than about 4.0 g/dL. In another embodiment, a desired albumin level is from about 3.5 to about 4.0 g/dL. In another embodiment, a desired albumin level is about 3.5, about 3.55, about 3.6, about 3.65, about 3.7, about 3.75, about 3.8, about 3.85, about 3.9, about 3.95, or about 4.0 g/dL. In another embodiment, a desired albumin level is about 3.8 g/dL.

In one embodiment, an IDPN composition is co-administered with one or more agents effective to increase albumin levels in a subject. In another embodiment, an IDPN composition is co-administered with one or more appetite stimulants. Non-limiting examples of appetite stimulants include marinol, cyrohepatadine, megestrol acetate, and pizotifen. In another embodiment, an IDPN composition is co-administered with megestrol acetate.

Administration of IDPN Compositions

In one embodiment, an IDPN composition is administered weekly. In another embodiment, an IDPN composition is administered daily. In another embodiment, an IDPN composition is administered at least once a day. In another embodiment, an IDPN composition is administered more than once a day. In another embodiment, an IDPN composition is administered 1, 2, 3, 4, 5, 6, or 7 times a week. In another embodiment, an IDPN composition is administered 3 days a week. In another embodiment, an IDPN composition is administered 2 days a week. In another embodiment, an IDPN composition is administered 1, 2, 3, 4, 5, 6, 7, 8, 9, or 10 times a day. In another embodiment, an IDPN composition is administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 times a week. In another embodiment, an IDPN composition is administered from about 1 to about 10 times a day. In another embodiment, an IDPN composition is administered from about 1 to about 5 times a day. In another embodiment, an IDPN composition is administered 1 to 3 times a day. In another embodiment, an IDPN composition is administered about 1 to about 100 times a week. In another embodiment, an IDPN composition is administered about 5 to about 50 times a week. In another embodiment, an IDPN composition is administered about 7 to about 35 times a week. In another embodiment, an IDPN composition is administered about 7 to about 21 times a week. In another embodiment, the administrations are spread out evenly over a time period. In another embodiment, an IDPN composition is administered as needed. In another embodiment, an IDPN composition is administered at the discretion of a health care provider. In another embodiment, IDPN compositions are administered as per a regimen.

In one embodiment, a dose is administered over an infusion time. In another embodiment, an infusion time is less than about 8 hours. In another embodiment, an infusion time is less than about 6 hours. In another embodiment, an infusion time is less than about 4 hours. In another embodiment, an infusion time is less than about 2 hours. In another embodiment, an infusion time is from about 2 hours to about 8 hours. In another embodiment, an infusion time is from about 3 hours to about 5 hours. In another embodiment, an infusion time is about 2 hours, about 2.25 hours, about 2.5 hours, about 2.75 hours, about 3 hours, about 3.25 hours, about 3.5 hours, about 3.75 hours, or about 4 hours. In another embodiment, an infusion time is about 2.75-3 hours. In another embodiment, an infusion time is about 3-3.25 hours. In another embodiment, an infusion time is about 3.25-3.5 hours. In another embodiment, an infusion time is about 3.5-3.75 hours. In another embodiment, an infusion time is about 3.75-4 hours.

In one embodiment, an infusion time is optionally extended by an additional period. In another embodiment, an infusion time is extended by an additional period. In another embodiment, an additional period improves the efficacy of infusion of an IDPN composition into the subject. In another embodiment, an additional period precedes the infusion time. In another embodiment, an additional period follows the infusion time. In another embodiment, an infusion time is interrupted by one or more additional periods. In another embodiment, an additional period is greater than about 0.05 hours. In another embodiment, an additional period is greater than about 0.20 hours. In another embodiment, an additional period is less than about 1.0 hours. In another embodiment, an additional period is less than about 0.55 hours. In another embodiment, an additional period is from about 0.05 hours to about 1.0 hours. In another embodiment, an additional period is from about 0.10 hours to about 0.50 hours. In another embodiment, an additional period is about 0.05 hours, about 0.10 hours, about 0.15 hours, about 0.20 hours, about 0.25 hours, about 0.30 hours, about 0.35 hours, about 0.40 hours, about 0.45 hours, or about 0.50 hours. In another embodiment, an additional period is about 0.25 hours. In another embodiment, an additional period follows an infusion time and is 0.25 hours.

In one embodiment, an infusion time is about 2.00 hours extended by an additional period of about 0.25 hours. In another embodiment, an infusion time is about 2.25 hours extended by an additional period of about 0.25 hours. In another embodiment, an infusion time is about 2.50 hours extended by an additional period of about 0.25 hours. In another embodiment, an infusion time is about 2.75 hours extended by an additional period of about 0.25 hours. In another embodiment, an infusion time is about 3.00 hours extended by an additional period of about 0.25 hours. In another embodiment, an infusion time is about 3.25 hours extended by an additional period of about 0.25 hours. In another embodiment, an infusion time is about 3.50 hours extended by an additional period of about 0.25 hours. In another embodiment, an infusion time is about 3.75 hours extended by an additional period of about 0.25 hours. In another embodiment, an infusion time is about 4.00 hours extended by an additional period of about 0.25 hours. In another embodiment, an infusion time is about 2.00 hours extended by an additional period of about 0.50 hours. In another embodiment, an infusion time is about 2.25 hours extended by an additional period of about 0.50 hours. In another embodiment, an infusion time is about 2.50 hours extended by an additional period of about 0.50 hours. In another embodiment, an infusion time is about 2.75 hours extended by an additional period of about 0.50 hours. In another embodiment, an infusion time is about 3.00 hours extended by an additional period of about 0.50 hours. In another embodiment, an infusion time is about 3.25 hours extended by an additional period of about 0.50 hours. In another embodiment, an infusion time is about 3.50 hours extended by an additional period of about 0.50 hours. In another embodiment, an infusion time is about 3.75 hours extended by an additional period of about 0.50 hours. In another embodiment, an infusion time is about 4.00 hours extended by an additional period of about 0.50 hours.

In one embodiment, a dose is administered at an infusion rate. In another embodiment, an infusion rate is directly proportionate to the body mass of the subject. In another embodiment, an infusion rate is modulated as therapy progresses for a subject. In another embodiment an infusion rate during the second week of therapy is greater than an infusion rate during the first week of therapy for a given subject. In another embodiment, an infusion rate during the second week of therapy is about 1.5 times greater than an infusion rate during the first week of therapy for a given subject. In another embodiment, an infusion rate during the second week of therapy is about 2 times greater than an infusion rate during the first week of therapy for a given subject. In another embodiment, an infusion rate during the second week of therapy is about 3 times greater than an infusion rate during the first week of therapy for a given subject.

In one embodiment, an infusion rate is greater than about 10 mL/hour. In another embodiment, an infusion rate is less than about 300 mL/hour. In another embodiment, an infusion rate is from about 10 mL/hour to about 300 mL/hour. In another embodiment, an infusion rate is about 10 mL/hour, about 11 mL/hour, about 12 mL/hour, about 13 mL/hour, about 14 mL/hour, about 15 mL/hour, about 16 mL/hour, about 17 mL/hour, about 18 mL/hour, about 19 mL/hour, about 20 mL/hour, about 21 mL/hour, about 22 mL/hour, about 23 mL/hour, about 24 mL/hour, about 25 mL/hour, about 26 mL/hour, about 27 mL/hour, about 28 mL/hour, about 29 mL/hour, about 30 mL/hour, about 31 mL/hour, about 32 mL/hour, about 33 mL/hour, about 34 mL/hour, about 35 mL/hour, about 36 mL/hour, about 37 mL/hour, about 38 mL/hour, about 39 mL/hour, about 40 mL/hour, about 41 mL/hour, about 42 mL/hour, about 43 mL/hour, about 44 mL/hour, about 45 mL/hour, about 46 mL/hour, about 47 mL/hour, about 48 mL/hour, about 49 mL/hour, about 50 mL/hour, 51 mL/hour, about 52 mL/hour, about 53 mL/hour, about 54 mL/hour, about 55 mL/hour, about 56 mL/hour, about 57 mL/hour, about 58 mL/hour, about 59 mL/hour, about 60 mL/hour, about 61 mL/hour, about 62 mL/hour, about 63 mL/hour, about 64 mL/hour, about 65 mL/hour, about 66 mL/hour, about 67 mL/hour, about 68 mL/hour, about 69 mL/hour, about 70 mL/hour, about 71 mL/hour, about 72 mL/hour, about 73 mL/hour, about 74 mL/hour, about 75 mL/hour, about 76 mL/hour, about 77 mL/hour, about 78 mL/hour, about 79 mL/hour, about 80 mL/hour, about 81 mL/hour, about 82 mL/hour, about 83 mL/hour, about 84 mL/hour, about 85 mL/hour, about 86 mL/hour, about 87 mL/hour, about 88 mL/hour, about 89 mL/hour, about 90 mL/hour, about 91 mL/hour, about 92 mL/hour, about 93 mL/hour, about 94 mL/hour, about 95 mL/hour, about 96 mL/hour, about 97 mL/hour, about 98 mL/hour, about 99 mL/hour, about 100 mL/hour, about 101 mL/hour, about 102 mL/hour, about 103 mL/hour, about 104 mL/hour, about 105 mL/hour, about 106 mL/hour, about 107 mL/hour, about 108 mL/hour, about 109 mL/hour, about 110 mL/hour, about 111 mL/hour, about 112 mL/hour, about 113 mL/hour, about 114 mL/hour, about 115 mL/hour, about 116 mL/hour, about 117 mL/hour, about 118 mL/hour, about 119 mL/hour, about 120 mL/hour, about 121 mL/hour, about 122 mL/hour, about 123 mL/hour, about 124 mL/hour, about 125 mL/hour, about 126 mL/hour, about 127 mL/hour, about 128 mL/hour, about 129 mL/hour, about 130 mL/hour, about 131 mL/hour, about 132 mL/hour, about 133 mL/hour, about 134 mL/hour, about 135 mL/hour, about 136 mL/hour, about 137 mL/hour, about 138 mL/hour, about 139 mL/hour, about 140 mL/hour, about 141 mL/hour, about 142 mL/hour, about 143 mL/hour, about 144 mL/hour, about 145 mL/hour, about 146 mL/hour, about 147 mL/hour, about 148 mL/hour, about 149 mL/hour, about 150 mL/hour, about 151 mL/hour, about 152 mL/hour, about 153 mL/hour, about 154 mL/hour, about 155 mL/hour, about 156 mL/hour, about 157 mL/hour, about 158 mL/hour, about 159 mL/hour, about 160 mL/hour, about 161 mL/hour, about 162 mL/hour, about 163 mL/hour, about 164 mL/hour, about 165 mL/hour, about 166 mL/hour, about 167 mL/hour, about 168 mL/hour, about 169 mL/hour, about 170 mL/hour, about 171 mL/hour, about 172 mL/hour, about 173 mL/hour, about 174 mL/hour, about 175 mL/hour, about 176 mL/hour, about 177 mL/hour, about 178 mL/hour, about 179 mL/hour, about 180 mL/hour, about 181 mL/hour, about 182 mL/hour, about 183 mL/hour, about 184 mL/hour, about 185 mL/hour, about 186 mL/hour, about 187 mL/hour, about 188 mL/hour, about 189 mL/hour, about 190 mL/hour, about 191 mL/hour, about 192 mL/hour, about 193 mL/hour, about 194 mL/hour, about 195 mL/hour, about 196 mL/hour, about 197 mL/hour, about 198 mL/hour, about 199 mL/hour, about 200 mL/hour, about 201 mL/hour, about 202 mL/hour, about 203 mL/hour, about 204 mL/hour, about 205 mL/hour, about 206 mL/hour, about 207 mL/hour, about 208 mL/hour, about 209 mL/hour, about 210 mL/hour, about 211 mL/hour, about 212 mL/hour, about 213 mL/hour, about 214 mL/hour, about 215 mL/hour, about 216 mL/hour, about 217 mL/hour, about 218 mL/hour, about 219 mL/hour, about 220 mL/hour, about 221 mL/hour, about 222 mL/hour, about 223 mL/hour, about 224 mL/hour, about 225 mL/hour, about 226 mL/hour, about 227 mL/hour, about 228 mL/hour, about 229 mL/hour, about 230 mL/hour, about 231 mL/hour, about 232 mL/hour, about 233 mL/hour, about 234 mL/hour, about 235 mL/hour, about 236 mL/hour, about 237 mL/hour, about 238 mL/hour, about 239 mL/hour, about 240 mL/hour, about 241 mL/hour, about 242 mL/hour, about 243 mL/hour, about 244 mL/hour, about 245 mL/hour, about 246 mL/hour, about 247 mL/hour, about 248 mL/hour, about 249 mL/hour, about 250 mL/hour, about 251 mL/hour, about 252 mL/hour, about 253 mL/hour, about 254 mL/hour, about 255 mL/hour, about 256 mL/hour, about 257 mL/hour, about 258 mL/hour, about 259 mL/hour, about 260 mL/hour, about 261 mL/hour, about 262 mL/hour, about 263 mL/hour, about 264 mL/hour, about 265 mL/hour, about 266 mL/hour, about 267 mL/hour, about 268 mL/hour, about 269 mL/hour, about 270 mL/hour, about 271 mL/hour, about 272 mL/hour, about 273 mL/hour, about 274 mL/hour, about 275 mL/hour, about 276 mL/hour, about 277 mL/hour, about 278 mL/hour, about 279 mL/hour, about 280 mL/hour, about 281 mL/hour, about 282 mL/hour, about 283 mL/hour, about 284 mL/hour, about 285 mL/hour, about 286 mL/hour, about 287 mL/hour, about 288 mL/hour, about 289 mL/hour, about 290 mL/hour, about 291 mL/hour, about 292 mL/hour, about 293 mL/hour, about 294 mL/hour, about 295 mL/hour, about 296 mL/hour, about 297 mL/hour, about 298 mL/hour, about 299 mL/hour, or about 300 mL/hour.

In one embodiment, a modulation in albumin levels is determined by analyzing the blood of a subject. In another embodiment, an increase in albumin levels is determined by analyzing the blood of a subject.

In one embodiment, hemodialysis with an IDPN composition provides an IDPN composition with reduced infusion volume. In another embodiment, reduced infusion volume reduces one or more side effects associated with a high infusion volume. In another embodiment, a side effect associated with a high infusion volume is dyspnea, increased respiratory rate, rhonchi, edema, hypertension, hernia, or anxiety. In another embodiment, hemodialysis with an IDPN composition provides an IDPN composition with reduced symptoms associated with hyperglycemia. In another embodiment, a symptom associated with hyperglycemia is excessive thirst, excessive urination, physical exhaustion, involuntary weight loss, yeast or fungal infection, blurred vision, numbness, confusion, coma, or a symptom associated with diabetes type 2. In another embodiment, a symptom associated with diabetes type 2 is skin rash, skin infection, athlete's foot, poor skin healing, urinary tract infection, candida, thrush, dry itchy skin, flaky skin, skin ulcers, peripheral neuropathy, paresthesias, foot tingling, foot numbness, hand tingling, hand numbness, blurred vision, sexual dysfunction, erectile failure, vaginal dryness, premature menopause, absent periods, involuntary weight gain, drowsiness, malaise, dehydration, bedwetting, excessive hunger, muscle cramps, muscle aches, headaches, irritability, fatigue, muscle weakness, acne, hyperglycemic hyperosmolar nonketoic syndrome, diabetic ketoacidosis, nausea, vomiting, respiratory difficulty, rapid pulse, or abdominal pain. In another embodiment, hemodialysis with an IDPN composition provides hemodialysis with reduced side effects associated with a high infusion volume and with reduced symptoms associated with hyperglycemia.

In another embodiment, an IDPN composition comprises one or more agents effective to increase albumin levels in a subject. In another embodiment, an IDPN composition is co-administered with one or more agents effective to increase albumin levels in a subject. In another embodiment, co-administration of an agent effective to increase albumin levels in a subject takes place prior to administration of an IDPN composition. In another embodiment, co-administration of an agent effective to increase albumin levels in a subject takes place during administration of an IDPN composition. In another embodiment, co-administration of an agent effective to increase albumin levels in a subject takes place after administration of an IDPN composition. In another embodiment, a subject treated with an IDPN composition is also treated with an appetite stimulant. In another embodiment, an IDPN composition is co-administered with one or more appetite stimulants. In another embodiment, co-administration of an appetite stimulant takes place prior to administration of an IDPN composition. In another embodiment, co-administration of an appetite stimulant takes place during administration of an IDPN composition. In another embodiment, co-administration of an appetite stimulant takes place after administration of an IDPN composition. Non-limiting examples of appetite stimulants include marinol, cyprohepatadine, megestrol acetate, and pizotifen. In another embodiment, an IDPN composition is co-administered with megestrol acetate.

In one embodiment, an IDPN composition is administered using a dialysis machine. Non-limiting examples of dialysis machines that are compatable with IDPN compositions of the instant invention include a Fresenius 2008 series, a B.Braun Dialog+, a Gambro Phoenix System, a Redy 2000, a Baxter SPS550/1550, an Althin 1000, an Althin Altratouch 1000, an Althin Tina, a Meridian, an Aurora system 1000, a NxStage System One with Pure Flow, and a Fresinius 2008K At Home.

A Fresinius 2008 series is characterized by a pliable venous drip chamber comprising beveled downspouts resulting in low turbulence and reduced foaming, reduced resistance to flow, thereby reducing the potential for clotting, and thick-walled kink-resistant blood tubing.

A B.Braun Dialog+ is characterized by a bicarbonate cartridge holder, and an UltraPureFluid-System and Diacap® Ultra pyrogen filter to produce pure dialysate thereby reducing the risk of contaminated dialysis fluid and complications arising from the same.

A Gambro Phoenix System is characterized by online mixing of sterile dry bicarbonate, bloodlines with low extracorporeal blood volume, simplified priming thereby eliminating the need to reverse the dialyzer, and the absence of a priming bucket.

A Redy 2000 is characterized by self-containment, portability, a built-in blood pump, and a built-in foam detector.

A Baxter SPS550/1550 is characterized by an internally regulated pressure of 70 Kpa (10 psi) after the inlet water pressure regulator, and 100 KPa (15 psi) after the proportioning pump pressure regulator.

An Althin 1000 is characterized by a pressure measurement that detects backfiltration, and an integrated intelligent single needle.

An Althin Altratouch 1000 is characterized by reliable monitoring of very low flow rates.

An Althin Tina is characterized by a hydraulic module that swings out of the body of the machine out on a door, and a small number of openings into the machine.

A Meridian is characterized by prevention of an excessive loss of water from the blood of a subject, the ability to function with a carbonate concentrate or an acetate concentrate, and automated chemical disinfection.

An Aurora system 1000 is characterized by prevention of an excessive loss of water from the blood of a subject, the ability to function with a carbonate concentrate or an acetate concentrate, and the ability to prepare dialysate from a concentrate.

A NxStage System One with Pure Flow is characterized by small size and portability, thereby enabling hemodialysis at home and during travel, compatibility with common household electrical and plumbing facilities, a compact water purification system, the ability to prepare dialysate from tap water thereby eliminating the need for a large external water purification system, and built-in water purity sensors.

A Fresenius 2008K At Home is characterized by enabling hemodialysis at home, a pliable venous drip chamber comprising beveled downspouts resulting in low turbulence and reduced foaming, reduced resistance to flow, thereby reducing the potential for clotting, and thick-walled kink-resistant blood tubing.

In one embodiment, administration comprises dialysis. In another embodiment, administration takes place in a health care facility. In another embodiment, administration takes place outside of a healthcare facility. In another embodiment, administration takes place in the home of the subject. In another embodiment, administration takes place in the home of the subject using a NxStage System One with Pure Flow dialysis machine.

In one embodiment, a dialysis machine comprises one or more blood lines. In another embodiment, a blood line is compatible with an IDPN composition. In another embodiment, a dialysis machine comprises a venous drip chamber. In another embodiment, a venous drip chamber comprises a pigtail In one embodiment, a hemodialysis system is composed of two major subsystems, a dialysate delivery system and an extracorporeal blood circuit. In another embodiment, an extracorporeal blood circuit is compatible with an IDPN composition. In another embodiment, an extracorporeal circuit comprises a venous drip chamber. In another embodiment the venous drip chamber comprises a venous medication infusion luer lock line. In another embodiment, a venous medication infusion luer lock line is an access port outside the human body. In another embodiment, a venous medication infusion luer lock line is compatible with IDPN composition. In another embodiment, an IDPN composition is administered to the subject via the venous medication infusion luer lock line. In another embodiment, an IDPN composition enters the blood of the subject via the venous medication infusion luer lock line. In another embodiment, the subjects blood travels through the venous portion of the extracorporeal circuit, and into the subjects body. In another embodiment, an IDPN composition is administered by a route other than the venous medication infusion luer lock line. In another embodiment, an IDPN composition is administered to a subject by a route other than a pigtail.

In one embodiment, an IDPN composition is administered to a dialysis subject. In another embodiment, a subject is suffering from malnutrition. In another embodiment, a subject is in need or want of nutrition. In another embodiment, a subject is in need or want of a therapy for malnutrition. In another embodiment, a dialysis subject suffering from malnutrition is identified by detecting: evidence of protein or energy malnutrition and inadequate dietary protein intake, evidence of the inability to administer or tolerate adequate oral nutrition inclusive of supplements and tube feeding, and evidence that the combination or oral and/or enteral intake when combined with an IDPN composition of the instant invention will meet the subject's nutritional needs.

Administration of an IDPN composition generally coincides with the start of hemodialysis on a subject. During IDPN composition administration, a subject is monitored for glucose tolerance, protein load and/or fat tolerance. Glucose monitoring includes blood glucose level before, during and after IDPN administration and monitoring a subject for symptoms of hyper or hypoglycemia. The symptoms of hyperglycemia include nausea, thirst, headache, vomiting and weakness. The symptoms of hypoglycemia include headache, dizziness, tremors, cold sweat, confusion, and faintness. The presence of hyper or hypoglycemia can then be confirmed through blood sugar analysis, such as via a fingerstick or arterial glucose level. In one embodiment, insulin is administered, thereby treating hyperglycemia. In one embodiment, a subject receives about 20 to about 30 g of simple carbohydrates orally, thereby treating hypoglycemia. Protein monitoring includes the monitoring of blood urea nitrogen (BUN) prior to dialysis and Kt/V, which is a measure of dialysis adequacy.

Fat monitoring includes a pre-dialysis triglyceride test prior to a lipid infusion and then another following the lipid infusion to ensure that the subject is clearing lipids from the bloodstream. In one embodiment, sodium, potassium, phosphorus and magnesium levels are monitored for the presence of refeeding syndrome.

In one embodiment, an IDPN composition is administered through a port post dialyzer of the dialysis machine being used to perform hemodialysis on the subject. In another embodiment, the administration is performed through the venous chamber of the dialysis machine. An IDPN composition is administered by any suitable method known to a practitioner of hemodialysis.

Hemodialysis in general uses diffusion to remove waste products from a subject blood. A diffusive gradient that occurs across a semi-permeable dialyzer between the blood and an electrolyte solution, called dialysate, causes diffusion. In one embodiment, the hemodialysis takes place in a health care facility. In another embodiment, the hemodialysis takes place in a clinic. In another embodiment, the hemodialysis takes place in a hospital. In another embodiment, the hemodialysis takes place in a dialysis unit. In one embodiment, the hemodialysis takes place in the home of the subject. In another embodiment, the dialysis machine is a home system. In another embodiment, a home system comprises a mobile cart and integral bag manager. In another embodiment, the dialysis machine accepts a dose of an IDPN composition. In another embodiment, the dialysis machine accepts multiple doses of an IDPN composition. In another embodiment, a dialysis machine accepts 1, 2, 3, 4, 5, 6, 7, 8, 9, or 10 doses of an IDPN composition. In another embodiment, a dialysis machine accepts a dose in the form of a bag. In another embodiment, a dialysis machine accepts bags of a certain size. In another embodiment, a dialysis machine accepts bags of various sizes. In another embodiment, the sizes of the bags are as described herein.

In one embodiment, the invention provides methods for the treatment of malnutrition in a subject in need or want thereof, using the systems, devices, and IDPN compositions described herein.

In one embodiment, the invention provides a method for treating malnutrition in a subject in need or want thereof, the method comprising: a) formulating an aqueous composition comprising carbohydrates, amino acids, and optionally one or more of lipids and micronutrients, wherein the amount of each of the carbohydrates, the amino acids, the lipids, and the micronutrients is related to the body mass of the subject and optionally to the age of the subject; and b) infusing the composition into the subject at an infusion rate, wherein the infusion rate is related to the body mass of the subject and optionally to the age of the subject.

In one embodiment, the invention provides a method for treating malnutrition in a subject in need or want thereof, the method comprising: a) formulating an aqueous composition comprising carbohydrates, amino acids, and optionally one or more of lipids and micronutrients, wherein the amount of each of the carbohydrates, the amino acids, the lipids, and the micronutrients is related to the body mass of the subject and optionally to the age of the subject; and b) infusing the composition into the subject at an infusion rate, wherein the infusion rate is related to the body mass of the subject and optionally to the age of the subject. In another embodiment, the body mass is from 9 to 39 kg. In another embodiment, the body mass is from 34 to greater than 70 kg.

In one embodiment, the invention provides a method for treating malnutrition in a subject in need or want thereof, the method comprising: a) formulating an aqueous composition comprising carbohydrates and amino acids, wherein the amount of each of the carbohydrates and the amino acids is related to the body mass of the subject and optionally to the age of the subject; and b) infusing the composition into the subject at an infusion rate, wherein the infusion rate is related to the body mass of the subject and optionally to the age of the subject. In another embodiment, the body mass is from 9 to 39 kg. In another embodiment, the body mass is from 34 to greater than 70 kg.

In one embodiment, the invention provides a method for treating malnutrition in a subject in need or want thereof, the method comprising: a) formulating an aqueous composition comprising carbohydrates, amino acids, and micronutrients, wherein the amount of each of the carbohydrates, the amino acids, and the micronutrients is related to the body mass of the subject and optionally to the age of the subject; and b) infusing the composition into the subject at an infusion rate, wherein the infusion rate is related to the body mass of the subject and optionally to the age of the subject. In another embodiment, the body mass is from 9 to 39 kg. In another embodiment, the body mass is from 34 to greater than 70 kg.

In one embodiment, the invention provides a method for treating malnutrition in a subject in need or want thereof, the method comprising: a) formulating an aqueous composition comprising carbohydrates, amino acids, and lipids, wherein the amount of each of the carbohydrates, the amino acids, and lipids is related to the body mass of the subject and optionally to the age of the subject; and b) infusing the composition into the subject at an infusion rate, wherein the infusion rate is related to the body mass of the subject and optionally to the age of the subject. In another embodiment, the body mass is from 9 to 39 kg. In another embodiment, the body mass is from 34 to greater than 70 kg.

In one embodiment, the invention provides a method for treating malnutrition in a subject in need or want thereof, the method comprising: a) formulating an aqueous composition comprising carbohydrates, amino acids, lipids and micronutrients, wherein the amount of each of the carbohydrates, the amino acids, the lipids, and the micronutrients is related to the body mass of the subject and optionally to the age of the subject; and b) infusing the composition into the subject at an infusion rate, wherein the infusion rate is related to the body mass of the subject and optionally to the age of the subject. In another embodiment, the body mass is from 9 to 39 kg. In another embodiment, the body mass is from 34 to greater than 70 kg.

In one embodiment, the invention provides a method for treating malnutrition in a subject in need or want thereof, the method comprising: a) formulating an aqueous composition comprising carbohydrates, amino acids, and optionally one or more of lipids and micronutrients, wherein the amount of each of the carbohydrates, the amino acids, the lipids, and the micronutrients is related to the body mass of the subject; and b) infusing the composition into the subject at an infusion rate, wherein the infusion rate is related to the body mass of the subject. In another embodiment, the body mass is from 9 to 39 kg. In another embodiment, the body mass is from 34 to greater than 70 kg.

In one embodiment, the invention provides a method for treating malnutrition in a subject in need or want thereof, the method comprising: a) formulating an aqueous composition comprising carbohydrates and amino acids, wherein the amount of each of the carbohydrates and the amino acids is related to the body mass of the subject; and b) infusing the composition into the subject at an infusion rate, wherein the infusion rate is related to the body mass of the subject. In another embodiment, the body mass is from 9 to 39 kg. In another embodiment, the body mass is from 34 to greater than 70 kg.

In one embodiment, the invention provides a method for treating malnutrition in a subject in need or want thereof, the method comprising: a) formulating an aqueous composition comprising carbohydrates, amino acids, and micronutrients, wherein the amount of each of the carbohydrates, the amino acids, and the micronutrients is related to the body mass of the subject; and b) infusing the composition into the subject at an infusion rate, wherein the infusion rate is related to the body mass of the subject. In another embodiment, the body mass is from 9 to 39 kg. In another embodiment, the body mass is from 34 to greater than 70 kg.

In one embodiment, the invention provides a method for treating malnutrition in a subject in need or want thereof, the method comprising: a) formulating an aqueous composition comprising carbohydrates, amino acids, and lipids, wherein the amount of each of the carbohydrates, the amino acids, and lipids is related to the body mass of the subject; and b) infusing the composition into the subject at an infusion rate, wherein the infusion rate is related to the body mass of the subject.

In one embodiment, the invention provides a method for treating malnutrition in a subject in need or want thereof, the method comprising: a) formulating an aqueous composition comprising carbohydrates, amino acids, lipids and micronutrients, wherein the amount of each of the carbohydrates, the amino acids, the lipids, and the micronutrients is related to the body mass of the subject; and b) infusing the composition into the subject at an infusion rate, wherein the infusion rate is related to the body mass of the subject. In another embodiment, the body mass is from 9 to 39 kg. In another embodiment, the body mass is from 34 to greater than 70 kg.

In one embodiment, the invention provides a method for treating malnutrition in a subject in need or want thereof, the method comprising: a) formulating an aqueous composition comprising carbohydrates, amino acids, and optionally one or more of lipids and micronutrients, wherein the amount of each of the carbohydrates, the amino acids, the lipids, and the micronutrients is related to the estimated dry weight of the subject and optionally to the age of the subject; and b) infusing the composition into the subject at an infusion rate, wherein the infusion rate is related to the estimated dry weight of the subject and optionally to the age of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates and amino acids, wherein the amount of each of the carbohydrates and the amino acids is related to the estimated dry weight of the subject and optionally to the age of the subject; and b) infusing the composition into the subject at an infusion rate, wherein the infusion rate is related to the estimated dry weight of the subject and optionally to the age of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates, amino acids, and micronutrients, wherein the amount of each of the carbohydrates, the amino acids, and the micronutrients is related to the estimated dry weight of the subject and optionally to the age of the subject; and b) infusing the composition into the subject at an infusion rate, wherein the infusion rate is related to the estimated dry weight of the subject and optionally to the age of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates, amino acids, and lipids, wherein the amount of each of the carbohydrates, the amino acids, and lipids is related to the estimated dry weight of the subject and optionally to the age of the subject; and b) infusing the composition into the subject at an infusion rate, wherein the infusion rate is related to the estimated dry weight of the subject and optionally to the age of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates, amino acids, lipids and micronutrients, wherein the amount of each of the carbohydrates, the amino acids, the lipids, and the micronutrients is related to the estimated dry weight of the subject and optionally to the age of the subject; and b) infusing the composition into the subject at an infusion rate, wherein the infusion rate is related to the estimated dry weight of the subject and optionally to the age of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates, amino acids, and optionally one or more of lipids and micronutrients, wherein the amount of each of the carbohydrates, the amino acids, the lipids, and the micronutrients is related to the estimated dry weight of the subject; and b) infusing the composition into the subject at an infusion rate, wherein the infusion rate is related to the estimated dry weight of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates and amino acids, wherein the amount of each of the carbohydrates and the amino acids is related to the estimated dry weight of the subject; and b) infusing the composition into the subject at an infusion rate, wherein the infusion rate is related to the estimated dry weight of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates, amino acids, and micronutrients, wherein the amount of each of the carbohydrates, the amino acids, and the micronutrients is related to the estimated dry weight of the subject; and b) infusing the composition into the subject at an infusion rate, wherein the infusion rate is related to the estimated dry weight of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates, amino acids, and lipids, wherein the amount of each of the carbohydrates, the amino acids, and lipids is related to the estimated dry weight of the subject; and b) infusing the composition into the subject at an infusion rate, wherein the infusion rate is related to the estimated dry weight of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates, amino acids, lipids and micronutrients, wherein the amount of each of the carbohydrates, the amino acids, the lipids, and the micronutrients is related to the estimated dry weight of the subject; and b) infusing the composition into the subject at an infusion rate, wherein the infusion rate is related to the estimated dry weight of the subject. In another embodiment, the estimated dry weight is from 9 to 39 kg. In another embodiment, the estimated dry weight is from 34 to greater than 70 kg.

In one embodiment, the invention provides a method for treating malnutrition in a subject in need or want thereof, the method comprising: a) formulating an aqueous composition comprising carbohydrates, amino acids, and optionally one or more of lipids and micronutrients, wherein the amount of each of the carbohydrates, the amino acids, the lipids, and the micronutrients is related to the ideal body weight of the subject and optionally to the age of the subject; and b) infusing the composition into the subject at an infusion rate, wherein the infusion rate is related to the ideal body weight of the subject and optionally to the age of the subject. In another embodiment, the ideal body weight is from 9 to 39 kg. In another embodiment, the ideal body weight is from 34 to greater than 70 kg.

In one embodiment, the invention provides a method for treating malnutrition in a subject in need or want thereof, the method comprising: a) formulating an aqueous composition comprising carbohydrates and amino acids, wherein the amount of each of the carbohydrates and the amino acids is related to the ideal body weight of the subject and optionally to the age of the subject; and b) infusing the composition into the subject at an infusion rate, wherein the infusion rate is related to the ideal body weight of the subject and optionally to the age of the subject. In another embodiment, the ideal body weight is from 9 to 39 kg. In another embodiment, the ideal body weight is from 34 to greater than 70 kg.

In one embodiment, the invention provides a method for treating malnutrition in a subject in need or want thereof, the method comprising: a) formulating an aqueous composition comprising carbohydrates, amino acids, and micronutrients, wherein the amount of each of the carbohydrates, the amino acids, and the micronutrients is related to the ideal body weight of the subject and optionally to the age of the subject; and b) infusing the composition into the subject at an infusion rate, wherein the infusion rate is related to the ideal body weight of the subject and optionally to the age of the subject. In another embodiment, the ideal body weight is from 9 to 39 kg. In another embodiment, the ideal body weight is from 34 to greater than 70 kg.

In one embodiment, the invention provides a method for treating malnutrition in a subject in need or want thereof, the method comprising: a) formulating an aqueous composition comprising carbohydrates, amino acids, and lipids, wherein the amount of each of the carbohydrates, the amino acids, and lipids is related to the ideal body weight of the subject and optionally to the age of the subject; and b) infusing the composition into the subject at an infusion rate, wherein the infusion rate is related to the ideal body weight of the subject and optionally to the age of the subject. In another embodiment, the ideal body weight is from 9 to 39 kg. In another embodiment, the ideal body weight is from 34 to greater than 70 kg.

In one embodiment, the invention provides a method for treating malnutrition in a subject in need or want thereof, the method comprising: a) formulating an aqueous composition comprising carbohydrates, amino acids, lipids and micronutrients, wherein the amount of each of the carbohydrates, the amino acids, the lipids, and the micronutrients is related to the ideal body weight of the subject and optionally to the age of the subject; and b) infusing the composition into the subject at an infusion rate, wherein the infusion rate is related to the ideal body weight of the subject and optionally to the age of the subject. In another embodiment, the ideal body weight is from 9 to 39 kg. In another embodiment, the ideal body weight is from 34 to greater than 70 kg.

In one embodiment, the invention provides a method for treating malnutrition in a subject in need or want thereof, the method comprising: a) formulating an aqueous composition comprising carbohydrates, amino acids, and optionally one or more of lipids and micronutrients, wherein the amount of each of the carbohydrates, the amino acids, the lipids, and the micronutrients is related to the ideal body weight of the subject; and b) infusing the composition into the subject at an infusion rate, wherein the infusion rate is related to the ideal body weight of the subject. In another embodiment, the ideal body weight is from 9 to 39 kg. In another embodiment, the ideal body weight is from 34 to greater than 70 kg.

In one embodiment, the invention provides a method for treating malnutrition in a subject in need or want thereof, the method comprising: a) formulating an aqueous composition comprising carbohydrates and amino acids, wherein the amount of each of the carbohydrates and the amino acids is related to the ideal body weight of the subject; and b) infusing the composition into the subject at an infusion rate, wherein the infusion rate is related to the ideal body weight of the subject. In another embodiment, the ideal body weight is from 9 to 39 kg. In another embodiment, the ideal body weight is from 34 to greater than 70 kg.

In one embodiment, the invention provides a method for treating malnutrition in a subject in need or want thereof, the method comprising: a) formulating an aqueous composition comprising carbohydrates, amino acids, and micronutrients, wherein the amount of each of the carbohydrates, the amino acids, and the micronutrients is related to the ideal body weight of the subject; and b) infusing the composition into the subject at an infusion rate, wherein the infusion rate is related to the ideal body weight of the subject. In another embodiment, the ideal body weight is from 9 to 39 kg. In another embodiment, the ideal body weight is from 34 to greater than 70 kg.

In one embodiment, the invention provides a method for treating malnutrition in a subject in need or want thereof, the method comprising: a) formulating an aqueous composition comprising carbohydrates, amino acids, and lipids, wherein the amount of each of the carbohydrates, the amino acids, and lipids is related to the ideal body weight of the subject; and b) infusing the composition into the subject at an infusion rate, wherein the infusion rate is related to the ideal body weight of the subject. In another embodiment, the ideal body weight is from 9 to 39 kg. In another embodiment, the ideal body weight is from 34 to greater than 70 kg.

In one embodiment, the invention provides a method for treating malnutrition in a subject in need or want thereof, the method comprising: a) formulating an aqueous composition comprising carbohydrates, amino acids, lipids and micronutrients, wherein the amount of each of the carbohydrates, the amino acids, the lipids, and the micronutrients is related to the ideal body weight of the subject; and b) infusing the composition into the subject at an infusion rate, wherein the infusion rate is related to the ideal body weight of the subject. In another embodiment, the ideal body weight is from 9 to 39 kg. In another embodiment, the ideal body weight is from 34 to greater than 70 kg.

In one embodiment, the invention provides a method of treating malnutrition in a hemodialysis subject in need thereof comprising determining a body mass of the subject, wherein if the body mass of the subject is between 9 and 12 kg, the subject is parenterally administered about 4 g of dextrose and about 13.5 g of amino acids in about 124 mL of an aqueous composition; wherein if the body mass of the subject is between 13 and 17 kg, the subject is parenterally administered about 6 g of dextrose and about 19.5 g of amino acids in about 156 mL of an aqueous composition; wherein if the body mass of the subject is between 18 and 22 kg, the subject is parenterally administered about 9 g of dextrose and about 27 g of amino acids in about 198 mL of an aqueous composition; wherein if the body mass of the subject is between 23 and 27 kg, the subject is parenterally administered about 11 g of dextrose and about 34.5 g of amino acids in about 239 mL of an aqueous composition; wherein if the body mass of the subject is between 28 and 33 kg, the subject is parenterally administered about 14 g of dextrose and about 42 g of amino acids in about 280 mL of an aqueous composition; and wherein if the body mass of the subject is between 34 and 39 kg, the subject is parenterally administered about 17 g of dextrose and about 51 g of amino acids in about 329 mL of an aqueous composition; thereby treating malnutrition in the hemodialysis subject in need thereof.

In another embodiment, the invention provides a method of treating malnutrition in a hemodialysis subject in need thereof comprising determining a body mass of the subject, wherein if the body mass of the subject is between 9 and 12 kg, the subject is parenterally administered about 5 g of dextrose and about 13.5 g of amino acids in about 125 mL of an aqueous composition; wherein if the body mass of the subject is between 13 and 17 kg, the subject is parenterally administered about 8 g of dextrose and about 19.5 g of amino acids in about 158 mL of an aqueous composition; wherein if the body mass of the subject is between 18 and 22 kg, the subject is parenterally administered about 10.5 g of dextrose and about 27 g of amino acids in about 200 mL of an aqueous composition; wherein if the body mass of the subject is between 23 and 27 kg, the subject is parenterally administered about 13 g of dextrose and about 34.5 g of amino acids in about 242 mL of an aqueous composition; wherein if the body mass of the subject is between 28 and 33 kg, the subject is parenterally administered about 16 g of dextrose and about 42 g of amino acids in about 283 mL of an aqueous composition; and wherein if the body mass of the subject is between 34 and 39 kg, the subject is parenterally administered about 20 g of dextrose and about 51 g of amino acids in about 334 mL of an aqueous composition; thereby treating malnutrition in the hemodialysis subject in need thereof.

In another embodiment, the invention provides a method of treating malnutrition in a hemodialysis subject in need thereof comprising determining a body mass of the subject, wherein if the body mass of the subject is between 9 and 12 kg, the subject is parenterally administered about 6 g of dextrose and about 13.5 g of amino acids in about 127 mL of an aqueous composition; wherein if the body mass of the subject is between 13 and 17 kg, the subject is parenterally administered about 9 g of dextrose and about 19.5 g of amino acids in about 160 mL of an aqueous composition; wherein if the body mass of the subject is between 18 and 22 kg, the subject is parenterally administered about 12 g of dextrose and about 27 g of amino acids in about 202 mL of an aqueous composition; wherein if the body mass of the subject is between 23 and 27 kg, the subject is parenterally administered about 15.5 g of dextrose and about 34.5 g of amino acids in about 245 mL of an aqueous composition; wherein if the body mass of the subject is between 28 and 33 kg, the subject is parenterally administered about 19 g of dextrose and about 42 g of amino acids in about 287 mL of an aqueous composition; and wherein if the body mass of the subject is between 34 and 39 kg, the subject is parenterally administered about 23 g of dextrose and about 51 g of amino acids in about 338 mL of an aqueous composition; thereby treating malnutrition in the hemodialysis subject in need thereof.

In another embodiment, the invention provides a method of treating malnutrition in a hemodialysis subject in need thereof comprising determining a body mass of the subject, wherein if the body mass of the subject is between 9 and 12 kg, the subject is parenterally administered about 4 g of dextrose and about 13.5 g of amino acids in about 146 mL of an aqueous composition; wherein if the body mass of the subject is between 13 and 17 kg, the subject is parenterally administered about 6 g of dextrose and about 19.5 g of amino acids in about 189 mL of an aqueous composition; wherein if the body mass of the subject is between 18 and 22 kg, the subject is parenterally administered about 9 g of dextrose and about 27 g of amino acids in about 243 mL of an aqueous composition; wherein if the body mass of the subject is between 23 and 27 kg, the subject is parenterally administered about 11 g of dextrose and about 34.5 g of amino acids in about 296 mL of an aqueous composition; wherein if the body mass of the subject is between 28 and 33 kg, the subject is parenterally administered about 14 g of dextrose and about 42 g of amino acids in about 350 mL of an aqueous composition; and wherein if the body mass of the subject is between 34 and 39 kg, the subject is parenterally administered about 17 g of dextrose and about 51 g of amino acids in about 414 mL of an aqueous composition; thereby treating malnutrition in the hemodialysis subject in need thereof.

In another embodiment, the invention provides a method of treating malnutrition in a hemodialysis subject in need thereof comprising determining a body mass of the subject, wherein if the body mass of the subject is between 9 and 12 kg, the subject is parenterally administered about 5 g of dextrose and about 13.5 g of amino acids in about 147 mL of an aqueous composition; wherein if the body mass of the subject is between 13 and 17 kg, the subject is parenterally administered about 8 g of dextrose and about 19.5 g of amino acids in about 191 mL of an aqueous composition; wherein if the body mass of the subject is between 18 and 22 kg, the subject is parenterally administered about 10.5 g of dextrose and about 27 g of amino acids in about 243 mL of an aqueous composition; wherein if the body mass of the subject is between 23 and 27 kg, the subject is parenterally administered about 13 g of dextrose and about 34.5 g of amino acids in about 299 mL of an aqueous composition; wherein if the body mass of the subject is between 28 and 33 kg, the subject is parenterally administered about 16 g of dextrose and about 42 g of amino acids in about 353 mL of an aqueous composition; and wherein if the body mass of the subject is between 34 and 39 kg, the subject is parenterally administered about 20 g of dextrose and about 51 g of amino acids in about 419 mL of an aqueous composition; thereby treating malnutrition in the hemodialysis subject in need thereof.

In another embodiment, the invention provides a method of treating malnutrition in a hemodialysis subject in need thereof comprising determining a body mass of the subject, wherein if the body mass of the subject is between 9 and 12 kg, the subject is parenterally administered about 6 g of dextrose and about 13.5 g of amino acids in about 149 mL of an aqueous composition; wherein if the body mass of the subject is between 13 and 17 kg, the subject is parenterally administered about 9 g of dextrose and about 19.5 g of amino acids in about 193 mL of an aqueous composition; wherein if the body mass of the subject is between 18 and 22 kg, the subject is parenterally administered about 12 g of dextrose and about 27 g of amino acids in about 247 mL of an aqueous composition; wherein if the body mass of the subject is between 23 and 27 kg, the subject is parenterally administered about 15.5 g of dextrose and about 34.5 g of amino acids in about 302 mL of an aqueous composition; wherein if the body mass of the subject is between 28 and 33 kg, the subject is parenterally administered about 19 g of dextrose and about 42 g of amino acids in about 357 mL of an aqueous composition; and wherein if the body mass of the subject is between 34 and 39 kg, the subject is parenterally administered about 23 g of dextrose and about 51 g of amino acids in about 423 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 17 g of dextrose and about 51 g of amino acids in about 329 mL of an aqueous composition; wherein if the body mass of the subject is between 40 and 44 kg, the subject is parenterally administered about 20 g of dextrose and about 60 g of amino acids in about 379 mL of an aqueous composition; wherein if the body mass of the subject is between 45 and 51 kg, the subject is parenterally administered about 22 g of dextrose and about 68 g of amino acids in about 421 mL of an aqueous composition; wherein if the body mass of the subject is between 52 and 59 kg, the subject is parenterally administered about 26 g of dextrose and about 78 g of amino acids in about 477 mL of an aqueous composition; wherein if the body mass of the subject is between 60 and 69 kg, the subject is parenterally administered about 30 g of dextrose and about 90 g of amino acids in about 543 mL of an aqueous composition; and wherein if the body mass of the subject is 70 kg or higher, the subject is parenterally administered about 35 g of dextrose and about 105 g of amino acids in about 625 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 23 g of dextrose and about 51 g of amino acids in about 338 mL of an aqueous composition; wherein if the body mass of the subject is between 40 and 44 kg, the subject is parenterally administered about 27 g of dextrose and about 60 g of amino acids in about 389 mL of an aqueous composition; wherein if the body mass of the subject is between 45 and 51 kg, the subject is parenterally administered about 30 g of dextrose and about 68 g of amino acids in about 433 mL of an aqueous composition; wherein if the body mass of the subject is between 52 and 59 kg, the subject is parenterally administered about 35 g of dextrose and about 78 g of amino acids in about 490 mL of an aqueous composition; wherein if the body mass of the subject is between 60 and 69 kg, the subject is parenterally administered about 41 g of dextrose and about 90 g of amino acids in about 559 mL of an aqueous composition; and wherein if the body mass of the subject is 70 kg or higher, the subject is parenterally administered about 47 g of dextrose and about 105 g of amino acids in about 642 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 20 g of dextrose and about 51 g of amino acids in about 334 mL of an aqueous composition; wherein if the body mass of the subject is between 40 and 44 kg, the subject is parenterally administered about 23 g of dextrose and about 60 g of amino acids in about 383 mL of an aqueous composition; wherein if the body mass of the subject is between 45 and 51 kg, the subject is parenterally administered about 26 g of dextrose and about 68 g of amino acids in about 427 mL of an aqueous composition; wherein if the body mass of the subject is between 52 and 59 kg, the subject is parenterally administered about 30 g of dextrose and about 78 g of amino acids in about 483 mL of an aqueous composition; wherein if the body mass of the subject is between 60 and 69 kg, the subject is parenterally administered about 35 g of dextrose and about 90 g of amino acids in about 550 mL of an aqueous composition; and wherein if the body mass of the subject is 70 kg or higher, the subject is parenterally administered about 41 g of dextrose and about 105 g of amino acids in about 635 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 17 g of dextrose and about 51 g of amino acids in about 414 mL of an aqueous composition; wherein if the body mass of the subject is between 40 and 44 kg, the subject is parenterally administered about 20 g of dextrose and about 60 g of amino acids in about 479 mL of an aqueous composition; wherein if the body mass of the subject is between 45 and 51 kg, the subject is parenterally administered about 22 g of dextrose and about 68 g of amino acids in about 536 mL of an aqueous composition; wherein if the body mass of the subject is between 52 and 59 kg, the subject is parenterally administered about 26 g of dextrose and about 78 g of amino acids in about 607 mL of an aqueous composition; wherein if the body mass of the subject is between 60 and 69 kg, the subject is parenterally administered about 30 g of dextrose and about 90 g of amino acids in about 693 mL of an aqueous composition; and wherein if the body mass of the subject is 70 kg or higher, the subject is parenterally administered about 35 g of dextrose and about 105 g of amino acids in about 800 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 23 g of dextrose and about 51 g of amino acids in about 423 mL of an aqueous composition; wherein if the body mass of the subject is between 40 and 44 kg, the subject is parenterally administered about 27 g of dextrose and about 60 g of amino acids in about 489 mL of an aqueous composition; wherein if the body mass of the subject is between 45 and 51 kg, the subject is parenterally administered about 30 g of dextrose and about 68 g of amino acids in about 548 mL of an aqueous composition; wherein if the body mass of the subject is between 52 and 59 kg, the subject is parenterally administered about 35 g of dextrose and about 78 g of amino acids in about 620 mL of an aqueous composition; wherein if the body mass of the subject is between 60 and 69 kg, the subject is parenterally administered about 41 g of dextrose and about 90 g of amino acids in about 709 mL of an aqueous composition; and wherein if the body mass of the subject is 70 kg or higher, the subject is parenterally administered about 47 g of dextrose and about 105 g of amino acids in about 817 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 20 g of dextrose and about 51 g of amino acids in about 419 mL of an aqueous composition; wherein if the body mass of the subject is between 40 and 44 kg, the subject is parenterally administered about 23 g of dextrose and about 60 g of amino acids in about 483 mL of an aqueous composition; wherein if the body mass of the subject is between 45 and 51 kg, the subject is parenterally administered about 26 g of dextrose and about 68 g of amino acids in about 542 mL of an aqueous composition; wherein if the body mass of the subject is between 52 and 59 kg, the subject is parenterally administered about 30 g of dextrose and about 78 g of amino acids in about 613 mL of an aqueous composition; wherein if the body mass of the subject is between 60 and 69 kg, the subject is parenterally administered about 35 g of dextrose and about 90 g of amino acids in about 700 mL of an aqueous composition; and wherein if the body mass of the subject is 70 kg or higher, the subject is parenterally administered about 41 g of dextrose and about 105 g of amino acids in about 809 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 17 g of dextrose, about 51 g of amino acids and about 8.6 g of lipids in about 372 mL of an aqueous composition; wherein if the body mass of the subject is between 40 and 44 kg, the subject is parenterally administered about 20 g of dextrose, about 60 g of amino acids and about 10.2 g of lipids in about 430 mL of an aqueous composition; wherein if the body mass of the subject is between 45 and 51 kg, the subject is parenterally administered about 22 g of dextrose, about 68 g of amino acids and about 11.2 g of lipids in about 477 mL of an aqueous composition; wherein if the body mass of the subject is between 52 and 59 kg, the subject is parenterally administered about 26 g of dextrose, about 78 g of amino acids and about 13.2 g of lipids in about 543 mL of an aqueous composition; wherein if the body mass of the subject is between 60 and 69 kg, the subject is parenterally administered about 30 g of dextrose, about 90 g of amino acids and about 15.2 g of lipids in about 619 mL of an aqueous composition; and wherein if the body mass of the subject is 70 kg or higher, the subject is parenterally administered about 35 g of dextrose, about 105 g of amino acids and about 17.8 g of lipids in about 715 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 23 g of dextrose, about 51 g of amino acids and about 11.8 g of lipids in about 397 mL of an aqueous composition; wherein if the body mass of the subject is between 40 and 44 kg, the subject is parenterally administered about 27 g of dextrose, about 60 g of amino acids and about 13.8 g of lipids in about 458 mL of an aqueous composition; wherein if the body mass of the subject is between 45 and 51 kg, the subject is parenterally administered about 30 g of dextrose, about 68 g of amino acids and about 15.2 g of lipids in about 509 mL of an aqueous composition; wherein if the body mass of the subject is between 52 and 59 kg, the subject is parenterally administered about 35 g of dextrose, about 78 g of amino acids and about 17.8 g of lipids in about 579 mL of an aqueous composition; wherein if the body mass of the subject is between 60 and 69 kg, the subject is parenterally administered about 41 g of dextrose, about 90 g of amino acids and about 21 g of lipids in about 664 mL of an aqueous composition; and wherein if the body mass of the subject is 70 kg or higher, the subject is parenterally administered about 47 g of dextrose, about 105 g of amino acids and about 24 g of lipids in about 762 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 20 g of dextrose, about 51 g of amino acids and about 10.2 g of lipids in about 385 mL of an aqueous composition; wherein if the body mass of the subject is between 40 and 44 kg, the subject is parenterally administered about 23 g of dextrose, about 60 g of amino acids and about 11.8 g of lipids in about 442 mL of an aqueous composition; wherein if the body mass of the subject is between 45 and 51 kg, the subject is parenterally administered about 26 g of dextrose, about 68 g of amino acids and about 13.3 g of lipids in about 493 mL of an aqueous composition; wherein if the body mass of the subject is between 52 and 59 kg, the subject is parenterally administered about 30 g of dextrose, about 78 g of amino acids and about 15.2 g of lipids in about 559 mL of an aqueous composition; wherein if the body mass of the subject is between 60 and 69 kg, the subject is parenterally administered about 35 g of dextrose, about 90 g of amino acids and about 17.8 g of lipids in about 639 mL of an aqueous composition; and wherein if the body mass of the subject is 70 kg or higher, the subject is parenterally administered about 41 g of dextrose, about 105 g of amino acids and about 21 g of lipids in about 739 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 17 g of dextrose, about 51 g of amino acids and about 8.6 g of lipids in about 457 mL of an aqueous composition; wherein if the body mass of the subject is between 40 and 44 kg, the subject is parenterally administered about 20 g of dextrose, about 60 g of amino acids and about 10.2 g of lipids in about 530 mL of an aqueous composition; wherein if the body mass of the subject is between 45 and 51 kg, the subject is parenterally administered about 22 g of dextrose, about 68 g of amino acids and about 11.2 g of lipids in about 590 mL of an aqueous composition; wherein if the body mass of the subject is between 52 and 59 kg, the subject is parenterally administered about 26 g of dextrose, about 78 g of amino acids and about 13.2 g of lipids in about 673 mL of an aqueous composition; wherein if the body mass of the subject is between 60 and 69 kg, the subject is parenterally administered about 30 g of dextrose, about 78 g of amino acids and about 15.2 g of lipids in about 769 mL of an aqueous composition; and wherein if the body mass of the subject is 70 kg or higher, the subject is parenterally administered about 35 g of dextrose, about 105 g of amino acids and about 17.8 g of lipids in about 889 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 23 g of dextrose, about 51 g of amino acids and about 11.8 g of lipids in about 482 mL of an aqueous composition; wherein if the body mass of the subject is between 40 and 44 kg, the subject is parenterally administered about 27 g of dextrose, about 60 g of amino acids and about 13.8 g of lipids in about 558 mL of an aqueous composition; wherein if the body mass of the subject is between 45 and 51 kg, the subject is parenterally administered about 30 g of dextrose, about 68 g of amino acids and about 15.2 g of lipids in about 622 mL of an aqueous composition; wherein if the body mass of the subject is between 52 and 59 kg, the subject is parenterally administered about 35 g of dextrose, about 78 g of amino acids and about 17.8 g of lipids in about 709 mL of an aqueous composition; wherein if the body mass of the subject is between 60 and 69 kg, the subject is parenterally administered about 41 g of dextrose, about 90 g of amino acids and about 21 g of lipids in about 814 mL of an aqueous composition; and wherein if the body mass of the subject is 70 kg or higher, the subject is parenterally administered about 47 g of dextrose, about 105 g of amino acids and about 24 g of lipids in about 937 mL of an aqueous composition; thereby treating malnutrition in the hemodialysis subject in need thereof.

In another embodiment, the invention provides a method useful for treating malnutrition in a hemodialysis subject in need thereof comprising determining a body mass of the subject, wherein if the body mass of the subject is between 34 and 39 kg, the subject is parenterally administered about 20 g of dextrose, about 51 g of amino acids and about 10.2 g of lipids in about 470 mL of an aqueous composition; wherein if the body mass of the subject is between 40 and 44 kg, the subject is parenterally administered about 23 g of dextrose, about 60 g of amino acids and about 11.8 g of lipids in about 542 mL of an aqueous composition; wherein if the body mass of the subject is between 45 and 51 kg, the subject is parenterally administered about 26 g of dextrose, about 68 g of amino acids and about 13.2 g of lipids in about 606 mL of an aqueous composition; wherein if the body mass of the subject is between 52 and 59 kg, the subject is parenterally administered about 30 g of dextrose, about 78 g of amino acids and about 15.2 g of lipids in about 689 mL of an aqueous composition; wherein if the body mass of the subject is between 60 and 69 kg, the subject is parenterally administered about 35 g of dextrose, about 90 g of amino acids and about 17.8 g of lipids in about 789 mL of an aqueous composition; and wherein if the body mass of the subject is 70 kg or higher, the subject is parenterally administered about 41 g of dextrose, about 105 g of amino acids and about 21 g of lipids in about 914 mL of an aqueous composition; thereby treating malnutrition in the hemodialysis subject in need thereof.

In one embodiment, a subject has adequate caloric intake. In another embodiment, a subject has inadequate caloric intake. In another embodiment, a subject has inadequate protein intake. In another embodiment, a subject has adequate caloric intake and inadequate protein intake. In another embodiment, a subject has inadequate caloric intake and inadequate protein intake. In another embodiment, a subject has normal body weight. In another embodiment, a subject is overweight. In another embodiment, a subject is obese. In another embodiment, a subject is underweight. In another embodiment, a subject's ability to process fluids is impaired. In another embodiment, a subject benefits from reduced IDPN composition volume. In another embodiment, a subject is administered an IDPN composition with reduced volume.

In one embodiment, the IDPN solution is formulated based on the subject's body mass. In another embodiment, the subject's body mass is estimated dry weight. Estimated dry weight describes the mass of a subject prior to administration of an IDPN solution. In another embodiment, the subject's body mass is the subjects ideal body mass. Ideal body mass is determined based on the subject's height. If a subject's actual body mass is greater than or equal to 115% of the subject's ideal body mass, then an IDPN solution can be formulated based on the subject's ideal body mass. In the case of an obese subject, an IDPN solution formulated based on the obese subject's estimated dry weight or ideal body mass would lead to the formulation of an IDPN solution with a volume and nutrition content that are prohibitively high. The use of the ideal body mass, based on height, provides a safer mechanism for determining the amount of nutrition that the obese subject should receive.

In some embodiments, the invention provides a sterile aqueous composition for parenteral administration comprising: between 0.01 and 0.10 g/ml of dextrose; and between 0.07 and 0.20 g/ml of amino acids.

In some embodiments, the invention provides a sterile aqueous composition for parenteral administration to a subject, the composition comprising an amount of dextrose and an amount of amino acids in a total volume, wherein: a) the amount of dextrose is about 20 g, the amount of amino acids is about 51 g, and the total volume is about 334 mL when the subject has a body mass of 34-39 kg; b) the amount of dextrose is about 23 g, the amount of amino acids is about 60 g, and the total volume is about 383 mL when the subject has a body mass of 40-44 kg; c) the amount of dextrose is about 26 g, the amount of amino acids is about 68 g, and the total volume is about 427 mL when the subject has a body mass of 45-51 kg; d) the amount of dextrose is about 30 g, the amount of amino acids is about 78 g, and the total volume is about 483 mL when the subject has a body mass of 52-59 kg; e) the amount of dextrose is about 35 g, the amount of amino acids is about 90 g, and the total volume is about 550 mL when the subject has a body mass of 60-69 kg; and f) the amount of dextrose is about 41 g, the amount of amino acids is about 105 g, and the total volume is about 635 mL when the subject has a body mass of at least 70 kg.

In some embodiments, the invention provides a sterile aqueous composition for parenteral administration to a subject, the composition comprising an amount of dextrose and an amount of amino acids in a total volume, wherein: a) the amount of dextrose is about 20 g, the amount of amino acids is about 51 g, and the total volume is about 419 mL when the subject has a body mass of 34-39 kg; b) the amount of dextrose is about 23 g, the amount of amino acids is about 60 g, and the total volume is about 483 mL when the subject has a body mass of 40-44 kg; c) the amount of dextrose is about 26 g, the amount of amino acids is about 68 g, and the total volume is about 540 mL when the subject has a body mass of 45-51 kg; d) the amount of dextrose is about 30 g, the amount of amino acids is about 78 g, and the total volume is about 613 mL when the subject has a body mass of 52-59 kg; e) the amount of dextrose is about 35 g, the amount of amino acids is about 90 g, and the total volume is about 700 mL when the subject has a body mass of 60-69 kg; and f) the amount of dextrose is about 41 g, the amount of amino acids is about 105 g, and the total volume is about 809 mL when the subject has a body mass of at least 70 kg.

In some embodiments, the invention provides a sterile aqueous composition for parenteral administration to a subject, the composition comprising an amount of dextrose and an amount of amino acids in a total volume, wherein: a) the amount of dextrose is about 4 g, the amount of amino acids is about 13.5 g, and the total volume is about 124 mL when the subject has a body mass of 9-12 kg; b) the amount of dextrose is about 6 g, the amount of amino acids is about 19.5 g, and the total volume is about 156 mL when the subject has a body mass of 13-17 kg; c) the amount of dextrose is about 9 g, the amount of amino acids is about 27 g, and the total volume is about 198 mL when the subject has a body mass of 18-22 kg; d) the amount of dextrose is about 11 g, the amount of amino acids is about 34.5 g, and the total volume is about 239 mL when the subject has a body mass of 23-27 kg; e) the amount of dextrose is about 14 g, the amount of amino acids is about 42 g, and the total volume is about 280 mL when the subject has a body mass of 28-33 kg; and f) the amount of dextrose is about 17 g, the amount of amino acids is about 51 g, and the total volume is about 329 mL when the subject has a body mass of 34-39 kg.

In some embodiments, the invention provides a sterile aqueous composition for parenteral administration to a subject, the composition comprising an amount of dextrose and an amount of amino acids in a total volume, wherein: a) the amount of dextrose is about 5 g, the amount of amino acids is about 13.5 g, and the total volume is about 125 mL when the subject has a body mass of 9-12 kg; b) the amount of dextrose is about 8 g, the amount of amino acids is about 19.5 g, and the total volume is about 158 mL when the subject has a body mass of 13-17 kg; c) the amount of dextrose is about 10.5 g, the amount of amino acids is about 27 g, and the total volume is about 200 mL when the subject has a body mass of 18-22 kg; d) the amount of dextrose is about 13 g, the amount of amino acids is about 34.5 g, and the total volume is about 242 mL when the subject has a body mass of 23-27 kg; e) the amount of dextrose is about 16 g, the amount of amino acids is about 42 g, and the total volume is about 283 mL when the subject has a body mass of 28-33 kg; and f) the amount of dextrose is about 20 g, the amount of amino acids is about 51 g, and the total volume is about 334 mL when the subject has a body mass of 34-39 kg.

In some embodiments, the invention provides a sterile aqueous composition for parenteral administration to a subject, the composition comprising an amount of dextrose and an amount of amino acids in a total volume, wherein: a) the amount of dextrose is about 6 g, the amount of amino acids is about 13.5 g, and the total volume is about 127 mL when the subject has a body mass of 9-12 kg; b) the amount of dextrose is about 9 g, the amount of amino acids is about 19.5 g, and the total volume is about 160 mL when the subject has a body mass of 13-17 kg; c) the amount of dextrose is about 12 g, the amount of amino acids is about 27 g, and the total volume is about 202 mL when the subject has a body mass of 18-22 kg; d) the amount of dextrose is about 15.5 g, the amount of amino acids is about 34.5 g, and the total volume is about 245 mL when the subject has a body mass of 23-27 kg; e) the amount of dextrose is about 19 g, the amount of amino acids is about 42 g, and the total volume is about 287 mL when the subject has a body mass of 28-33 kg; and f) the amount of dextrose is about 23 g, the amount of amino acids is about 51 g, and the total volume is about 338 mL when the subject has a body mass of 34-39 kg.

In some embodiments, the invention provides a sterile aqueous composition for parenteral administration to a subject, the composition comprising an amount of dextrose and an amount of amino acids in a total volume, wherein: a) the amount of dextrose is about 4 g, the amount of amino acids is about 13.5 g, and the total volume is about 146 mL when the subject has a body mass of 9-12 kg; b) the amount of dextrose is about 6 g, the amount of amino acids is about 19.5 g, and the total volume is about 189 mL when the subject has a body mass of 13-17 kg; c) the amount of dextrose is about 9 g, the amount of amino acids is about 27 g, and the total volume is about 243 mL when the subject has a body mass of 18-22 kg; d) the amount of dextrose is about 11 g, the amount of amino acids is about 34.5 g, and the total volume is about 296 mL when the subject has a body mass of 23-27 kg; e) the amount of dextrose is about 14 g, the amount of amino acids is about 42 g, and the total volume is about 350 mL when the subject has a body mass of 28-33 kg; and f) the amount of dextrose is about 17 g, the amount of amino acids is about 51 g, and the total volume is about 414 mL when the subject has a body mass of 34-39 kg.

In some embodiments, the invention provides a sterile aqueous composition for parenteral administration to a subject, the composition comprising an amount of dextrose and an amount of amino acids in a total volume, wherein: a) the amount of dextrose is about 5 g, the amount of amino acids is about 13.5 g, and the total volume is about 147 mL when the subject has a body mass of 9-12 kg; b) the amount of dextrose is about 8 g, the amount of amino acids is about 19.5 g, and the total volume is about 191 mL when the subject has a body mass of 13-17 kg; c) the amount of dextrose is about 10.5 g, the amount of amino acids is about 27 g, and the total volume is about 245 mL when the subject has a body mass of 18-22 kg; d) the amount of dextrose is about 13 g, the amount of amino acids is about 34.5 g, and the total volume is about 299 mL when the subject has a body mass of 23-27 kg; e) the amount of dextrose is about 16 g, the amount of amino acids is about 42 g, and the total volume is about 353 mL when the subject has a body mass of 28-33 kg; and f) the amount of dextrose is about 20 g, the amount of amino acids is about 51 g, and the total volume is about 419 mL when the subject has a body mass of 34-39 kg.

In some embodiments, the invention provides a sterile aqueous composition for parenteral administration to a subject, the composition comprising an amount of dextrose and an amount of amino acids in a total volume, wherein: a) the amount of dextrose is about 6 g, the amount of amino acids is about 13.5 g, and the total volume is about 149 mL when the subject has a body mass of 9-12 kg; b) the amount of dextrose is about 9 g, the amount of amino acids is about 19.5 g, and the total volume is about 193 mL when the subject has a body mass of 13-17 kg; c) the amount of dextrose is about 12 g, the amount of amino acids is about 27 g, and the total volume is about 247 mL when the subject has a body mass of 18-22 kg; d) the amount of dextrose is about 15.5 g, the amount of amino acids is about 34.5 g, and the total volume is about 302 mL when the subject has a body mass of 23-27 kg; e) the amount of dextrose is about 19 g, the amount of amino acids is about 42 g, and the total volume is about 357 mL when the subject has a body mass of 28-33 kg; and f) the amount of dextrose is about 23 g, the amount of amino acids is about 51 g, and the total volume is about 423 mL when the subject has a body mass of 34-39 kg.

In some embodiments, the invention provides a sterile aqueous composition for parenteral administration to a subject, the composition comprising an amount of dextrose and an amount of amino acids in a total volume, wherein: a) the amount of dextrose is about 17 g, the amount of amino acids is about 51 g, and the total volume is about 329 mL when the subject has a body mass of 34-39 kg; b) the amount of dextrose is about 20 g, the amount of amino acids is about 60 g, and the total volume is about 379 mL when the subject has a body mass of 40-44 kg; c) the amount of dextrose is about 22 g, the amount of amino acids is about 68 g, and the total volume is about 421 mL when the subject has a body mass of 45-51 kg; d) the amount of dextrose is about 26 g, the amount of amino acids is about 78 g, and the total volume is about 477 mL when the subject has a body mass of 52-59 kg; e) the amount of dextrose is about 30 g, the amount of amino acids is about 90 g, and the total volume is about 543 mL when the subject has a body mass of 60-69 kg; and f) the amount of dextrose is about 35 g, the amount of amino acids is about 105 g, and the total volume is about 625 mL when the subject has a body mass of at least 70 kg.

In some embodiments, the invention provides a sterile aqueous composition for parenteral administration to a subject, the composition comprising an amount of dextrose and an amount of amino acids in a total volume, wherein: a) the amount of dextrose is about 23 g, the amount of amino acids is about 51 g, and the total volume is about 338 mL when the subject has a body mass of 34-39 kg; b) the amount of dextrose is about 27 g, the amount of amino acids is about 60 g, and the total volume is about 389 mL when the subject has a body mass of 40-44 kg; c) the amount of dextrose is about 30 g, the amount of amino acids is about 68 g, and the total volume is about 433 mL when the subject has a body mass of 45-51 kg; d) the amount of dextrose is about 35 g, the amount of amino acids is about 78 g, and the total volume is about 490 mL when the subject has a body mass of 52-59 kg; e) the amount of dextrose is about 41 g, the amount of amino acids is about 90 g, and the total volume is about 559 mL when the subject has a body mass of 60-69 kg; and f) the amount of dextrose is about 47 g, the amount of amino acids is about 105 g, and the total volume is about 642 mL when the subject has a body mass of at least 70 kg.

In some embodiments, the invention provides a sterile aqueous composition for parenteral administration to a subject, the composition comprising an amount of dextrose and an amount of amino acids in a total volume, wherein: a) the amount of dextrose is about 17 g, the amount of amino acids is about 51 g, and the total volume is about 414 mL when the subject has a body mass of 34-39 kg; b) the amount of dextrose is about 20 g, the amount of amino acids is about 60 g, and the total volume is about 479 mL when the subject has a body mass of 40-44 kg; c) the amount of dextrose is about 22 g, the amount of amino acids is about 68 g, and the total volume is about 536 mL when the subject has a body mass of 45-51 kg; d) the amount of dextrose is about 26 g, the amount of amino acids is about 78 g, and the total volume is about 607 mL when the subject has a body mass of 52-59 kg; e) the amount of dextrose is about 30 g, the amount of amino acids is about 90 g, and the total volume is about 693 mL when the subject has a body mass of 60-69 kg; and f) the amount of dextrose is about 35 g, the amount of amino acids is about 105 g, and the total volume is about 800 mL when the subject has a body mass of at least 70 kg.

In some embodiments, the invention provides a sterile aqueous composition for parenteral administration to a subject, the composition comprising an amount of dextrose and an amount of amino acids in a total volume, wherein: a) the amount of dextrose is about 23 g, the amount of amino acids is about 51 g, and the total volume is about 423 mL when the subject has a body mass of 34-39 kg; b) the amount of dextrose is about 27 g, the amount of amino acids is about 60 g, and the total volume is about 489 mL when the subject has a body mass of 40-44 kg; c) the amount of dextrose is about 30 g, the amount of amino acids is about 68 g, and the total volume is about 548 mL when the subject has a body mass of 45-51 kg; d) the amount of dextrose is about 35 g, the amount of amino acids is about 78 g, and the total volume is about 620 mL when the subject has a body mass of 52-59 kg; e) the amount of dextrose is about 41 g, the amount of amino acids is about 90 g, and the total volume is about 709 mL when the subject has a body mass of 60-69 kg; and f) the amount of dextrose is about 47 g, the amount of amino acids is about 105 g, and the total volume is about 817 mL when the subject has a body mass of at least 70 kg.

In some embodiments, the invention provides a sterile aqueous composition for parenteral administration to a subject, the composition comprising an amount of dextrose, an amount of amino acids, and an amount of lipids in a total volume, wherein: a) the amount of dextrose is about 17 g, the amount of amino acids is about 51 g, the amount of lipids is about 8.6 g, and the total volume is about 372 mL when the subject has a body mass of 34-39 kg; b) the amount of dextrose is about 20 g, the amount of amino acids is about 60 g, the amount of lipids is about 10.2 g, and the total volume is about 430 mL when the subject has a body mass of 40-44 kg; c) the amount of dextrose is about 22 g, the amount of amino acids is about 68 g, the amount of lipids is about 11.2 g, and the total volume is about 477 mL when the subject has a body mass of 45-51 kg; d) the amount of dextrose is about 26 g, the amount of amino acids is about 78 g, the amount of lipids is about 13.2 g, and the total volume is about 543 mL when the subject has a body mass of 52-59 kg; e) the amount of dextrose is about 30 g, the amount of amino acids is about 90 g, the amount of lipids is about 15.2 g, and the total volume is about 619 mL when the subject has a body mass of 60-69 kg; and f) the amount of dextrose is about 35 g, the amount of amino acids is about 105 g, the amount of lipids is about 17.8 g, and the total volume is about 715 mL when the subject has a body mass of at least 70 kg.

In some embodiments, the invention provides a sterile aqueous composition for parenteral administration to a subject, the composition comprising an amount of dextrose, an amount of amino acids, and an amount of lipids in a total volume, wherein: a) the amount of dextrose is about 23 g, the amount of amino acids is about 51 g, the amount of lipids is about 11.8 g, and the total volume is about 397 mL when the subject has a body mass of 34-39 kg; b) the amount of dextrose is about 27 g, the amount of amino acids is about 60 g, the amount of lipids is about 13.8 g, and the total volume is about 458 mL when the subject has a body mass of 40-44 kg; c) the amount of dextrose is about 30 g, the amount of amino acids is about 68 g, the amount of lipids is about 15.2 g, and the total volume is about 509 mL when the subject has a body mass of 45-51 kg; d) the amount of dextrose is about 35 g, the amount of amino acids is about 78 g, the amount of lipids is about 17.8 g, and the total volume is about 579 mL when the subject has a body mass of 52-59 kg; e) the amount of dextrose is about 41 g, the amount of amino acids is about 90 g, the amount of lipids is about 21 g, and the total volume is about 664 mL when the subject has a body mass of 60-69 kg; and f) the amount of dextrose is about 47 g, the amount of amino acids is about 105 g, the amount of lipids is about 24 g, and the total volume is about 762 mL when the subject has a body mass of at least 70 kg.

In some embodiments, the invention provides a sterile aqueous composition for parenteral administration to a subject, the composition comprising an amount of dextrose, an amount of amino acids, and an amount of lipids in a total volume, wherein: a) the amount of dextrose is about 20 g, the amount of amino acids is about 51 g, the amount of lipids is about 10.2 g, and the total volume is about 385 mL when the subject has a body mass of 34-39 kg; b) the amount of dextrose is about 23 g, the amount of amino acids is about 60 g, the amount of lipids is about 11.8 g, and the total volume is about 442 mL when the subject has a body mass of 40-44 kg; c) the amount of dextrose is about 26 g, the amount of amino acids is about 68 g, the amount of lipids is about 13.3 g, and the total volume is about 493 mL when the subject has a body mass of 45-51 kg; d) the amount of dextrose is about 30 g, the amount of amino acids is about 78 g, the amount of lipids is about 15.2 g, and the total volume is about 559 mL when the subject has a body mass of 52-59 kg; e) the amount of dextrose is about 35 g, the amount of amino acids is about 90 g, the amount of lipids is about 17.8 g, and the total volume is about 639 mL when the subject has a body mass of 60-69 kg; and f) the amount of dextrose is about 41 g, the amount of amino acids is about 105 g, the amount of lipids is about 21 g, and the total volume is about 739 mL when the subject has a body mass of at least 70 kg.

In some embodiments, the invention provides a sterile aqueous composition for parenteral administration to a subject, the composition comprising an amount of dextrose, an amount of amino acids, and an amount of lipids in a total volume, wherein: a) the amount of dextrose is about 17 g, the amount of amino acids is about 51 g, the amount of lipids is about 8.6 g, and the total volume is about 457 mL when the subject has a body mass of 34-39 kg; b) the amount of dextrose is about 20 g, the amount of amino acids is about 60 g, the amount of lipids is about 10.2 g, and the total volume is about 530 mL when the subject has a body mass of 40-44 kg; c) the amount of dextrose is about 22 g, the amount of amino acids is about 68 g, the amount of lipids is about 11.2 g, and the total volume is about 590 mL when the subject has a body mass of 45-51 kg; d) the amount of dextrose is about 26 g, the amount of amino acids is about 78 g, the amount of lipids is about 13.2 g, and the total volume is about 673 mL when the subject has a body mass of 52-59 kg; e) the amount of dextrose is about 30 g, the amount of amino acids is about 90 g, the amount of lipids is about 15.2 g, and the total volume is about 769 mL when the subject has a body mass of 60-69 kg; and f) the amount of dextrose is about 35 g, the amount of amino acids is about 105 g, the amount of lipids is about 17.8 g, and the total volume is about 889 mL when the subject has a body mass of at least 70 kg.

In some embodiments, the invention provides a sterile aqueous composition for parenteral administration to a subject, the composition comprising an amount of dextrose, an amount of amino acids, and an amount of lipids in a total volume, wherein: a) the amount of dextrose is about 23 g, the amount of amino acids is about 51 g, the amount of lipids is about 11.8 g, and the total volume is about 482 mL when the subject has a body mass of 34-39 kg; b) the amount of dextrose is about 27 g, the amount of amino acids is about 60 g, the amount of lipids is about 13.8 g, and the total volume is about 558 mL when the subject has a body mass of 40-44 kg; c) the amount of dextrose is about 30 g, the amount of amino acids is about 68 g, the amount of lipids is about 15.2 g, and the total volume is about 622 mL when the subject has a body mass of 45-51 kg; d) the amount of dextrose is about 35 g, the amount of amino acids is about 78 g, the amount of lipids is about 17.8 g, and the total volume is about 709 mL when the subject has a body mass of 52-59 kg; e) the amount of dextrose is about 41 g, the amount of amino acids is about 90 g, the amount of lipids is about 21 g, and the total volume is about 814 mL when the subject has a body mass of 60-69 kg; and f) the amount of dextrose is about 47 g, the amount of amino acids is about 105 g, the amount of lipids is about 24 g, and the total volume is about 937 mL when the subject has a body mass of at least 70 kg.

In some embodiments, the invention provides a sterile aqueous composition for parenteral administration to a subject, the composition comprising an amount of dextrose, an amount of amino acids, and an amount of lipids in a total volume, wherein: a) the amount of dextrose is about 20 g, the amount of amino acids is about 51 g, the amount of lipids is about 10.2 g, and the total volume is about 470 mL when the subject has a body mass of 34-39 kg; b) the amount of dextrose is about 23 g, the amount of amino acids is about 60 g, the amount of lipids is about 11.8 g, and the total volume is about 542 mL when the subject has a body mass of 40-44 kg; c) the amount of dextrose is about 26 g, the amount of amino acids is about 68 g, the amount of lipids is about 13.2 g, and the total volume is about 606 mL when the subject has a body mass of 45-51 kg; d) the amount of dextrose is about 30 g, the amount of amino acids is about 78 g, the amount of lipids is about 15.2 g, and the total volume is about 689 mL when the subject has a body mass of 52-59 kg; e) the amount of dextrose is about 35 g, the amount of amino acids is about 90 g, the amount of lipids is about 17.8 g, and the total volume is about 789 mL when the subject has a body mass of 60-69 kg; and f) the amount of dextrose is about 41 g, the amount of amino acids is about 105 g, the amount of lipids is about 21 g, and the total volume is about 914 mL when the subject has a body mass of at least 70 kg.

In one embodiment, the invention provides a method of treating malnutrition in a pediatric subject, the method comprising parenterally administering a sterile aqueous composition to the subject, the composition comprising: an amount of dextrose from about 4 g to about 19 g and an amount of amino acids from about 13.5 g to about 42 g in a total volume of about 124 mL to about 357 mL, wherein the subject has a body mass of from 9 kg to 33 kg, wherein the administering is done at an infusion rate of from 17 mL/hour to 127 mL/hour.

In another embodiment, the amount of dextrose is 4 g, the amount of amino acids is 13.5 g, the total volume is 124 mL, and the infusion rate is 23 mL/hour or 45 mL/hour when the subject has a body mass of from 9 kg to 12 kg; the amount of dextrose is 6 g, the amount of amino acids is 19.5 g, the total volume is 156 mL, and the infusion rate is 28 mL/hour or 57 mL/hour when the subject has a body mass of from 13 kg to 17 kg; the amount of dextrose is 9 g, the amount of amino acids is 27 g, the total volume is 198 mL, and the infusion rate is 36 mL/hour or 72 mL/hour when the subject has a body mass of from 18 kg to 22 kg; the amount of dextrose is 11 g, the amount of amino acids is 34.5 g, the total volume is 239 mL, and the infusion rate is 43 mL/hour or 87 mL/hour when the subject has a body mass of from 23 kg to 27 kg; and the amount of dextrose is 14 g, the amount of amino acids is 42 g, the total volume is 280 mL, and the infusion rate is 51 mL/hour or 102 mL/hour when the subject has a body mass of from 28 kg to 33 kg.

In another embodiment, the amount of dextrose is 5 g, the amount of amino acids is 13.5 g, the total volume is 125 mL, and the infusion rate is 19 mL/hour or 39 mL/hour when the subject has a body mass of from 9 kg to 12 kg; the amount of dextrose is 8 g, the amount of amino acids is 19.5 g, the total volume is 158 mL, and the infusion rate is 24 mL/hour or 49 mL/hour when the subject has a body mass of from 13 kg to 17 kg; the amount of dextrose is 10.5 g, the amount of amino acids is 27 g, the total volume is 200 mL, and the infusion rate is 31 mL/hour or 62 mL/hour when the subject has a body mass of from 18 kg to 22 kg; the amount of dextrose is 13 g, the amount of amino acids is 34.5 g, the total volume is 242 mL, and the infusion rate is 37 mL/hour or 74 mL/hour when the subject has a body mass of from 23 kg to 27 kg; and the amount of dextrose is 16 g, the amount of amino acids is 42 g, the total volume is 283 mL, and the infusion rate is 44 mL/hour or 87 mL/hour when the subject has a body mass of from 28 kg to 33 kg.

In another embodiment, the amount of dextrose is 6 g, the amount of amino acids is 13.5 g, the total volume is 127 mL, and the infusion rate is 17 mL/hour or 34 mL/hour when the subject has a body mass of from 9 kg to 12 kg; the amount of dextrose is 9 g, the amount of amino acids is 19.5 g, the total volume is 160 mL, and the infusion rate is 21 mL/hour or 43 mL/hour when the subject has a body mass of from 13 kg to 17 kg; the amount of dextrose is 12 g, the amount of amino acids is 27 g, the total volume is 202 mL, and the infusion rate is 27 mL/hour or 54 mL/hour when the subject has a body mass of from 18 kg to 22 kg; the amount of dextrose is 15.5 g, the amount of amino acids is 34.5 g, the total volume is 245 mL, and the infusion rate is 33 mL/hour or 65 mL/hour when the subject has a body mass of from 23 kg to 27 kg; and the amount of dextrose is 19 g, the amount of amino acids is 42 g, the total volume is 287 mL, and the infusion rate is 38 mL/hour or 77 mL/hour when the subject has a body mass of from 28 kg to 33 kg.

In another embodiment, the amount of dextrose is 4 g, the amount of amino acids is 13.5 g, the total volume is 146 mL, and the infusion rate is 27 mL/hour or 53 mL/hour when the subject has a body mass of from 9 kg to 12 kg; the amount of dextrose is 6 g, the amount of amino acids is 19.5 g, the total volume is 189 mL, and the infusion rate is 34 mL/hour or 69 mL/hour when the subject has a body mass of from 13 kg to 17 kg; the amount of dextrose is 9 g, the amount of amino acids is 27 g, the total volume is 243 mL, and the infusion rate is 44 mL/hour or 88 mL/hour when the subject has a body mass of from 18 kg to 22 kg; the amount of dextrose is 11 g, the amount of amino acids is 34.5 g, the total volume is 296 mL, and the infusion rate is 54 mL/hour or 108 mL/hour when the subject has a body mass of from 23 kg to 27 kg; and the amount of dextrose is 14 g, the amount of amino acids is 42 g, the total volume is 350 mL, and the infusion rate is 64 mL/hour or 127 mL/hour when the subject has a body mass of from 28 kg to 33 kg.

In another embodiment, the amount of dextrose is 5 g, the amount of amino acids is 13.5 g, the total volume is 147 mL, and the infusion rate is 23 mL/hour or 45 mL/hour when the subject has a body mass of from 9 kg to 12 kg; the amount of dextrose is 8 g, the amount of amino acids is 19.5 g, the total volume is 191 mL, and the infusion rate is 29 mL/hour or 59 mL/hour when the subject has a body mass of from 13 kg to 17 kg; the amount of dextrose is 10.5 g, the amount of amino acids is 27 g, the total volume is 245 mL, and the infusion rate is 38 mL/hour or 75 mL/hour when the subject has a body mass of from 18 kg to 22 kg; the amount of dextrose is 13 g, the amount of amino acids is 34.5 g, the total volume is 299 mL, and the infusion rate is 46 mL/hour or 92 mL/hour when the subject has a body mass of from 23 kg to 27 kg; and the amount of dextrose is 16 g, the amount of amino acids is 42 g, the total volume is 353 mL, and the infusion rate is 54 mL/hour or 109 mL/hour when the subject has a body mass of from 28 kg to 33 kg.

In another embodiment, the amount of dextrose is 6 g, the amount of amino acids is 13.5 g, the total volume is 149 mL, and the infusion rate is 20 mL/hour or 40 mL/hour when the subject has a body mass of from 9 kg to 12 kg; the amount of dextrose is 9 g, the amount of amino acids is 19.5 g, the total volume is 193 mL, and the infusion rate is 26 mL/hour or 51 mL/hour when the subject has a body mass of from 13 kg to 17 kg; the amount of dextrose is 12 g, the amount of amino acids is 27 g, the total volume is 247 mL, and the infusion rate is 33 mL/hour or 66 mL/hour when the subject has a body mass of from 18 kg to 22 kg; the amount of dextrose is 15.5 g, the amount of amino acids is 34.5 g, the total volume is 302 mL, and the infusion rate is 40 mL/hour or 81 mL/hour when the subject has a body mass of from 23 kg to 27 kg; and the amount of dextrose is 19 g, the amount of amino acids is 42 g, the total volume is 357 mL, and the infusion rate is 48 mL/hour or 95 mL/hour when the subject has a body mass of from 28 kg to 33 kg.

In one embodiment, the invention provides a method of treating malnutrition in a subject, the method comprising parenterally administering a sterile aqueous composition to the subject, the composition comprising: an amount of dextrose from about 17 g to about 47 g and an amount of amino acids from about 51 g to about 105 g in a total volume of about 329 mL to about 817 mL, wherein the subject has a body mass of from 34 kg to at least 70 kg, wherein the administering is done at an infusion rate of from 45 mL/hour to 290 mL/hour.

In another embodiment, the amount of dextrose is 17 g, the amount of amino acids is 51 g, the total volume is 329 mL, and the infusion rate is 60 mL/hour or 120 mL/hour when the subject has a body mass of from 34 kg to 39 kg; the amount of dextrose is 20 g, the amount of amino acids is 60 g, the total volume is 379 mL, and the infusion rate is 70 mL/hour or 140 mL/hour when the subject has a body mass of from 40 kg to 44 kg; the amount of dextrose is 22 g, the amount of amino acids is 68 g, the total volume is 421 mL, and the infusion rate is 80 mL/hour or 155 mL/hour when the subject has a body mass of from 45 kg to 51 kg; the amount of dextrose is 26 g, the amount of amino acids is 78 g, the total volume is 477 mL, and the infusion rate is 90 mL/hour or 175 mL/hour when the subject has a body mass of from 52 kg to 59 kg; the amount of dextrose is 30 g, the amount of amino acids is 90 g, the total volume is 543 mL, and the infusion rate is 100 mL/hour or 200 mL/hour when the subject has a body mass of from 60 kg to 69 kg; and the amount of dextrose is 35 g, the amount of amino acids is 105 g, the total volume is 625 mL, and the infusion rate is 115 mL/hour or 230 mL/hour when the subject has a body mass of greater than 70 kg.

In another embodiment, the amount of dextrose is 23 g, the amount of amino acids is 51 g, the total volume is 338 mL, and the infusion rate is 45 mL/hour or 90 mL/hour when the subject has a body mass of from 34 kg to 39 kg; the amount of dextrose is 27 g, the amount of amino acids is 60 g, the total volume is 389 mL, and the infusion rate is 55 mL/hour or 105 mL/hour when the subject has a body mass of from 40 kg to 44 kg; the amount of dextrose is 30 g, the amount of amino acids is 68 g, the total volume is 433 mL, and the infusion rate is 60 mL/hour or 115 mL/hour when the subject has a body mass of from 45 kg to 51 kg; the amount of dextrose is 35 g, the amount of amino acids is 78 g, the total volume is 490 mL, and the infusion rate is 65 mL/hour or 130 mL/hour when the subject has a body mass of from 52 kg to 59 kg; the amount of dextrose is 41 g, the amount of amino acids is 90 g, the total volume is 559 mL, and the infusion rate is 75 mL/hour or 150 mL/hour when the subject has a body mass of from 60 kg to 69 kg; and the amount of dextrose is 47 g, the amount of amino acids is 105 g, the total volume is 642 mL, and the infusion rate is 85 mL/hour or 175 mL/hour when the subject has a body mass of greater than 70 kg.

In another embodiment, the amount of dextrose is 20 g, the amount of amino acids is 51 g, the total volume is 334 mL, and the infusion rate is 50 mL/hour or 105 mL/hour when the subject has a body mass of from 34 kg to 39 kg; the amount of dextrose is 23 g, the amount of amino acids is 60 g, the total volume is 383 mL, and the infusion rate is 60 mL/hour or 120 mL/hour when the subject has a body mass of from 40 kg to 44 kg; the amount of dextrose is 26 g, the amount of amino acids is 68 g, the total volume is 427 mL, and the infusion rate is 65 mL/hour or 135 mL/hour when the subject has a body mass of from 45 kg to 51 kg; the amount of dextrose is 30 g, the amount of amino acids is 78 g, the total volume is 483 mL, and the infusion rate is 75 mL/hour or 150 mL/hour when the subject has a body mass of from 52 kg to 59 kg; the amount of dextrose is 35 g, the amount of amino acids is 90 g, the total volume is 550 mL, and the infusion rate is 85 mL/hour or 170 mL/hour when the subject has a body mass of from 60 kg to 69 kg; and the amount of dextrose is 41 g, the amount of amino acids is 105 g, the total volume is 635 mL, and the infusion rate is 100 mL/hour or 195 mL/hour when the subject has a body mass of greater than 70 kg.

In another embodiment, the amount of dextrose is 17 g, the amount of amino acids is 51 g, the total volume is 414 mL, and the infusion rate is 75 mL/hour or 150 mL/hour when the subject has a body mass of from 34 kg to 39 kg; the amount of dextrose is 20 g, the amount of amino acids is 60 g, the total volume is 479 mL, and the infusion rate is 90 mL/hour or 175 mL/hour when the subject has a body mass of from 40 kg to 44 kg; the amount of dextrose is 22 g, the amount of amino acids is 68 g, the total volume is 536 mL, and the infusion rate is 100 mL/hour or 195 mL/hour when the subject has a body mass of from 45 kg to 51 kg; the amount of dextrose is 26 g, the amount of amino acids is 78 g, the total volume is 607 mL, and the infusion rate is 110 mL/hour or 220 mL/hour when the subject has a body mass of from 52 kg to 59 kg; the amount of dextrose is 30 g, the amount of amino acids is 90 g, the total volume is 693 mL, and the infusion rate is 130 mL/hour or 255 mL/hour when the subject has a body mass of from 60 kg to 69 kg; and the amount of dextrose is 35 g, the amount of amino acids is 105 g, the total volume is 800 mL, and the infusion rate is 145 mL/hour or 290 mL/hour when the subject has a body mass of greater than 70 kg.

In another embodiment the amount of dextrose is 23 g, the amount of amino acids is 51 g, the total volume is 423 mL, and the infusion rate is 60 mL/hour or 115 mL/hour when the subject has a body mass of from 34 kg to 39 kg; the amount of dextrose is 27 g, the amount of amino acids is 60 g, the total volume is 489 mL, and the infusion rate is 65 mL/hour or 130 mL/hour when the subject has a body mass of from 40 kg to 44 kg; the amount of dextrose is 30 g, the amount of amino acids is 68 g, the total volume is 548 mL, and the infusion rate is 75 mL/hour or 145 mL/hour when the subject has a body mass of from 45 kg to 51 kg; the amount of dextrose is 35 g, the amount of amino acids is 78 g, the total volume is 620 mL, and the infusion rate is 85 mL/hour or 165 mL/hour when the subject has a body mass of from 52 kg to 59 kg; the amount of dextrose is 41 g, the amount of amino acids is 90 g, the total volume is 709 mL, and the infusion rate is 95 mL/hour or 190 mL/hour when the subject has a body mass of from 60 kg to 69 kg; and the amount of dextrose is 47 g, the amount of amino acids is 105 g, the total volume is 817 mL, and the infusion rate is 110 mL/hour or 220 mL/hour when the subject has a body mass of greater than 70 kg.

In another embodiment, the amount of dextrose is 20 g, the amount of amino acids is 51 g, the total volume is 419 mL, and the infusion rate is 65 mL/hour or 130 mL/hour when the subject has a body mass of from 34 kg to 39 kg; the amount of dextrose is 23 g, the amount of amino acids is 60 g, the total volume is 483 mL, and the infusion rate is 75 mL/hour or 150 mL/hour when the subject has a body mass of from 40 kg to 44 kg; the amount of dextrose is 26 g, the amount of amino acids is 68 g, the total volume is 542 mL, and the infusion rate is 85 mL/hour or 170 mL/hour when the subject has a body mass of from 45 kg to 51 kg; the amount of dextrose is 30 g, the amount of amino acids is 78 g, the total volume is 613 mL, and the infusion rate is 95 mL/hour or 190 mL/hour when the subject has a body mass of from 52 kg to 59 kg; the amount of dextrose is 35 g, the amount of amino acids is 90 g, the total volume is 700 mL, and the infusion rate is 110 mL/hour or 215 mL/hour when the subject has a body mass of from 60 kg to 69 kg; and the amount of dextrose is 41 g, the amount of amino acids is 105 g, the total volume is 809 mL, and the infusion rate is 125 mL/hour or 250 mL/hour when the subject has a body mass of greater than 70 kg.

In one embodiment, the invention provides a method of treating malnutrition in a subject, the method comprising parenterally administering a sterile aqueous composition to the subject, the composition comprising: an amount of dextrose from about 17 g to about 47 g, an amount of amino acids from about 51 g to about 105 g, and an amount of lipids from 8.6 g about to about 24 in a total volume of about 372 mL to about 937 mL, wherein the subject has a body mass of at least 34 kg, wherein the administering is done at an infusion rate of from 45 mL/hour to 325 mL/hour.

In another embodiment, the amount of dextrose is 17 g, the amount of amino acids is 51 g, the amount of lipids is 8.6 g, the total volume is 372 mL, and the infusion rate is 60 mL/hour, 120 mL/hour, or 135 mL/hour when the subject has a body mass of from 34 kg to 39 kg; the amount of dextrose is 20 g, the amount of amino acids is 60 g, the amount of lipids is 10.2 g, the total volume is 430 mL, and the infusion rate is 70 mL/hour, 140 mL/hour, or 160 mL/hour when the subject has a body mass of from 40 kg to 44 kg; the amount of dextrose is 22 g, the amount of amino acids is 68 g, the amount of lipids is 11.2 g, the total volume is 477 mL, and the infusion rate is 80 mL/hour, 155 mL/hour, or 175 mL/hour when the subject has a body mass of from 45 kg to 51 kg; the amount of dextrose is 26 g, the amount of amino acids is 78 g, the amount of lipids is 13.2 g, the total volume is 543 mL, and the infusion rate is 90 mL/hour, 175 mL/hour, or 200 mL/hour when the subject has a body mass of from 52 kg to 59 kg; the amount of dextrose is 30 g, the amount of amino acids is 90 g, the amount of lipids is 15.2 g, the total volume is 619 mL, and the infusion rate is 100 mL/hour, 200 mL/hour, or 225 mL/hour when the subject has a body mass of from 60 kg to 69 kg; and the amount of dextrose is 35 g, the amount of amino acids is 105 g, the amount of lipids is 17.8 g, the total volume is 715 mL, and the infusion rate is 115 mL/hour, 230 mL/hour, or 260 mL/hour when the subject has a body mass of at least 70 kg.

In another embodiment, the amount of dextrose is 23 g, the amount of amino acids is 51 g, the amount of lipids is 11.8 g, the total volume is 397 mL, and the infusion rate is 45 mL/hour, 90 mL/hour, or 110 mL/hour when the subject has a body mass of from 34 kg to 39 kg; the amount of dextrose is 27 g, the amount of amino acids is 60 g, the amount of lipids is 13.8 g, the total volume is 458 mL, and the infusion rate is 55 mL/hour, 105 mL/hour, or 125 mL/hour when the subject has a body mass of from 40 kg to 44 kg; the amount of dextrose is 30 g, the amount of amino acids is 68 g, the amount of lipids is 15.2 g, the total volume is 509 mL, and the infusion rate is 60 mL/hour, 115 mL/hour, or 135 mL/hour when the subject has a body mass of from 45 kg to 51 kg; the amount of dextrose is 35 g, the amount of amino acids is 78 g, the amount of lipids is 17.8 g, the total volume is 579 mL, and the infusion rate is 65 mL/hour, 130 mL/hour, or 155 mL/hour when the subject has a body mass of from 52 kg to 59 kg; the amount of dextrose is 41 g, the amount of amino acids is 90 g, the amount of lipids is 21 g, the total volume is 664 mL, and the infusion rate is 75 mL/hour, 150 mL/hour, or 180 mL/hour when the subject has a body mass of from 60 kg to 69 kg; and the amount of dextrose is 47 g, the amount of amino acids is 105 g, the amount of lipids is 24 g, the total volume is 762 mL, and the infusion rate is 85 mL/hour, 175 mL/hour, or 205 mL/hour when the subject has a body mass of at least 70 kg.

In another embodiment, the amount of dextrose is 20 g, the amount of amino acids is 51 g, the amount of lipids is 10.2 g, the total volume is 385 mL, and the infusion rate is 55 mL/hour, 105 mL/hour, or 120 mL/hour when the subject has a body mass of from 34 kg to 39 kg; the amount of dextrose is 23 g, the amount of amino acids is 60 g, the amount of lipids is 11.8 g, the total volume is 442 mL, and the infusion rate is 60 mL/hour, 120 mL/hour, or 140 mL/hour when the subject has a body mass of from 40 kg to 44 kg; the amount of dextrose is 26 g, the amount of amino acids is 68 g, the amount of lipids is 13.3 g, the total volume is 493 mL, and the infusion rate is 65 mL/hour, 135 mL/hour, or 155 mL/hour when the subject has a body mass of from 45 kg to 51 kg; the amount of dextrose is 30 g, the amount of amino acids is 78 g, the amount of lipids is 15.2 g, the total volume is 559 mL, and the infusion rate is 75 mL/hour, 150 mL/hour, or 175 mL/hour when the subject has a body mass of from 52 kg to 59 kg; the amount of dextrose is 35 g, the amount of amino acids is 90 g, the amount of lipids is 17.8 g, the total volume is 639 mL, and the infusion rate is 85 mL/hour, 170 mL/hour, or 200 mL/hour when the subject has a body mass of from 60 kg to 69 kg; and the amount of dextrose is 41 g, the amount of amino acids is 105 g, the amount of lipids is 21 g, the total volume is 739 mL, and the infusion rate is 100 mL/hour, 195 mL/hour, or 230 mL/hour when the subject has a body mass of at least 70 kg.

In another embodiment, the amount of dextrose is 17 g, the amount of amino acids is 51 g, the amount of lipids is 8.6 g, the total volume is 457 mL, and the infusion rate is 75 mL/hour, 150 mL/hour, or 170 mL/hour when the subject has a body mass of from 34 kg to 39 kg; the amount of dextrose is 20 g, the amount of amino acids is 60 g, the amount of lipids is 10.2 g, the total volume is 530 mL, and the infusion rate is 90 mL/hour, 175 mL/hour, or 195 mL/hour when the subject has a body mass of from 40 kg to 44 kg; the amount of dextrose is 22 g, the amount of amino acids is 68 g, the amount of lipids is 11.2 g, the total volume is 590 mL, and the infusion rate is 100 mL/hour, 195 mL/hour, or 215 mL/hour when the subject has a body mass of from 45 kg to 51 kg; the amount of dextrose is 26 g, the amount of amino acids is 78 g, the amount of lipids is 13.2 g, the total volume is 673 mL, and the infusion rate is 110 mL/hour, 220 mL/hour, or 245 mL/hour when the subject has a body mass of from 52 kg to 59 kg; the amount of dextrose is 30 g, the amount of amino acids is 90 g, the amount of lipids is 15.2 g, the total volume is 769 mL, and the infusion rate is 130 mL/hour, 255 mL/hour, or 280 mL/hour when the subject has a body mass of from 60 kg to 69 kg; and the amount of dextrose is 35 g, the amount of amino acids is 105 g, the amount of lipids is 17.8 g, the total volume is 889 mL, and the infusion rate is 145 mL/hour, 290 mL/hour, or 325 mL/hour when the subject has a body mass of at least 70 kg.

In another embodiment, the amount of dextrose is 23 g, the amount of amino acids is 51 g, the amount of lipids is 11.8 g, the total volume is 482 mL, and the infusion rate is 60 mL/hour, 115 mL/hour, or 130 mL/hour when the subject has a body mass of from 34 kg to 39 kg; the amount of dextrose is 27 g, the amount of amino acids is 60 g, the amount of lipids is 13.8 g, the total volume is 558 mL, and the infusion rate is 65 mL/hour, 130 mL/hour, or 150 mL/hour when the subject has a body mass of from 40 kg to 44 kg; the amount of dextrose is 30 g, the amount of amino acids is 68 g, the amount of lipids is 15.2 g, the total volume is 622 mL, and the infusion rate is 75 mL/hour, 145 mL/hour, or 165 mL/hour when the subject has a body mass of from 45 kg to 51 kg; the amount of dextrose is 35 g, the amount of amino acids is 78 g, the amount of lipids is 17.8 g, the total volume is 709 mL, and the infusion rate is 85 mL/hour, 165 mL/hour, or 190 mL/hour when the subject has a body mass of from 52 kg to 59 kg; the amount of dextrose is 41 g, the amount of amino acids is 90 g, the amount of lipids is 21 g, the total volume is 814 mL, and the infusion rate is 95 mL/hour, 190 mL/hour, or 220 mL/hour when the subject has a body mass of from 60 kg to 69 kg; and the amount of dextrose is 47 g, the amount of amino acids is 105 g, the amount of lipids is 24 g, the total volume is 937 mL, and the infusion rate is 110 mL/hour, 220 mL/hour, or 250 mL/hour when the subject has a body mass of at least 70 kg.

In another embodiment, the amount of dextrose is 20 g, the amount of amino acids is 51 g, the amount of lipids is 10.2 g, the total volume is 470 mL, and the infusion rate is 65 mL/hour, 130 mL/hour, or 145 mL/hour when the subject has a body mass of from 34 kg to 39 kg; the amount of dextrose is 23 g, the amount of amino acids is 60 g, the amount of lipids is 11.8 g, the total volume is 542 mL, and the infusion rate is 75 mL/hour, 150 mL/hour, or 170 mL/hour when the subject has a body mass of from 40 kg to 44 kg; the amount of dextrose is 26 g, the amount of amino acids is 68 g, the amount of lipids is 13.2 g, the total volume is 606 mL, and the infusion rate is 85 mL/hour, 170 mL/hour, or 190 mL/hour when the subject has a body mass of from 45 kg to 51 kg; the amount of dextrose is 30 g, the amount of amino acids is 78 g, the amount of lipids is 15.2 g, the total volume is 689 mL, and the infusion rate is 95 mL/hour, 190 mL/hour, or 215 mL/hour when the subject has a body mass of from 52 kg to 59 kg; the amount of dextrose is 35 g, the amount of amino acids is 90 g, the amount of lipids is 17.8 g, the total volume is 789 mL, and the infusion rate is 110 mL/hour, 215 mL/hour, or 245 mL/hour when the subject has a body mass of from 60 kg to 69 kg; and the amount of dextrose is 41 g, the amount of amino acids is 105 g, the amount of lipids is 21 g, the total volume is 914 mL, and the infusion rate is 125 mL/hour, 250 mL/hour, or 285 mL/hour when the subject has a body mass of at least 70 kg.

In one embodiment, the invention provides a method for treating malnutrition in a hemodialysis subject in need thereof, wherein the subject does or does not have diabetes, the method comprising formulating an aqueous composition comprising between 1 and 10% mass/volume of dextrose, 7 to 20% mass/volume of amino acids and less than 5% mass/volume of lipids based on a body mass measurement of the subject and parenterally administering said aqueous composition in conjunction with the hemodialysis.

In one embodiment, the invention provides a method of treating malnutrition in a pediatric hemodialysis subject wherein the subject does or does not have diabetes, the method comprising parenterally administering a sterile aqueous composition to the subject, the composition comprising: an amount of dextrose from about 4 g to about 19 g and an amount of amino acids from about 13.5 g to about 42 g in a total volume of about 124 mL to about 357 mL, wherein the subject has a body mass of from 9 kg to 33 kg, wherein the administering is done at an infusion rate of from 17 mL/hour to 127 mL/hour.

In one embodiment, the invention provides a method of treating malnutrition in a hemodialysis subject wherein the subject does or does not have diabetes, the method comprising parenterally administering a sterile aqueous composition to the subject, the composition comprising: an amount of dextrose from about 17 g to about 47 g and an amount of amino acids from about 51 g to about 105 g in a total volume of about 329 mL to about 817 mL, wherein the subject has a body mass of from 34 kg to at least 70 kg, wherein the administering is done at an infusion rate of from 45 mL/hour to 290 mL/hour.

In one embodiment, the invention provides a method of treating malnutrition in a hemodialysis subject wherein the subject does or does not have diabetes, the method comprising parenterally administering a sterile aqueous composition to the subject, the composition comprising: an amount of dextrose from about 17 g to about 47 g, an amount of amino acids from about 51 g to about 105 g, and an amount of lipids from 8.6 g about to about 24 in a total volume of about 372 mL to about 937 mL, wherein the subject has a body mass of at least 34 kg, wherein the administering is done at an infusion rate of from 45 mL/hour to 325 mL/hour.

Compositions and methods of the invention can be modified, for example, by the age, size, or weight of the subject receiving the composition. A composition of the invention can be modified, for example, in any of: the amount of carbohydrate or amino acids contained therein; the presence or amount of lipids contained therein; the presence or amounts of micronutrients contained therein; the presence or amounts of pharmaceutical agents contained therein; the amount of fill; and the total volume. A method of the invention can be modified, for example, in the rate of administration of a composition, the frequency of administration, or the formulation of the composition used.

EXAMPLES

The following IDPN compositions are non-limiting examples of the extensive embodiments of the instant invention. In some embodiments, a formula is administered to a subject for a specified range of infusion times. In some embodiments, the formulas are fat free and micronutrient free. These examples are representative, and any IDPN composition contemplated herein can be used in the methods of the examples.

Example 1

Administration of an IDPN Composition to a Subject

To a subject, currently undergoing dialysis and in need of nutrition, is administered an IDPN composition according to FIG. 1, via a dialysis machine using techniques known to a practitioner of dialysis. The infusion rates during week one and week two of administration are selected from the infusion rates according to FIG. 2. The composition and the infusion rates are selected according to the body mass of the subject.

Example 2

Administration of an IDPN Composition to a Subject

To a subject, currently undergoing dialysis and in need of nutrition, is administered an IDPN composition according to FIG. 3, via a dialysis machine using techniques known to a practitioner of dialysis. The infusion rates during week one and week two of administration are selected from the infusion rates according to FIG. 4. The composition and the infusion rates are selected according to the body mass of the subject.

Example 3

Administration of an IDPN Composition to a Subject

To a pediatric subject, currently undergoing dialysis and in need of nutrition, is administered an IDPN composition according to FIG. 5, via a dialysis machine using techniques known to a practitioner of dialysis. The infusion rates during week one and week two of administration are selected from the infusion rates according to FIG. 6. The composition and the infusion rates are selected according to the body mass of the subject.

Example 4

Administration of an IDPN Composition to a Subject

To a pediatric subject, currently undergoing dialysis and in need of nutrition, is administered an IDPN composition according to FIG. 7, via a dialysis machine using techniques known to a practitioner of dialysis. The infusion rates during week one and week two of administration are selected from the infusion rates according to FIG. 8. The composition and the infusion rates are selected according to the body mass of the subject.

Example 5

Administration of an IDPN Composition to a Subject

To a pediatric subject, currently undergoing dialysis and in need of nutrition, is administered an IDPN composition according to FIG. 9, via a dialysis machine using techniques known to a practitioner of dialysis. The infusion rates during week one and week two of administration are selected from

Example 6

Administration of an IDPN Composition to a Subject

To a pediatric subject, currently undergoing dialysis and in need of nutrition, is administered an IDPN composition according to FIG. 11, via a dialysis machine using techniques known to a practitioner of dialysis. The infusion rates during week one and week two of administration are selected from the infusion rates according to FIG. 12. The composition and the infusion rates are selected according to the body mass of the subject.

Example 7

Administration of an IDPN Composition to a Subject

To a pediatric subject, currently undergoing dialysis and in need of nutrition, is administered an IDPN composition according to FIG. 13, via a dialysis machine using techniques known to a practitioner of dialysis. The infusion rates during week one and week two of administration are selected from the infusion rates according to FIG. 14. The composition and the infusion rates are selected according to the body mass of the subject.

Example 8

Administration of an IDPN Composition to a Subject

To a pediatric subject, currently undergoing dialysis and in need of nutrition, is administered an IDPN composition according to FIG. 15, via a dialysis machine using techniques known to a practitioner of dialysis. The infusion rates during week one and week two of administration are selected from the infusion rates according to FIG. 16. The composition and the infusion rates are selected according to the body mass of the subject.

Example 9

Administration of an IDPN Composition to a Subject

To a subject, currently undergoing dialysis and in need of nutrition, is administered an IDPN composition according to FIG. 17, via a dialysis machine using techniques known to a practitioner of dialysis. The infusion rates during week one and week two of administration are selected from the infusion rates according to FIG. 18. The composition and the infusion rates are selected according to the body mass of the subject.

Example 10

Administration of an IDPN Composition to a Subject

To a subject, currently undergoing dialysis and in need of nutrition, is administered an IDPN composition according to FIG. 19, via a dialysis machine using techniques known to a practitioner of dialysis. The infusion rates during week one and week two of administration are selected from the infusion rates according to FIG. 20. The composition and the infusion rates are selected according to the body mass of the subject.

Example 11

Administration of an IDPN Composition to a Subject

To a subject, currently undergoing dialysis and in need of nutrition, is administered an IDPN composition according to FIG. 21, via a dialysis machine using techniques known to a practitioner of dialysis. The infusion rates during week one and week two of administration are selected from the infusion rates according to FIG. 22. The composition and the infusion rates are selected according to the body mass of the subject.

Example 12

Administration of an IDPN Composition to a Subject

To a subject, currently undergoing dialysis and in need of nutrition, is administered an IDPN composition according to FIG. 23, via a dialysis machine using techniques known to a practitioner of dialysis. The infusion rates during week one and week two of administration are selected from the infusion rates according to FIG. 24. The composition and the infusion rates are selected according to the body mass of the subject.

Example 13

Administration of an IDPN Composition to a Subject

To a subject, currently undergoing dialysis and in need of nutrition, is administered an IDPN composition according to FIG. 25, via a dialysis machine using techniques known to a practitioner of dialysis. The infusion rates during week one and week two of administration are selected from the infusion rates according to FIG. 26. The composition and the infusion rates are selected according to the body mass of the subject.

Example 14

Administration of an IDPN Composition to a Subject

To a subject, currently undergoing dialysis and in need of nutrition, is administered an IDPN composition according to FIG. 27, via a dialysis machine using techniques known to a practitioner of dialysis. The infusion rates during week one and week two of administration are selected from the infusion rates according to FIG. 28. The composition and the infusion rates are selected according to the body mass of the subject.

Example 15

Administration of an IDPN Composition to a Subject

To a subject, currently undergoing dialysis and in need of nutrition, is administered an IDPN composition according to FIG. 29, via a dialysis machine using techniques known to a practitioner of dialysis. The infusion rates during week one, week two, and week three of administration are selected from the infusion rates according to FIG. 30. The composition and the infusion rates are selected according to the body mass of the subject.

Example 16

Administration of an IDPN Composition to a Subject

To a subject, currently undergoing dialysis and in need of nutrition, is administered an IDPN composition according to FIG. 31, via a dialysis machine using techniques known to a practitioner of dialysis. The infusion rates during week one, week two, and week three of administration are selected from the infusion rates according to FIG. 32. The composition and the infusion rates are selected according to the body mass of the subject.

Example 17

Administration of an IDPN Composition to a Subject

To a subject, currently undergoing dialysis and in need of nutrition, is administered an IDPN composition according to FIG. 33, via a dialysis machine using techniques known to a practitioner of dialysis. The infusion rates during week one, week two, and week three of administration are selected from the infusion rates according to FIG. 34. The composition and the infusion rates are selected according to the body mass of the subject.

Example 18

Administration of an IDPN Composition to a Subject

To a subject, currently undergoing dialysis and in need of nutrition, is administered an IDPN composition according to FIG. 35, via a dialysis machine using techniques known to a practitioner of dialysis. The infusion rates during week one, week two, and week three of administration are selected from the infusion rates according to FIG. 36. The composition and the infusion rates are selected according to the body mass of the subject.

Example 19

Administration of an IDPN Composition to a Subject

To a subject, currently undergoing dialysis and in need of nutrition, is administered an IDPN composition according to FIG. 37, via a dialysis machine using techniques known to a practitioner of dialysis. The infusion rates during week one, week two, and week three of administration are selected from the infusion rates according to FIG. 38. The composition and the infusion rates are selected according to the body mass of the subject.

Example 20

Administration of an IDPN Composition to a Subject

Figure 39:
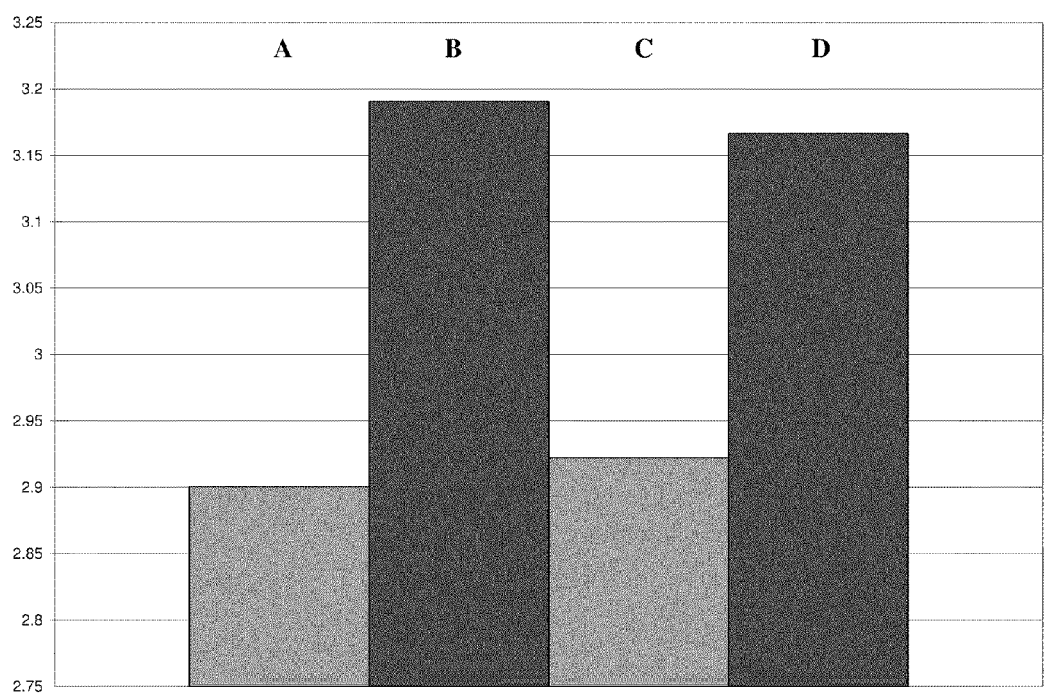
FIG. 39 illustrates the albumin levels in all subjects of a study described in Example 27. A) describes the low-volume subjects' baseline mean levels. B) describes the low-volume subjects' 3 month mean levels. C) describes the high-volume subjects' baseline mean levels. D) describes the high-volume subjects' 3 month mean levels. The y-axis describes serum albumin levels in g/L.

To a subject, currently undergoing dialysis and in need of nutrition, is administered an IDPN composition according to FIG. 39, via a dialysis machine using techniques known to a practitioner of dialysis. The infusion rates during week one, week two, and week three of administration are selected from the infusion rates according to FIG. 40. The composition and the infusion rates are selected according to the body mass of the subject.

Example 21

IDPN Composition and Regimen

The procedures described herein are a representative example of IDPN therapy, and do not provide a strict protocol for the use, administration, and monitoring of IDPN therapy.

An IDPN composition is selected using the subjects' estimated dry weight (EDW), and the length of prescribed dialysis treatment. Substrate utilization rates for carbohydrates and lipids are considered within the context of the treatment time.

A composition is formulated with a concentrated stock solution of 70% dextrose, an amino acid stock mixture 15% or 20% in amino acids, optionally, and a lipid emulsion 20% or 30% in lipid. The volume of the final composition is ≤1 liter. Subject size or compromised cardiac status can necessitate longer dialysis treatment times to allow greater infusion volumes and infusion rates. Infusion volumes greater than 1 liter can be problematic in subjects with compromised cardiac or respiratory status. Optionally, the composition is formulated with additional vitamins, minerals, and trace elements.

Half the volume of an IDPN composition lacking lipids is infused at each administration during the first week. The full volume of the composition, lacking lipids, is infused at each administration during the second week of administration. Lipids, if ordered as part of the regimen, are introduced during the third week, and, if tolerated, are continued thereafter.

The progression of infusion volumes allows observation of the subjects' physical tolerance to volume, observation of any infusion reactions, metabolic tolerance by lab monitoring, and blood pressure monitoring. Changes or additions to the IDPN composition, dialysis, and/or medication regimens are made as needed.

An IDPN composition is removed from the refrigerator at least one hour prior to the infusion. An IDPN composition is warmed to room temperature to prevent administration of a composition at low temperature; bags are removed from the refrigerator up to about 12 hours prior to the infusion. The IDPN composition bag is inspected for leaks or tears. The IDPN composition is inspected for any particulate matter or oily separation. A bag is not used if the bag is leaking or if particulate matter or separation is seen or suspected. A bag containing an IDPN composition is stable at room temperature for 24 hours. The label on the bag is inspected for the subject's name and the expiration date of the composition. The formulation listed on the bag is checked against the physician's order to confirm that the correct prescription is being given. Optionally, a multivitamin can be added to the IDPN bag itself or administered through the injection port prior to administration. The IDPN bag is hung and spiked with tubing that contains a 1.2 micron in-line filter. Alternatively, a separate 1.2 micron filter is added to regular IV tubing and the bag is spiked with the same. The tubing is primed for the type of pump being used for the infusion. Air is purged from the filter if needed. The rate of infusion is calculated to allow the infusion to complete 10 minutes prior to the scheduled end of the dialysis treatment. Optionally, time is allowed for the administration of other medications without mixing of the medication and IDPN composition. IDPN infusion is initiated through a port post dialyzer, such as the venous chamber, after the subject has been established on the machine. Optionally, insulin is added to the bag or is given subcutaneously, and the bag is labeled appropriately.

A lab profile of the subject is obtained prior to the first infusion. The subject's chart is checked for further orders pertaining to the infusion of the IDPN. If this is the initial infusion of IDPN, the subject is observed for allergic or adverse reaction. The physician can order an increase or decrease in infusion rate and/or infusion time at the beginning or end of the infusion. A calculation of the IDPN composition volume into the goal for fluid removal during each hemodialysis treatment is done to avoid fluid overload. An attendee checks for insulin orders. There is a possibility of fatty deposits occurring in the dialysis catheter and causing an obstruction. Additional flushing of the line with saline, e.g. 20 cc/lumen, is followed a heparin dose. The subject eats or drinks a snack 30 minutes prior to the end of treatment to prevent hypoglycemia. The snack should contain protein and carbohydrate.

The volume of the IDPN composition to be infused is recorded on the treatment flowsheet. The infusion rates are determined to allow an optional 15 minute window of time for the higher end of the dialysis time listed for each IDPN composition and no window for the lower end of the dialysis time Ordered glucose levels (drawn from the arterial line) and any insulin coverage listed are recorded on the flowsheet or a specific monitoring sheet. The volume infused is recorded. Subject response to the infusion, e.g. cramping, low blood pressure, high blood pressure, shortness of breath, itching, flushing, restlessness, vomiting, etc. are recorded. The IDPN infusion is stopped if an allergic reaction is suspected or the subject voices or displays unusual symptoms, vomiting, or severe hypotension, and the physician is notified. A dietitian is consulted for other issues of concern during the IDPN infusion. An RN checks for insulin orders. Discussion with the physician is advised for adjustments in formulation or administration.

Lab chemistries are optional but recommended. If chemistries are being monitored, then the phosphorus, potassium, and magnesium levels are monitored closely during the first two weeks of IDPN infusion.

Potassium levels are monitored during the first infusion of each of weeks one and two. Data are collected both pre- and post-infusion. A physician is notified if potassium levels reach 3.0 mEq/L. Potassium levels are adjusted if needed by one or more of the following methods: adjust the $K^+$ content of the bath; provide additional oral potassium replacement; provide additional potassium-containing salts to the dialysis bag; provide additional potassium-containing salts intravenously separate from the dialysis bag, such salts including potassium phosphate and potassium acetate; and provide a snack with a high potassium content.

Phosphorous levels are monitored during the first infusion of each of weeks one and two. Data are collected both pre- and post-infusion. A physician is notified if phosphorous levels reach 2.0 mEq/L. Potassium levels are adjusted if needed by one or more of the following methods: modify the amount of the phosphate binder; provide oral phosphorus-containing medication; provide oral phosphorus-containing medication; provide additional phosphorus-containing salt replacements to the dialysis bag; provide additional phosphorus-containing salt replacements intravenously separate from the dialysis bag, such salts including sodium phosphate or potassium phosphate; and provide a snack with a high phosphorus content.

Magnesium levels are monitored during the first infusion of each of weeks one and two. Data are collected both pre- and post-infusion. A physician is notified if magnesium levels reach 1.5 mEq/L. Magnesium levels are adjusted if needed by one or more of the following methods: provide magnesium-containing compounds orally, provide a magnesium replacement to the dialysis bag, or provide a magnesium replacement via dialysis separate form the dialysis bag.

Baseline composite chemistries are obtained prior to the initiation of IDPN. Lab work for potassium, phosphorus, and magnesium is obtained as frequently as needed until deemed stable. Results of lab work are recorded, and a physician is consulted as to any changes in administration. Written orders are obtained for any medication changes/prescriptions. Written orders for any desired IDPN composition changes are obtained.

An IV lipid test dose is performed on the first treatment of the third week. Triglyceride levels are monitored prior to the first infusion of the third week. A physician is notified if triglyceride levels reach ≥300 mEq/L or >50% baseline. If lipid levels must be lowered in a subject, the following procedure can be employed.

The subject's rate of caloric consumption is determined. The subject's lipid profile is determined and medication is prescribed as needed. The lipid levels in the IDPN composition are decreased to 0.15 gm/kg/hr. The subject's serum carnitine level is optionally determined. An intravenous lipid test dose infusion is performed. Observations are made for signs of intolerance, for example, wheezing, nausea, dyspnea, flushing, hypotension, cyanosis, vomiting, chest or back pain, sweating, local site irritation, pressure over the eyes, headache, or elevated temperature. Wheezing and hypotension can indicate allergic reaction. If wheezing and hypotension are observed, the infusion is stopped and the physician is notified. If the test infusion is tolerated, the rate of infusion is escalated to the desired final rate of infusion. Triglyceride levels are recorded on the IDPN flowsheet. A physician is consulted for orders or changes in the solution composition.

Blood glucose levels for every administration (drawn from the arterial line) are obtained pre-infusion, 1-hour into infusion, and post infusion. Sliding scale coverage can be used; however, insulin regimens are advised.

Glucose levels in a subject are modulated if needed by the following method. Baseline blood sugar is determined using a sample from the arterial line and a glucose monitor. 1-hour and post blood sugar readings are taken for the first two weeks of therapy. The subject is monitored for signs of hyperglycemia, e.g. headache, nausea, thirst, flushing, weakness, and rapid respirations. Regular insulin coverage might be needed. Blood sugar coverage on a sliding scale can begin at blood sugar readings of greater than 150 mg/dL or greater than 200 mg/dL, but a physician is called for blood sugars readings greater than 350 mg/dL Coverage orders are obtained when indicated for blood sugars greater than 350 mg/dL. Adjustment of the subject to the regimen can often correct the hyperglycemia without necessitating coverage. Insulin is checked hourly and glucose every 30 minutes. The blood sugar can drop after the IDPN infusion is discontinued. Subjects that are most susceptible include non-diabetic subjects, subjects receiving insulin coverage at the 1-hour mark, subjects receiving split dose insulin (NPH) that peaks during or near the cessation of the IDPN infusion. The subject might need to remain in the unit until stable, and is monitored for symptoms of hypoglycemia, e.g. headache, diplopia, dizziness, nervousness, cold sweat, nausea, and hunger. Hypoglycemia is treated with 2 teaspoons of sugar in a glass of fruit juice. Subjects eat or drink a snack about 30 minutes before the end of the IDPN infusion. The snack contains a source of protein and carbohydrate, for example, half of a meat sandwich or appropriate oral supplement. Blood glucose levels are recorded on the dialysis flowsheet.

Monthly chemistries to be monitored include dialyzer clearance rate, urea reduction ratio (URR), liver function of aminotransferases (LFT), and bicarbonate levels.

Dialyzer clearance rate is defined as Kt/V, wherein: K=mL blood/min through a dialysis machine; t=time; and V=volume. A physician is notified if a subject's rate falls below 1.2, and/or the subject's URR falls below 65%. Increased protein provision can decrease the dialyzer clearance rate.

LFT describes the activity of alanine aminotransferase (ALT) and aspartate aminotransferase (AST) in the liver. A physician is notified if a subject's LFT elevates 2× above the baseline value.

A physician is also notified if a subject's bicarbonate levels fall below 22 mmol/L. K/DOQI Nutrition Guidelines advise serum $HCO_3$ levels be at 22 mmol/L. The replacement of bicarbonate is at the clinician's discretion.

Possible actions for these events include increase in treatment time; decrease in lipid or carbohydrate amounts with monitoring; oral repletion of bicarbonate; and additional acetate in the IDPN composition. Subjects exhibiting hypertension, congestive heart failure, or edema often benefit from oral repletion of calcium carbonate as an alternative to sodium carbonate or sodium acetate. An increase in treatment time necessitates reformulation of the IDPN solution.

Physical Monitoring

| SYMPTOM | POSSIBLE CAUSE | POSSIBLE CORRECTIVE ACTION |
|---|---|---|
| Cramping | "Cold Shock" | Remove IDPN from refrigerator 12 hours before infusion. |
|  | Deficiency State: |  |
|  | Potassium | Check serum level; consider oral repletion if GI status permits |
|  | Calcium | Correct calcium deficit |
|  | Magnesium | Correct magnesium deficit |
|  | Carnitine | Obtain Carnitine level and provide IV carnitine as needed |
| Hypotension | Volume Deficit | Check calculation of UF goal; evaluate EDW; give additional NS as volume replacement |
|  | Sodium Deficit | Add sodium salt to the IDPN solution |
| Shortness of Breath | Excess Volume | Consider total volume and decrease if indicated |
|  | Rate too Rapid | Reduce rate of infusion |
|  | Low Phosphorus | Check level; Replete if indicated |
|  | Excess IV lipid | Do not exceed 4 mg/kg/min or 12.5 g/hr of IV lipid |
| Generalized Muscle Weakness or Tenderness | Mg Deficiency | Increase Magnesium in IDPN |
|  | Carnitine Deficiency | Obtain serum level; replete with oral or IV Rx as indicated |
|  | Selenium Deficiency | Obtain serum level; replete IV sodium Selenemite as indicated |

A dietitian performs monthly nutritional assessments using Albumin, normalized protein catabolic rate (nPCR), and EDW, EDW changes, and anthropometric data. Assessment of subject tolerance, physical and metabolic, is rendered and assessment of current IDPN solution is reviewed. The dietitian confers with the physician for any recommended solution changes and obtains IDPN orders as indicated. The dietitian obtains the physician signature on any new IDPN orders, forwards to the IDPN provider, and continues to monitor monthly progress.

Example 22

Epidemiological Study on IDPN Composition Infusions in Diabetic Subjects

Collected data were analyzed to evaluate the efficacy of low-volume, low-carbohydrate IDPN compositions that lacked lipids versus the efficacy of lipid-containing IDPN compositions with higher volumes and higher carbohydrate amounts. All compositions contained amino acids. Subject groups included: a) 41 diabetic adult subjects who had received high-volume IDPN compositions containing amino acids, lipids, and carbohydrates, for at least 3 consecutive months (Group I); and b) 63 diabetic adult subjects who had received low-volume IDPN compositions containing amino acids, no lipids and a lesser amount of carbohydrates than the compositions of Group I, for at least 3 consecutive months (Group II). Baseline serum data were collected for all subjects in both groups. All subjects received hemodialysis by the same method of administration three times a week, uninterrupted over the course of therapy, with infusion times in the range of 3.25-3.50 hours. An individual subject received the same IDPN composition for the duration of the therapy. An analysis was performed comparing the baseline and 3 month serum albumin levels of both groups.

Among Group I diabetic subjects the baseline mean serum albumin was 2.93±0.47 g/dL and the 3 month mean serum albumin was 3.10±0.52 g/dL. Among Group II diabetic subjects, the mean baseline serum albumin was 2.86±0.49 g/dL and the 3 month mean serum albumin was 3.18±0.33 g/dL. The mean increase in serum albumin among Group I subjects was 0.18±0.37 g/dL and the mean serum increase among Group II subjects was 0.31±0.48 g/dL. FIG. 37 provides a graph of these data; in FIG. 37: A) describes Group I subjects' baseline mean levels; B) describes Group I subjects' 3 month mean levels; C) describes Group II subjects' baseline mean levels; and D) describes Group II subjects' 3 month mean levels. The y-axis describes serum albumin levels in g/L. A two sample t-test was performed on this data and a P value of 0.059 was calculated. Group II subjects, receiving the low-volume, low-carbohydrate, lipid-free IDPN composition, exhibited a greater serum albumin change in 3 months than did the subjects of group I, at a level approaching statistical significance. Not all subjects of either group responded to the therapy, and in a minority of cases, a subject exhibited depressed albumin levels at 3 months.

Example 23

Epidemiological Study on IDPN Composition Infusions in Non-Diabetic Subjects

Collected data were analyzed to evaluate the efficacy of low-volume, low-carbohydrate IDPN compositions that lacked lipids versus the efficacy of lipid-containing IDPN compositions with higher volume and higher carbohydrate amounts. All compositions contained amino acids. Subject groups included: a) 42 non-diabetic adult subjects who had received the same high-volume IDPN composition, containing amino acids, lipids and carbohydrates, for at least 3 consecutive months (Group I); and b) 29 non-diabetic adult subjects who had received the same low volume IDPN composition, containing amino acids, no lipids and half the carbohydrates of the composition of Group I, for at least 3 consecutive months (Group II). Baseline serum data was collected for all subjects in both groups. All subjects received hemodialysis by the same method of administration three times a week, uninterrupted over the course of therapy, with infusion times in the range of 3.25-3.50 hours. Each individual subject received the same IDPN composition for the duration of the therapy. An analysis was performed comparing the baseline and 3 month serum albumin levels of both groups.

Among Group I non-diabetic subjects, the mean baseline serum albumin was 2.97±0.55 g/dL and the 3 month mean serum albumin was 3.33±0.56 g/dL. Among Group II non-diabetic subjects, the mean baseline serum albumin was 2.84±0.45 g/dL and the 3 month mean serum albumin was 3.16±0.49 g/dL. The mean increase in serum albumin among Group I subjects was 0.36±0.43 g/dL and the mean increase in serum albumin among Group II subjects was 0.31±0.75 g/dL.

Figure 38:
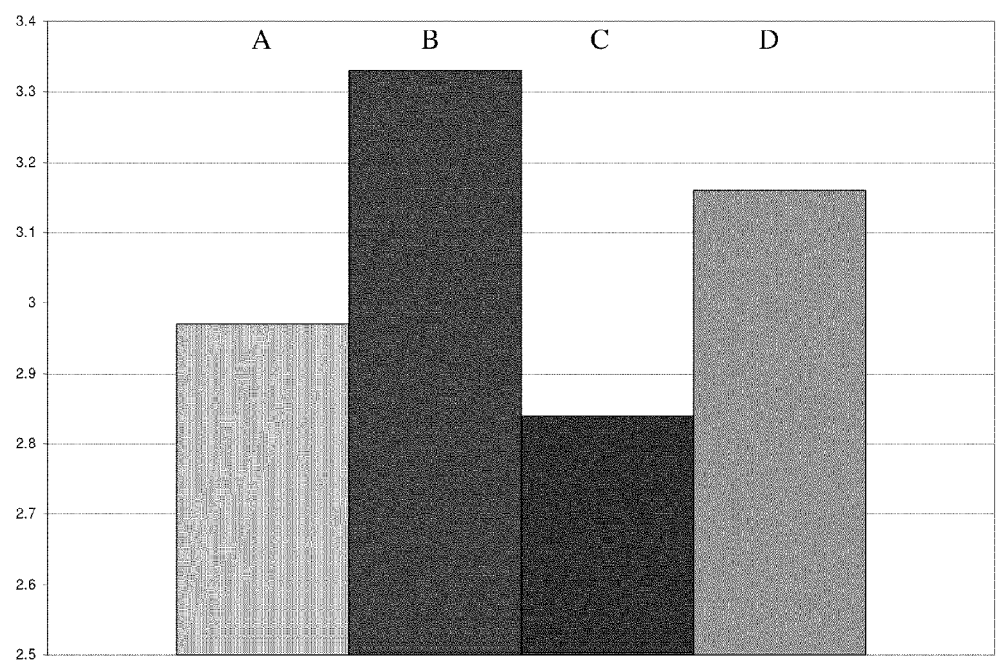
FIG. 38 illustrates the albumin levels in non-diabetic subjects of a study described in Example 23. A) describes Group I subjects' baseline mean levels. B) describes Group I subjects' 3 month mean levels. C) describes Group II subjects' baseline mean levels. D) describes Group II subjects' 3 month mean levels. The y-axis describes serum albumin levels in g/L.

FIG. 38 provides a graph of these data; in FIG. 38: A) describes Group I subjects' baseline mean levels; B) describes Group I subjects' 3 month mean levels; C) describes Group II subjects' baseline mean levels; and D) describes Group II subjects' 3 month mean levels. The y-axis describes serum albumin levels in g/L. A two sample t-test was performed on this data and a P value of 0.35 was calculated, indicating that the results were consistent form Group I to Group II. Not all subjects responded to the therapy, and in a minority of cases, a subject exhibited depressed albumin levels at 3 months.

Example 24

Epidemiological Study on IDPN Composition Infusions in Subjects Representing Statistical Outliers The data from all subjects from Group I or Group II from either Example 22 or Example 23 that experienced an increase in serum albumin levels of greater than 1.0 g/dL were examined for statistical significance. Among Group I subjects (n=2), the mean baseline serum albumin was 2.70±0.14 g/dL and the three month mean serum albumin was 4.10±0.14 g/dL. Analysis by t-test comparing the baseline mean to the three month mean provided a P value of 0.090. Among Group II subjects (n=10), the baseline mean was 2.06±0.47 g/dL and the three month mean was 3.44±0.34 g/dL. Analysis by t-test comparing the baseline to the three month mean provided a P value of <0.005. In comparing the increase in serum albumin levels of both groups, Group I exhibited a mean increase of 1.40±0.28 g/dL, and Group II exhibited a mean increase of 1.32±0.29 g/dL. Analysis by t-test of the increase in serum albumin levels between the two groups provided a P value of 0.762. The lack of statistical significance in these results is owed to the small n value of the subject set. The increases in albumin levels were consistent from Group I to Group II.

Example 25

Preparation of an IDPN Solution

To 340 mL aliquot of the amino acid stock mixture of Table II (15 g of amino acids per 100 mL) is added 33 mL of an aqueous dextrose stock solution (70 g dextrose per 100 mL). The total volume is diluted to 423 mL with an appropriate volume of fill (approximately 50 mL) to provide an IDPN composition containing 51 g of amino acids and 23 g of dextrose in a 423 mL solution (0.12 g/mL amino acids and 0.054 g/mL dextrose).

Example 26

Preparation of an IDPN Solution

To 340 mL aliquot of the amino acid stock mixture of Table II (15 g of amino acids per 100 mL) is added 33 mL of an aqueous dextrose stock solution (70 g dextrose per 100 mL) and 59 mL of a lipid stock mixture (20 g lipids per 100 mL). The total volume is diluted to 482 mL with an appropriate volume of fill (approximately 50 mL) to provide an IDPN composition containing 51 g of amino acids, 23 g of dextrose, and 11.8 g of lipids in a 482 mL solution (0.11 g/mL amino acids, 0.048 g/mL dextrose, and 0.024 g/mL lipids).

Example 27

Epidemiological Study on IDPN Composition Infusions

Collected data were analyzed to evaluate the efficacy of low-volume, low-carbohydrate IDPN compositions that lacked lipids versus the efficacy of lipid-containing IDPN compositions with high-volume and high-carbohydrate amounts. All compositions contained amino acids. The low-volume compositions had a volume of about 37% of that of the corresponding high-volume compositions. High volume compositions contained 4-6 mg of carbohydrate per kg of subject body mass for subjects requiring carbohydrate control; 6-8 mg of carbohydrate per kg of subject body mass for subjects not requiring carbohydrate control; and lipids administered at the lower of 4 mg lipids per kg subject body mass per minute, or 12 g/hr. The amount of carbohydrates administered to an individual subject was related to the body mass of the individual subject, and the composition administered to each subject was formulated accordingly.

A total of 368 subjects began the study. 222 subjects received the low-volume IDPN compositions, and 146 subjects received the high-volume IDPN compositions. In the low-volume group, 21 subjects were disqualified for having base line albumin levels greater than 3.5 g/dL, and 1 for providing incomplete information. In the high-volume group, 19 subjects were disqualified for having base line serum albumin levels greater than 3.5 g/dL, and 2 for providing incomplete data. Of the 325 subjects who completed the study, 200 were in the low-volume group and 125 were in the high-volume group. 139 subjects in the low-volume group and 70 subjects in the high-volume group were diabetic. A survey of the body mass index of all subjects found that the average body mass index of the subjects in the low-volume, low-carbohydrate group was higher than that of the subjects in the high-volume, high-carbohydrate group.

A comparison was made of all subjects remaining in the low-volume and high-volume IDPN groups. The low-volume group had a baseline mean serum albumin of 2.90±0.46 g/dL, and a 3 month mean serum albumin of 3.19±0.39 g/dL. The high-volume group had a baseline mean serum albumin of 2.92±0.45 g/dL, and a 3 month mean serum albumin of 3.17±0.51 g/dL. The gain in mean serum albumin for the low-volume group was 0.29±0.46 g/dL. The gain in mean serum albumin for the high-volume group was 0.24±0.41 g/dL. Analysis by t-test resulted in a p=0.18, above the threshold of p=0.05 for statistical significance. The results are illustrated in FIG. 39.

Figure 40:
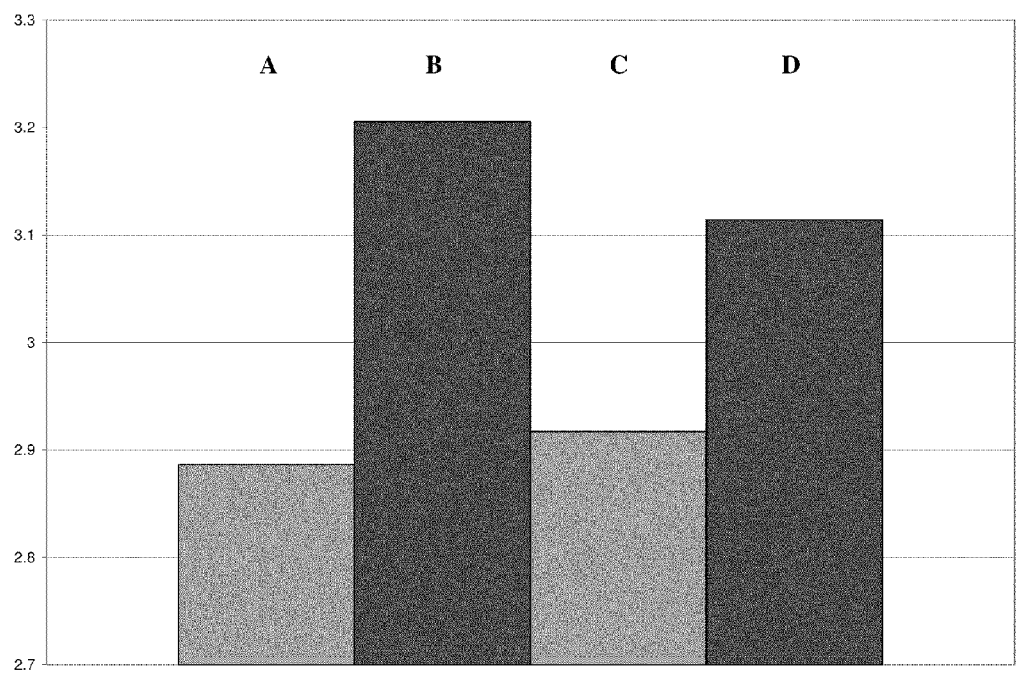
FIG. 40 illustrates the albumin levels in the diabetic subjects of a study described in Example 27. A) describes the low-volume diabetic subjects' baseline mean levels. B) describes the low-volume diabetic subjects' 3 month mean levels. C) describes the high-volume diabetic subjects' baseline mean levels. D) describes the high-volume diabetic subjects' 3 month mean levels. The y-axis describes serum albumin levels in g/L.

A separate comparison was made of the diabetic subjects receiving low-volume versus high-volume IDPN compositions. The diabetic low-volume group had a baseline mean serum albumin of 2.89±0.48 g/dL, and a 3 month mean serum albumin of 3.21±0.37 g/dL. The diabetic high-volume group had a baseline mean serum albumin of 2.92±0.40, and a 3 month mean serum albumin of 3.11±0.49 g/dL. The gain in mean serum albumin for the diabetic low-volume group was 0.32±0.47 g/dL. The gain in mean serum albumin for the diabetic high-volume group was 0.20±0.35. Analysis by t-test resulted in a p=0.018, below the threshold of p=0.05 for statistical significance. The results are illustrated in FIG. 40.

In this study, 15 subjects exhibited a mean serum albumin increase of >1.0 g/dL. 14 of these 15 subjects had received the low-volume IDPN composition. 12 of these 14 were diabetic.

The low-volume, low-carbohydrate group, having a greater average body mass index than the high-volume, high-carbohydrate group, responded to therapy despite having larger physical size and higher caloric needs. This counterintuitive observation suggests that subjects of varying body size can benefit from the advantages of the low-volume therapy.

Figure 41:
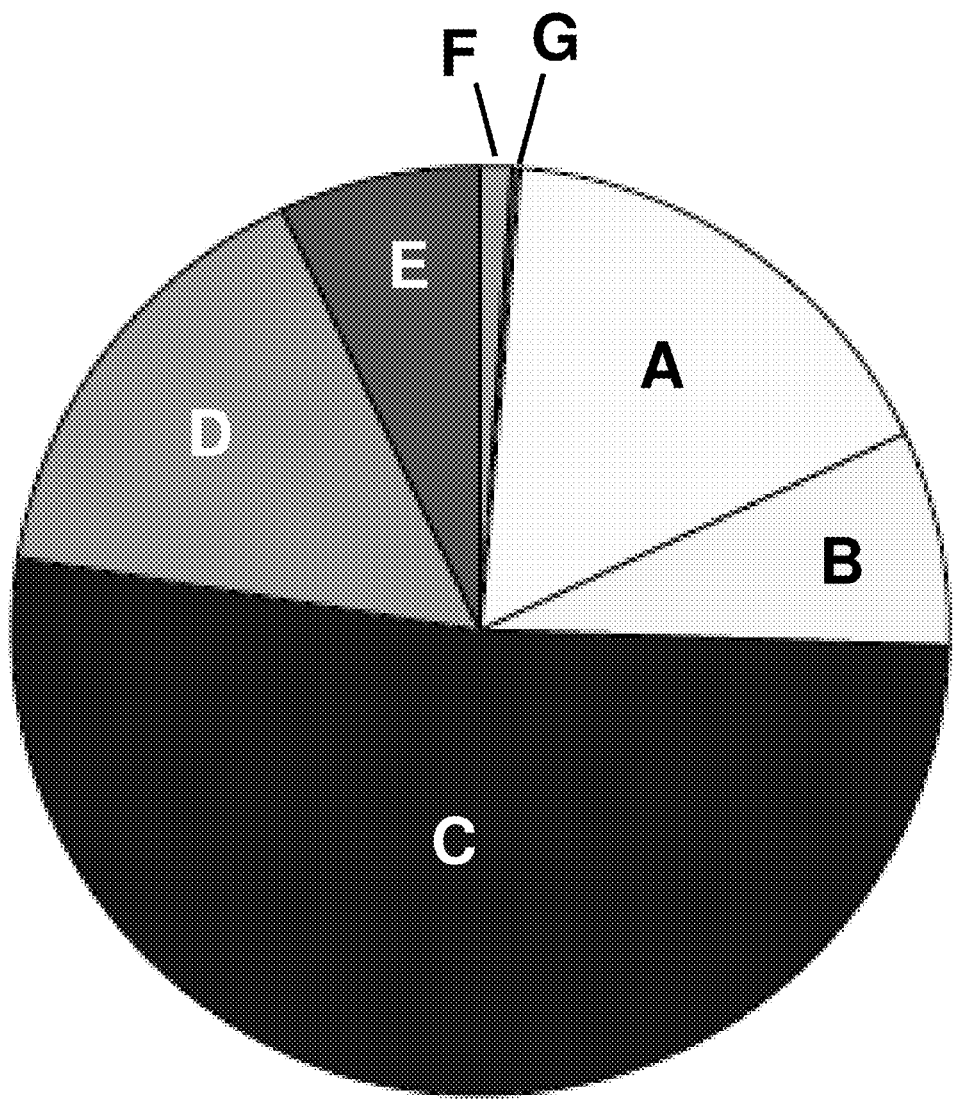
FIG. 41 illustrates a chart of the response of subjects receiving the low-volume IDPN composition in Example 27.

FIG. 41 illustrates the levels of increase or decrease in serum albumin among subjects receiving the low-volume IDPN composition. Subjects of sub-population A (33 subjects; 16% of total subjects receiving the low-volume IDPN composition) exhibited an albumin decrease of 0.01 to 0.5 g/dL. Subjects of sub-population B (15 subjects; 8% of total subjects receiving the low-volume IDPN composition) exhibited an albumin increase of 0 g/dL. Subjects of sub-population C (104 subjects; 51% of total subjects receiving the low-volume IDPN composition) exhibited an albumin increase of 0.01 to 0.5 g/dL. Subjects of sub-population D (31 subjects; 16% of total subjects receiving the low-volume IDPN composition) exhibited an albumin increase of 0.51 to 1 g/dL. Subjects of sub-population E (14 subjects; 7% of total subjects receiving the low-volume IDPN composition) exhibited an albumin increase of greater than 1 g/dL. Subjects of sub-population F (2 subjects; 1% of total subjects receiving the low-volume IDPN composition) exhibited an albumin decrease of greater than 1 g/dL. Subjects of sub-population G (1 subjects; 1% of total subjects receiving the low-volume IDPN composition) exhibited an albumin decrease of 0.51 to 1 g/dL.

Figure 42:
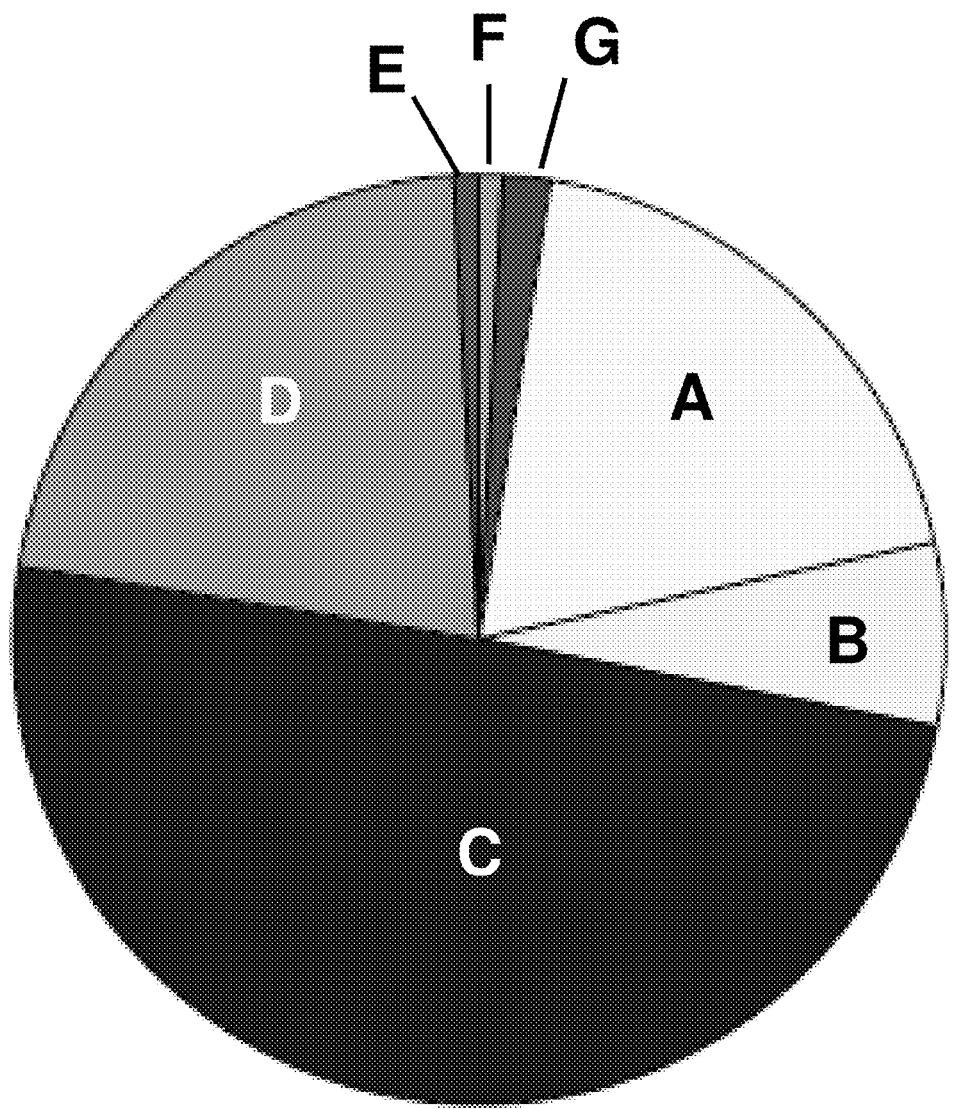
FIG. 42 illustrates a chart of the response of subjects receiving the high-volume IDPN composition in Example 27.

FIG. 42 illustrates the levels of increase or decrease in serum albumin among subjects receiving the high-volume IDPN composition. Subjects of sub-population A (24 subjects; 19% of total subjects receiving the high-volume IDPN composition) exhibited an albumin decrease of 0.01 to 0.5 g/dL. Subjects of sub-population B (8 subjects; 6% of total subjects receiving the high-volume IDPN composition) exhibited an albumin increase of 0 g/dL. Subjects of sub-population C (62 subjects; 49% of total subjects receiving the high-volume IDPN composition) exhibited an albumin increase of 0.01 to 0.5 g/dL. Subjects of sub-population D (27 subjects; 22% of total subjects receiving the high-volume IDPN composition) exhibited an albumin increase of 0.51 to 1 g/dL. Subjects of sub-population E (1 subjects; 1% of total subjects receiving the high-volume IDPN composition) exhibited an albumin increase of greater than 1 g/dL. Subjects of sub-population F (1 subjects; 1% of total subjects receiving the high-volume IDPN composition) exhibited an albumin decrease of greater than 1 g/dL. Subjects of sub-population G (2 subjects; 2% of total subjects receiving the high-volume IDPN composition) exhibited an albumin decrease of 0.51 to 1 g/dL.

Figure 43:
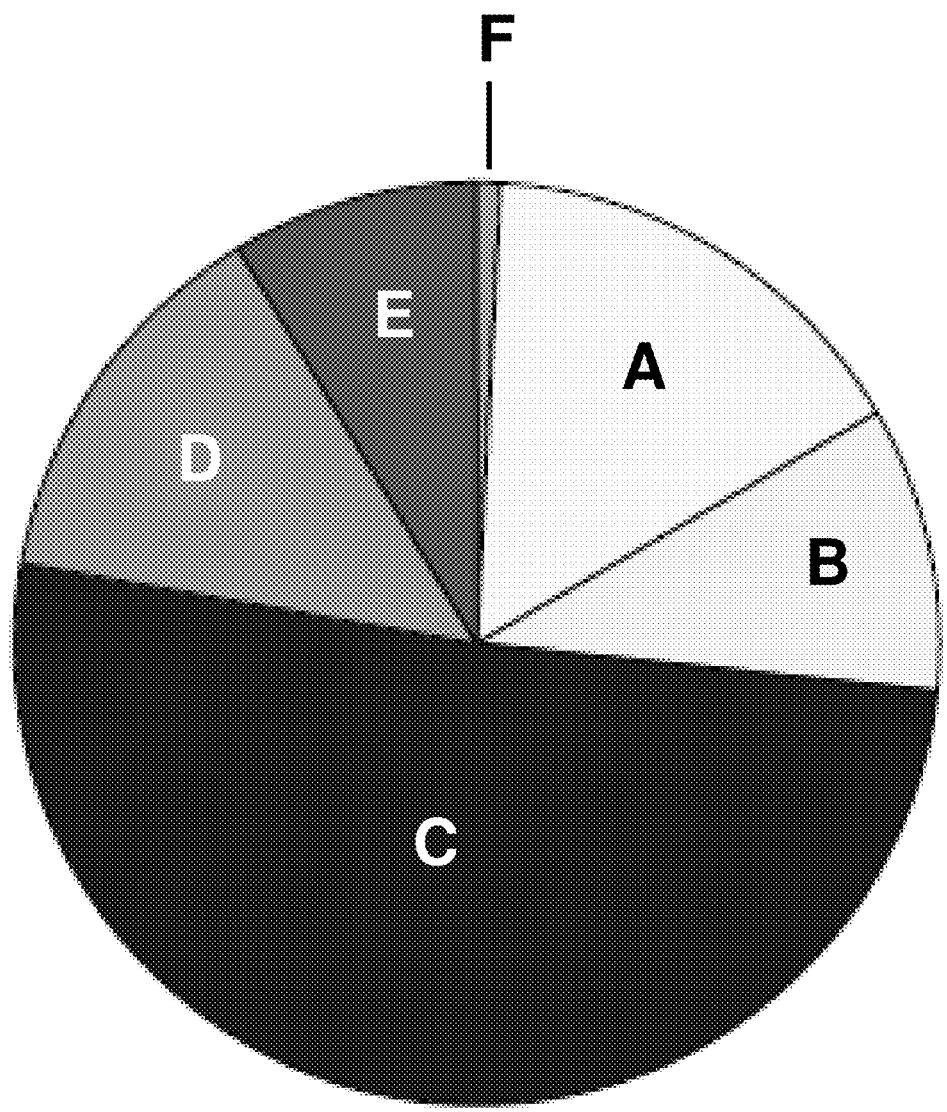
FIG. 43 illustrates a chart of the response of diabetic subjects to the low-volume IDPN composition in Example 27.

FIG. 43 illustrates the levels of increase or decrease in serum albumin among diabetic subjects to the low-volume IDPN composition. Subjects of sub-population A (22 subjects; 16% of diabetic subjects receiving the low-volume IDPN composition) exhibited an albumin decrease of 0.01 to 0.5 g/dL. Subjects of sub-population B (14 subjects; 10% of diabetic subjects receiving the low-volume IDPN composition) exhibited an albumin increase of 0 g/dL. Subjects of sub-population C (71 subjects; 50% of diabetic subjects receiving the low-volume IDPN composition) exhibited an albumin increase of 0.01 to 0.5 g/dL. Subjects of sub-population D (19 subjects; 14% of diabetic subjects receiving the low-volume IDPN composition) exhibited an albumin increase of 0.51 to 1 g/dL. Subjects of sub-population E (12 subjects; 9% of diabetic subjects receiving the low-volume IDPN composition) exhibited an albumin increase of greater than 1 g/dL. Subjects of sub-population F (1 subjects; 1% of diabetic subjects receiving the low-volume IDPN composition) exhibited an albumin decrease of greater than 1 g/dL. Zero subjects receiving the low-volume IDPN composition exhibited an albumin decrease of 0.51 to 1 g/dL.

Figure 44:
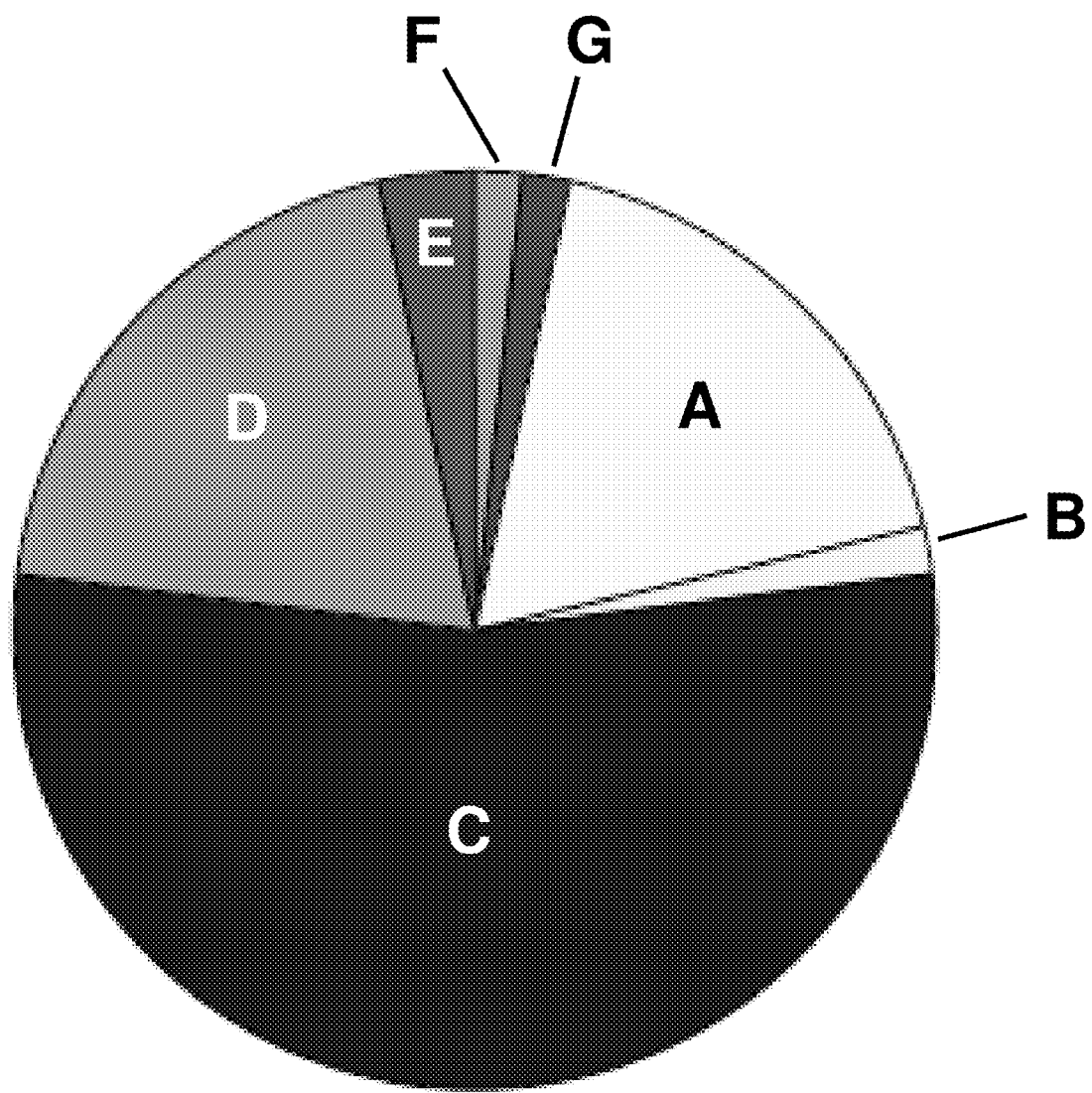
FIG. 44 illustrates a chart of the response of non-diabetic subjects to the low-volume IDPN composition in Example 27.

FIG. 44 illustrates the levels of increase or decrease in serum albumin among non-diabetic subjects to the low-volume IDPN composition. Subjects of sub-population A (11 subjects; 18% of non-diabetic subjects receiving the low-volume IDPN composition) exhibited an albumin decrease of 0.01 to 0.5 g/dL. Subjects of sub-population B (1 subjects; 2% of non-diabetic subjects receiving the low-volume IDPN composition) exhibited an albumin increase of 0 g/dL. Subjects of sub-population C (33 subjects; 53% of non-diabetic subjects receiving the low-volume IDPN composition) exhibited an albumin increase of 0.01 to 0.5 g/dL. Subjects of sub-population D (12 subjects; 20% of non-diabetic subjects receiving the low-volume IDPN composition) exhibited an albumin increase of 0.51 to 1 g/dL. Subjects of sub-population E (2 subjects; 3% of non-diabetic subjects receiving the low-volume IDPN composition) exhibited an albumin increase of greater than 1 g/dL. Subjects of sub-population F (1 subjects; 2% of non-diabetic subjects receiving the low-volume IDPN composition) exhibited an albumin decrease of greater than 1 g/dL. Subjects of sub-population G (1 subjects; 2% of non-diabetic subjects receiving the low-volume IDPN composition) exhibited an albumin decrease of 0.51 to 1 g/dL.

What is claimed is:

1. A method, comprising administering a sterile aqueous intradialytic parenteral, nutrition (IDPN) solution to a human subject in need thereof, the IDPN solution comprising between 0.02 g/mL and 0.1 g/mL of dextrose and between 0.1 g/mL and 0.2 g/mL of amino acids, wherein the solution is lipid-free and the dextrose and the amino acids are both present in the same aqueous solution, and wherein the IDPN solution, when administered to the human subject as part of an intradialytic parenteral nutrition treatment regimen over a period of at least three months, produces a sustained increase in the serum albumin level in the blood of the subject from about 0.01 g/dL to about 1.0 g/dL.

2. A method, comprising administering a sterile aqueous IDPN solution to a human subject in need thereof, the IDPN solution comprising between 0.02 g/mL and 0.1 g/mL of dextrose, between 0.1 g/mL and 0.2 g/mL of amino acids, and between 0.01 g/mL and 0.05 g/mL of lipids, wherein the dextrose, the amino acids, and the lipids are all present in the same aqueous solution, and wherein the IDPN solution , when administered to the human subject as part of an intradialytic parenteral nutrition treatment regimen over a period of at least three months, produces a sustained increase in the serum albumin level in the blood of the subject from about 0.01 g/dL to about 1.0 g/dL.

3. The method of claim 1 or 2, wherein the amino acids comprise seventeen amino acids.

4. The method of claim 3, wherein the seventeen amino acids are lysine, leucine, phenylalanine, valine, histidine, isoleucine, methionine, threonine, tryptophan, alanine, arginine, glycine, proline, glutamic acid, serine, aspartic acid, and tyrosine.

5. The method of claim 1 or 2, wherein the IDPN solution comprises between 0.04 g/mL and 0.08 g/mL of dextrose and between 0.12 g/mL and 0.18 g/mL of amino acids.

6. The method of claim 1 or 2, wherein the IDPN solution comprises between 0.05 g/mL and 0.07 g/mL of dextrose and between 0.15 g/mL and 0.17 g/mL of amino acids.

7. The method of claim 1 or 2, wherein the IDPN solution comprises between 0.04 g/mL and 0.08 g/mL of dextrose and between 0.15 g/mL and 0.17 g/mL of amino acids.

8. The method of claim 1 or 2, wherein the IDPN solution comprises between 0.05 g/mL and 0.07 g/mL of dextrose and between 0.12 g/mL and 0.18 g/mL of amino acids.

9. The method of claim 1 or 2, wherein the IDPN solution comprises between 0.12 g/mL and 0.18 g/mL of amino acids.

10. The method of claim 1 or 2, wherein the IDPN solution comprises between 0.15 g/mL and 0.17 g/mL of amino acids.

11. The method of claim 1 or 2, wherein the IDPN solution, when administered to the human subject as part of an intradialytic parenteral nutrition treatment regimen over a period of at least three months, produces a sustained increase in the serum albumin level in the blood of the subject from about 0.1 g/dL to about 0.6 g/dL.

12. The method of claim 1 or 2, wherein the IDPN solution, when administered to the human subject as part of an intradialytic parenteral nutrition treatment regimen over a period of at least three months, produces a sustained increase in the serum albumin level in the blood of the subject from about 0.2 g/dL to about 0.4 g/dL.

13. The method of claim 1 or 2, wherein the IDPN solution has a volume between about 100 mL and about 2 liters.

14. The method of claim 1 or 2, wherein the IDPN solution has a volume between about 350 mL and about 635 mL.

15. The method of claim 1 or 2, wherein the IDPN solution, when administered to the human subject as part of an intradialytic parenteral nutrition treatment regimen, does not induce hyperglycemia in the subject.

16. The method of claim 1 or 2, wherein the IDPN solution comprises vitamins and minerals.

17. A method, comprising administering a sterile aqueous intradialytic parenteral, nutrition (IDPN) solution a human subject in need thereof, the IDPN solution consisting essentially of between 0.02 g/mL and 0.1 g/mL of dextrose and between 0.1 g/mL and 0.2 g/mL of amino acids, wherein the solution is lipid-free and the dextrose and the amino acids are both present in the same aqueous solution, and wherein the IDPN solution, when administered to the human subject as part of an intradialytic parenteral nutrition treatment regimen over a period of at least three months, produces a sustained increase in the serum albumin level in the blood of the subject from about 0.01 g/dL to about 1.0 g/dL.

18. A method, comprising administering a sterile aqueous IDPN solution a human subject in need thereof, the IDPN solution consisting essentially of between 0.02 g/mL and 0.1 g/mL of dextrose, between 0.1 g/mL and 0.2 g/mL of amino acids, and between 0.01 g/mL and 0.05 g/mL of lipids, wherein the dextrose, the amino acids, and the lipids are all present in the same aqueous solution, and wherein the IDPN solution, when administered to the human subject as part of an intradialytic parenteral nutrition treatment regimen over a period of at least three months, produces a sustained increase in the serum albumin level in the blood of the subject from about 0.01 g/dL to about 1.0 g/dL.

19. The method of claim 17, wherein the IDPN solution consists essentially of between 0.04 g/mL and 0.08 g/mL of dextrose and between 0.12 g/mL and 0.18 g/mL of amino acids.

20. The method of claim 17, wherein the IDPN solution consists essentially of between 0.05 g/mL and 0.07 g/mL of dextrose and between 0.15 g/mL and 0.17 g/mL of amino acids.

21. The method of claim 18, wherein the IDPN solution consists essentially of between 0.04 g/mL and 0.08 g/mL of dextrose, between 0.12 g/mL and 0.18 g/mL of amino acids, and between 0.01 g/mL and 0.05 g/mL of lipids.

22. The method of claim 18, wherein the IDPN solution consists essentially of between 0.05 g/mL and 0.07 g/mL of dextrose, between 0.15 g/mL and 0.17 g/mL of amino acids, and between 0.01 g/mL and 0.05 g/mL of lipids.

23. The method of claim 17 or 18, wherein the IDPN solution, when administered to the human subject as part of an intradialytic parenteral nutrition treatment regimen over a period of at least three months, produces a sustained increase in the serum albumin level in the blood of the subject from about 0.1 g/dL to about 0.6 g/dL.

24. The method of claim 17 or 18, wherein the IDPN solution, when administered to the human subject as part of an intradialytic parenteral nutrition treatment regimen over a period of at least three months, produces a sustained increase in the serum albumin level in the blood of the subject from about 0.2 g/dL to about 0.4 g/dL.

25. The method of claim 17 or 18, wherein the IDPN solution, when administered to the human subject as part of an intradialytic parenteral nutrition treatment regimen, does not induce hyperglycemia in the subject.

26. The method of claim 1 or 2, wherein the human subject is diabetic.

27. The method of claim 26, further comprising administering insulin to the subject.

28. The method of claim 26, further comprising monitoring glucose tolerance in the subject.

29. The method of claim 28, further comprising administering insulin to the subject.

30. The method of claim 26, wherein the IDPN solution comprises between 0.04 g/mL and 0.08 g/mL of dextrose and between 0.12 g/mL and 0.18 g/mL of amino acids.

31. The method of claim 26, wherein the IDPN solution comprises between 0.05 g/mL and 0.07 g/mL of dextrose and between 0.15 g/mL and 0.17 g/mL of amino acids.

32. The method of claim 26, wherein the IDPN solution comprises between 0.04 g/mL and 0.08 g/mL of dextrose and between 0.15 g/mL and 0.17 g/mL of amino acids.

33. The method of claim 26, wherein the IDPN solution comprises between 0.05 g/mL and 0.07 g/mL of dextrose and between 0.12 g/mL and 0.18 g/mL of amino acids.

34. The method of claim 26, wherein the IDPN solution comprises between 0.12 g/mL and 0.18 g/mL of amino acids.

35. The method of claim 26, wherein the IDPN solution comprises between 0.15 g/mL and 0.17 g/mL of amino acids.

36. The method of claim 26, wherein the IDPN solution, when administered to the diabetic human subject as part of an intradialytic parenteral nutrition treatment regimen over a period of at least three months, produces a sustained increase in the serum albumin level in the blood of the subject from about 0.1 g/dL to about 0.6 g/dL.

37. The method of claim 26, wherein the IDPN solution, when administered to the diabetic human subject as part of an intradialytic parenteral nutrition treatment regimen over a period of at least three months, produces a sustained increase in the serum albumin level in the blood of the subject from about 0.2 g/dL to about 0.4 g/dL.

38. The method of claim 17, wherein the human subject is diabetic.

39. The method of claim 38, further comprising administering insulin to the subject.

40. The method of claim 38 or 39, further comprising monitoring glucose tolerance in the subject.

41. The method of claim 38, wherein the IDPN solution consists essentially of between 0.04 g/mL and 0.08 g/mL of dextrose and between 0.12 g/mL and 0.18 g/mL of amino acids.

42. The method of claim 38, wherein the IDPN solution consists essentially of between 0.05 g/mL and 0.07 g/mL of dextrose and between 0.15 g/mL and 0.17 g/mL of amino acids.

43. The method of claim 38, wherein the IDPN solution, when administered to the diabetic human subject as part of an intradialytic parenteral nutrition treatment regimen over a period of at least three months, produces a sustained increase in the serum albumin level in the blood of the subject from about 0.1 g/dL to about 0.6 g/dL.

44. The method of claim 38, wherein the IDPN solution, when administered to the diabetic human subject as part of an intradialytic parenteral nutrition treatment regimen over a period of at least three months, produces a sustained increase in the serum albumin level in the blood of the subject from about 0.2 g/dL to about 0.4 g/dL.

45. The method of claim 18, wherein the human subject is diabetic.

46. The method of claim 45, further comprising administering insulin to the subject.

47. The method of claim 45 or 46, further comprising monitoring glucose tolerance in the subject.

48. The method of claim 45, wherein the IDPN solution consists essentially of between 0.04 g/mL and 0.08 g/mL of dextrose, between 0.12 g/mL and 0.18 g/mL of amino acids, and between 0.01 g/mL and 0.05 g/mL of lipids.

49. The method of claim 45, wherein the IDPN solution consists essentially of between 0.05 g/mL and 0.07 g/mL of dextrose, between 0.15 g/mL and 0.17 g/mL of amino acids, and between 0.01 g/mL and 0.05 g/mL of lipids.

50. The method of claim 45, wherein the IDPN solution, when administered to the diabetic human subject as part of an intradialytic parenteral nutrition treatment regimen over a period of at least three months, produces a sustained increase in the serum albumin level in the blood of the subject from about 0.1 g/dL to about 0.6 g/dL.

51. The method of claim 45, wherein the IDPN solution, when administered to the diabetic human subject as part of an intradialytic parenteral nutrition treatment regimen over a period of at least three months, produces a sustained increase in the serum albumin level in the blood of the subject from about 0.2 g/dL to about 0.4 g/dL.

* * * * *